(12) United States Patent
Yavari et al.

(10) Patent No.: US 12,357,410 B2
(45) Date of Patent: Jul. 15, 2025

(54) HEIGHT ADJUSTABLE MEDICAL BUCKET

(71) Applicant: Stryker Corporation, Kalamazoo, MI (US)

(72) Inventors: Fazel Yavari, Portage, MI (US); Brian James VanDerWoude, Portage, MI (US); Vladimir Zagatsky, San Francisco, CA (US)

(73) Assignee: Stryker Corporation, Portage, MI (US)

( * ) Notice: Subject to any disclaimer, the term of this patent is extended or adjusted under 35 U.S.C. 154(b) by 231 days.

(21) Appl. No.: 17/794,043

(22) PCT Filed: Jan. 21, 2021

(86) PCT No.: PCT/US2021/014284
§ 371 (c)(1),
(2) Date: Jul. 20, 2022

(87) PCT Pub. No.: WO2021/150661
PCT Pub. Date: Jul. 29, 2021

(65) Prior Publication Data
US 2023/0038332 A1 Feb. 9, 2023

Related U.S. Application Data

(60) Provisional application No. 63/109,740, filed on Nov. 4, 2020, provisional application No. 62/963,653, filed on Jan. 21, 2020.

(51) Int. Cl.
*A61B 50/13* (2016.01)
*A61B 50/36* (2016.01)
*A61B 50/37* (2016.01)

(52) U.S. Cl.
CPC .............. *A61B 50/13* (2016.02); *A61B 50/36* (2016.02); *A61B 2050/375* (2016.02)

(58) Field of Classification Search
CPC ... A61B 50/13; A61B 50/36; A61B 2050/375; B62B 3/02; B62B 5/065; B62B 2206/06; A61G 12/001
See application file for complete search history.

(56) References Cited

U.S. PATENT DOCUMENTS

| 2,203,059 A | 6/1940 | Palm |
| 3,808,634 A | 5/1974 | Szabo |

(Continued)

FOREIGN PATENT DOCUMENTS

| CN | 201840835 U | 5/2011 |
| CN | 105640093 A | 6/2016 |

(Continued)

OTHER PUBLICATIONS

Outpatient surgery magazine Jan. 2016 article "Elevate Your Kick Bucket" by OSD staff https://www.aorn.org/outpatient-surgery/article/2016-January-ideas-that-work-ergonomics (Year: 2016).*

(Continued)

*Primary Examiner* — Eret C McNichols
*Assistant Examiner* — Ding Y Tan
(74) *Attorney, Agent, or Firm* — Howard & Howard Attorneys PLLC

(57) ABSTRACT

A height-adjustable bucket or height-adjustable stand is adapted to carry a medical object. The bucket includes a receptacle for carrying the medical object, a base, and a support member coupled to the base. The bucket also includes a carrier movably coupled to the support member and for supporting the receptacle and a lifting member slidably coupled to the carrier and configured to move between a raised position and a lowered position. The lifting member includes a first end portion comprising a handle and a second end portion, and a retainer selectively coupling the carrier to the support member and configured to selectively (Continued)

retain the carrier in the relatively high position. The lifting member is configured to be in the lowered position when the carrier is in the relatively high position and when the carrier is in the relatively low position.

20 Claims, 53 Drawing Sheets

(56) References Cited

U.S. PATENT DOCUMENTS

| | | | |
|---|---|---|---|
| 3,863,985 A | | 2/1975 | Zuber |
| 3,998,491 A | | 12/1976 | Diem |
| 5,181,393 A | | 1/1993 | Lott |
| 5,337,581 A | | 8/1994 | Lott |
| 5,370,111 A | | 12/1994 | Reeder et al. |
| 5,454,625 A | | 10/1995 | Christensen et al. |
| 5,758,888 A | | 6/1998 | Burgan et al. |
| 5,806,943 A | | 9/1998 | Dell et al. |
| 5,890,737 A | | 4/1999 | Hutka |
| 5,941,182 A | | 8/1999 | Greene |
| 6,343,556 B1 | | 2/2002 | Lanphear |
| 6,378,816 B1 | | 4/2002 | Pfister |
| 6,431,319 B1 | | 8/2002 | Myers et al. |
| 6,607,170 B1 | | 8/2003 | Hoftman |
| 6,883,439 B1 | | 4/2005 | Moore |
| 7,171,890 B2 | | 2/2007 | Oudelaar |
| D548,918 S | * | 8/2007 | Nussberger ............... D34/17 |
| 7,594,668 B2 | | 9/2009 | Arceta et al. |
| 8,091,841 B2 | | 1/2012 | Jones et al. |
| 8,172,255 B1 | | 5/2012 | Martin |
| 8,215,650 B2 | | 7/2012 | Arceta et al. |
| 8,245,652 B2 | * | 8/2012 | Hung ............... A61B 50/15 |
| | | | 280/47.35 |
| 8,448,907 B2 | | 5/2013 | Witschen |
| D687,147 S | * | 7/2013 | Yoshida ............... D24/185 |
| 8,692,140 B1 | * | 4/2014 | Pollock ............... A61B 50/37 |
| | | | 177/15 |
| D708,341 S | * | 7/2014 | Ikegame ............... D24/185 |
| 8,963,025 B2 | | 2/2015 | Pollock et al. |
| 9,039,016 B2 | | 5/2015 | Abernethy et al. |
| 9,046,213 B2 | | 6/2015 | Huang |
| 9,347,817 B2 | | 5/2016 | Pollock et al. |
| 9,475,514 B2 | | 10/2016 | Hardy et al. |
| 9,775,430 B2 | * | 10/2017 | Abu-Akel ............... A47B 21/02 |
| 9,933,106 B2 | | 4/2018 | Stark |
| 9,993,076 B2 | * | 6/2018 | Harrington ........... A47B 83/045 |
| D824,521 S | * | 7/2018 | Adams ............... D24/158 |
| 10,407,087 B1 | | 9/2019 | Baker et al. |
| D863,559 S | * | 10/2019 | Brooks ............... D24/185 |
| 11,684,444 B2 | * | 6/2023 | Yavari ............... A61B 50/37 |
| | | | 206/438 |
| 2002/0092853 A1 | | 7/2002 | Wang |
| 2004/0262867 A1 | * | 12/2004 | Arceta ............... A61G 12/001 |
| | | | 280/47.35 |
| 2006/0006726 A1 | | 1/2006 | Garvey |
| 2007/0227409 A1 | * | 10/2007 | Chu ............... A47B 21/00 |
| | | | 108/50.02 |
| 2008/0029416 A1 | | 2/2008 | Paxton |
| 2008/0252045 A1 | | 10/2008 | Rossini et al. |
| 2010/0303603 A1 | * | 12/2010 | Galante ............... F16M 13/00 |
| | | | 414/811 |
| 2011/0232535 A1 | * | 9/2011 | Hung ............... A61G 12/001 |
| | | | 108/50.02 |
| 2011/0272902 A1 | * | 11/2011 | Arceta ............... B62B 3/1476 |
| | | | 280/47.35 |
| 2012/0024864 A1 | | 2/2012 | Champ |
| 2013/0126682 A1 | | 5/2013 | Tholkes et al. |
| 2013/0307237 A1 | * | 11/2013 | Chen ............... A61G 12/001 |
| | | | 280/35 |
| 2014/0077050 A1 | | 3/2014 | Huang |
| 2014/0265193 A1 | * | 9/2014 | Stark ............... F16M 11/045 |
| | | | 248/289.11 |
| 2014/0360412 A1 | | 12/2014 | Zaccai et al. |
| 2015/0168207 A1 | * | 6/2015 | Pollock ............... A61B 5/208 |
| | | | 177/1 |
| 2015/0227127 A1 | * | 8/2015 | Miller ............... G16H 20/13 |
| | | | 700/244 |
| 2016/0207556 A1 | * | 7/2016 | Unrath ............... B62B 3/027 |
| 2016/0367329 A1 | * | 12/2016 | Dekel ............... A61B 50/20 |
| 2017/0258547 A1 | | 9/2017 | Karasina |
| 2018/0368933 A1 | * | 12/2018 | Henniges ............... B09B 3/0075 |
| 2020/0345445 A1 | * | 11/2020 | Yavari ............... A61B 50/13 |
| 2021/0316440 A1 | | 10/2021 | Peterson et al. |

FOREIGN PATENT DOCUMENTS

| | | | | |
|---|---|---|---|---|
| CN | 106263557 A | | 1/2017 | |
| CN | 109179243 A | | 1/2019 | |
| CN | 208470711 U | | 2/2019 | |
| KR | 20140073178 A | * | 6/2014 | |
| KR | 102055270 B1 | * | 12/2019 | |
| WO | 2004047660 A1 | | 6/2004 | |
| WO | WO-2006020862 A2 | * | 2/2006 | ........... A61B 5/0002 |
| WO | 2017191591 A1 | | 11/2017 | |
| WO | 2018014219 A1 | | 1/2018 | |

OTHER PUBLICATIONS

"Spring Plunger Locking Mechanism for Use in Hand-Actuated Tools" Mar. 1, 2018 online tech briefs article by Andrew Willig for Nasa's jet propulsion laboratory, https://www.techbriefs.com/component/content/article/28542-npo-49901 (Year: 2018).*

JW Winco spring plungers youtube video dated Sep. 16, 2019, https://www.youtube.com/watch?v=BoHzikg6cjE (Year: 2019).*

Blickman, "7807MR-HB MR Single Basin Solution Stand Webpage", https://www.blickman.com/category/solution-stands/p/mr_single_basin_solution_stand_0717807066. 2022, 5 pages.

Blickman, "8766SS Receptacle Webpage", https://www.blickman.com/category/solution-stands/p/receptacle_0828766000, 2022, 4 pages.

Blickman, "8867SS Benjamin Mayo Stands Webpage", https://www.blickman.com/category/mayo-stands/p/benjamin_mayo_stand_0668867000, 2022, 5 pages.

English language abstract and machine-assisted English translation for CN 105640093 extracted from espacenet.com database on Jun. 10, 2020, 7 pages.

English language abstract and machine-assisted English translation for CN 106263557 extracted from espacenet.com database on Jun. 10, 2020, 4 pages.

English language abstract and machine-assisted English translation for CN 109179243 extracted from espacenet.com database on Jun. 10, 2020, 7 pages.

English language abstract and machine-assisted English translation for CN 201840835 extracted from espacenet.com database on Jun. 10, 2020, 5 pages.

English language abstract and machine-assisted English translation for CN 208470711 U extracted from espacenet. com database on Jul. 20, 2022, 10 pages.

English language abstract and machine-assisted English translation for WO 2018/014219 extracted from espacenet.com database on Jun. 10, 2020, 6 pages.

Environmental XPRT, "Wanroce-Model MCDS-Medical Waste Shredder with Sterilizer", https://www.environmental-expert.com/products/wanrooe-model-mcds-medical-waste-shredder-with-sterilizer-692369, 2022, 4 pages.

International Search Report for Application No. PCT/US2021/014284 dated Jun. 2, 2021, 3 pages.

Lomboy, Christopher, "Ideas that Work: Ergonomics-Elevate Your Bucket", Outpatient Surgery Magazine, Jan. 2016, 6 pages.

* cited by examiner

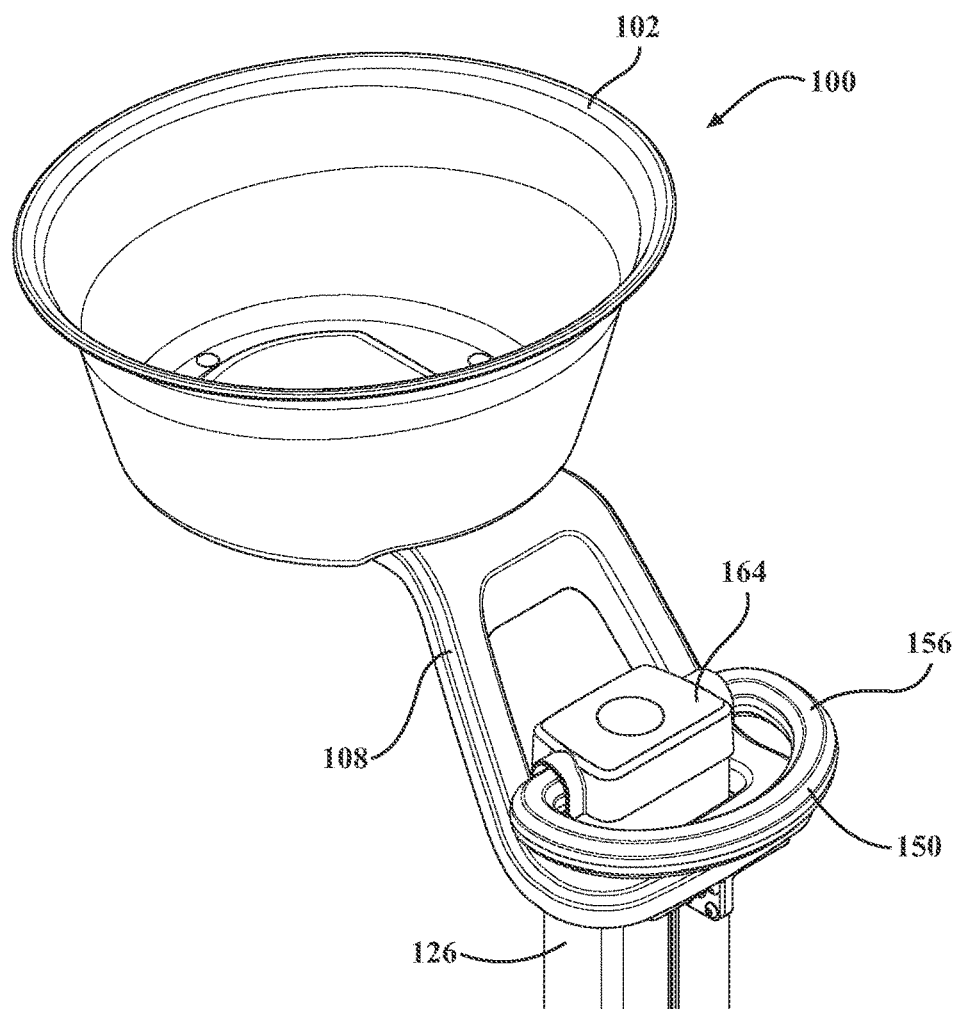
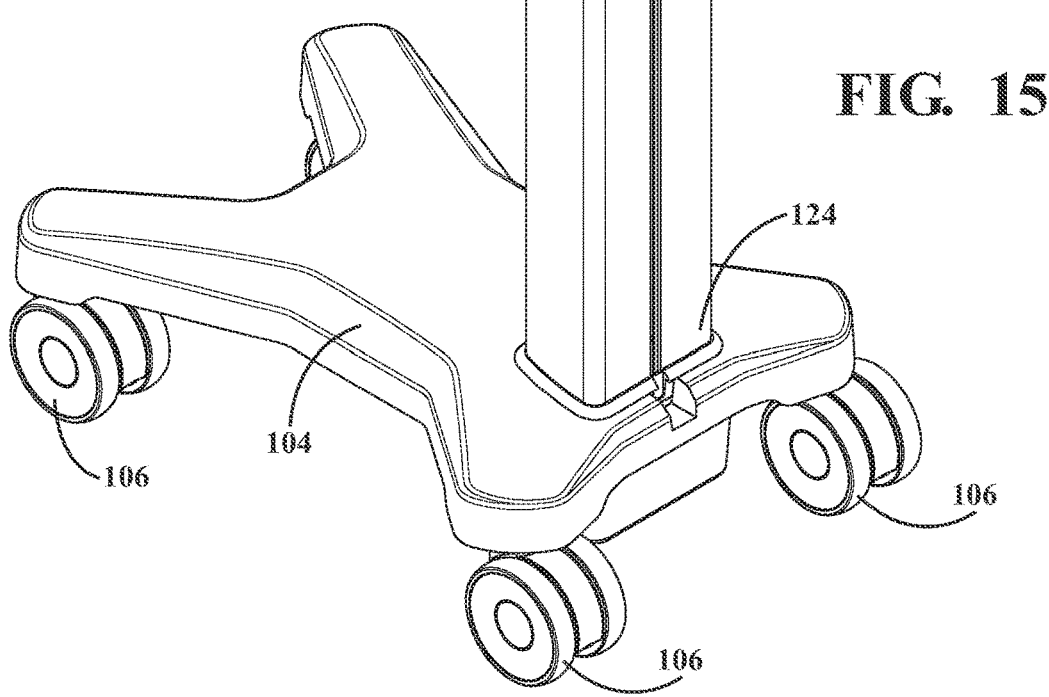
FIG. 15

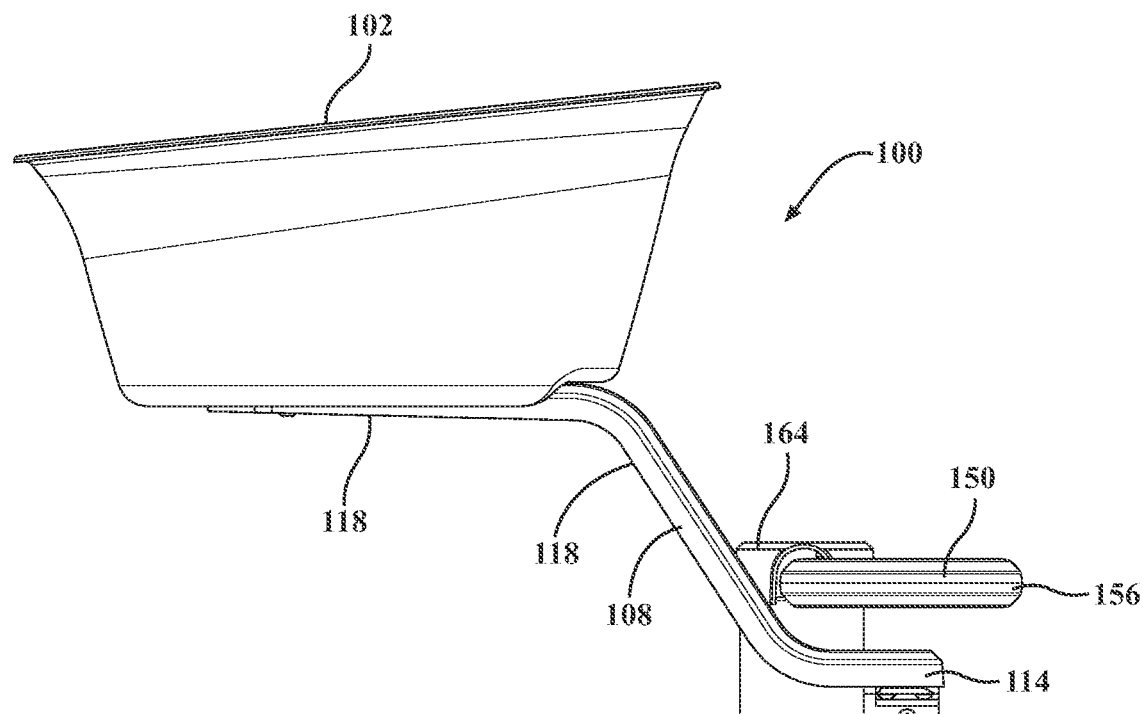
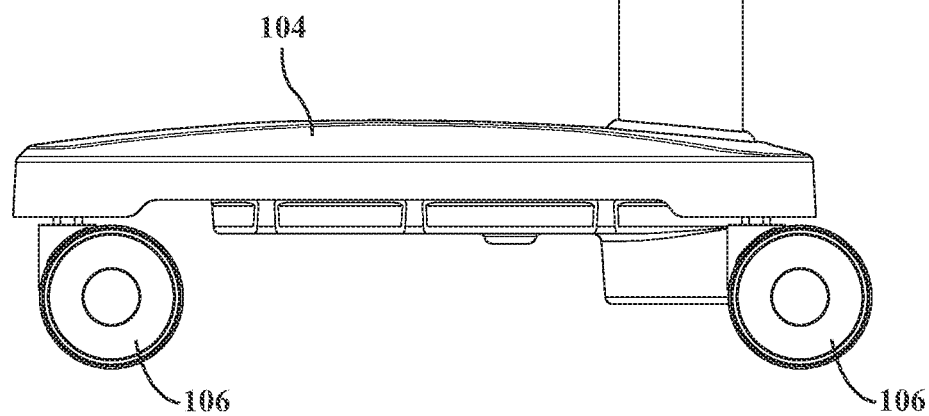
FIG. 16

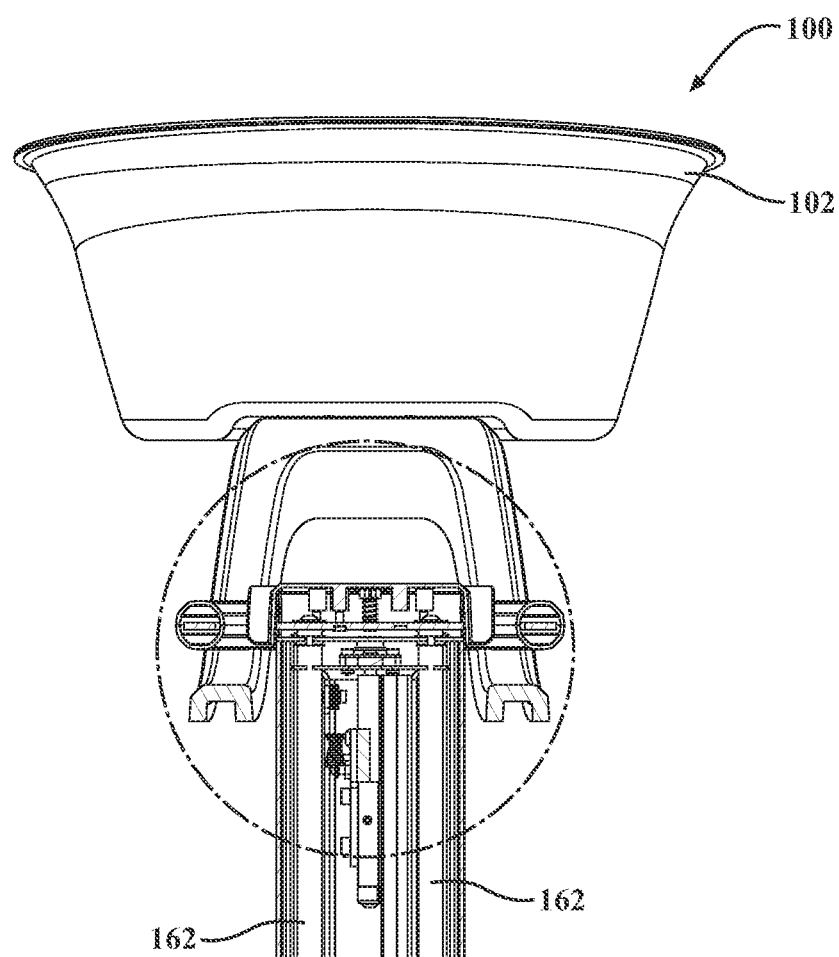
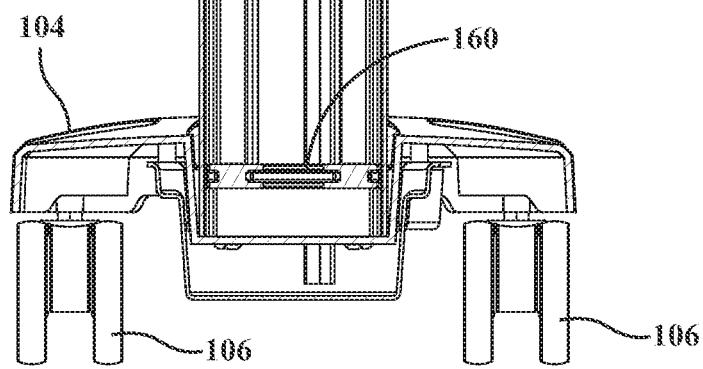
FIG. 18

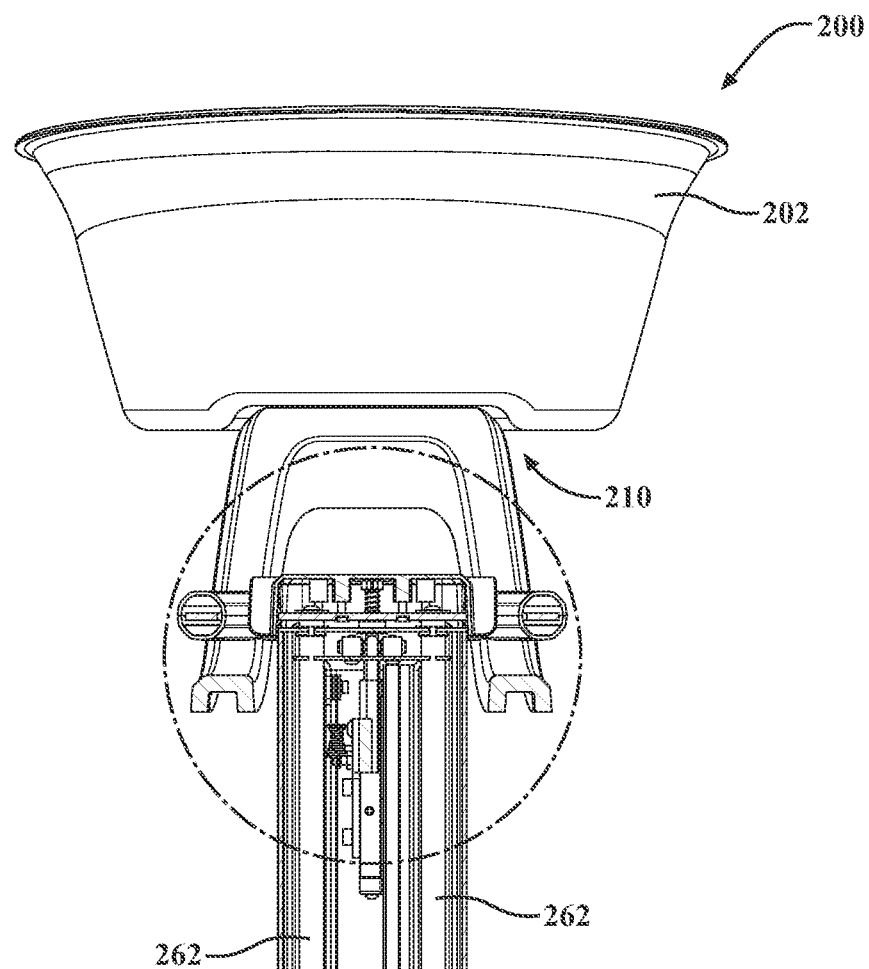
FIG. 28
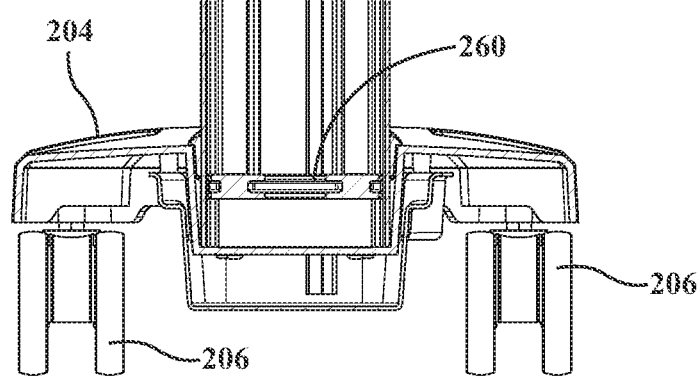

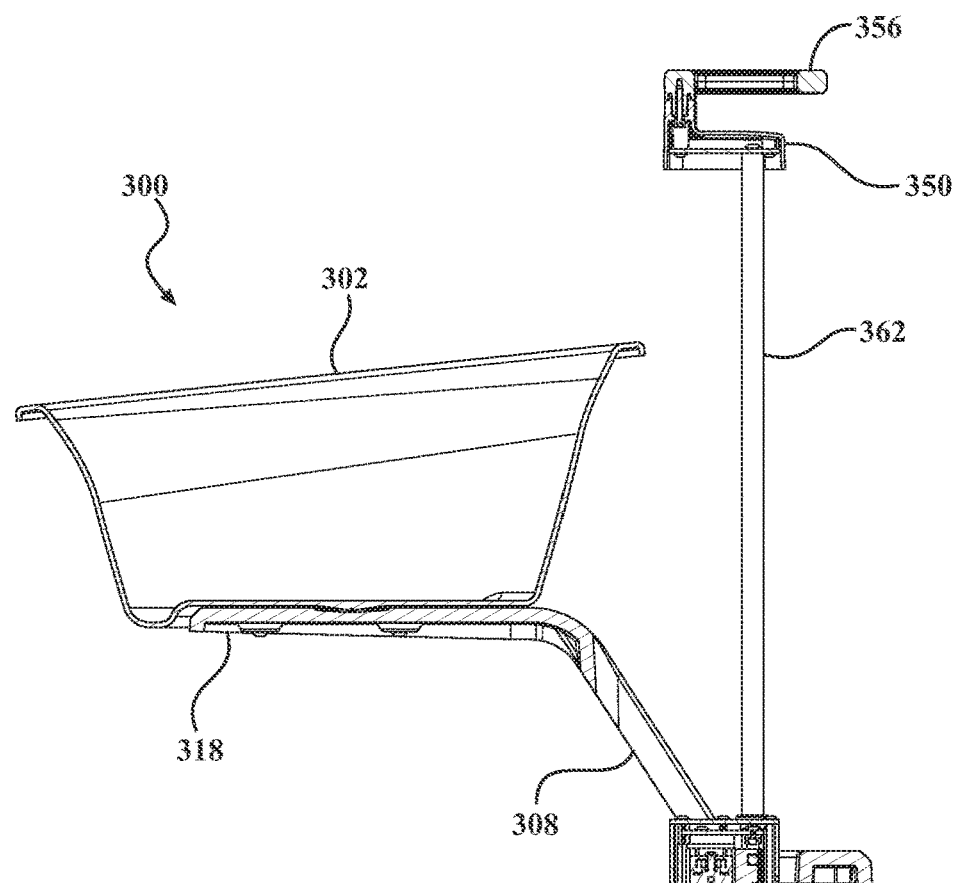
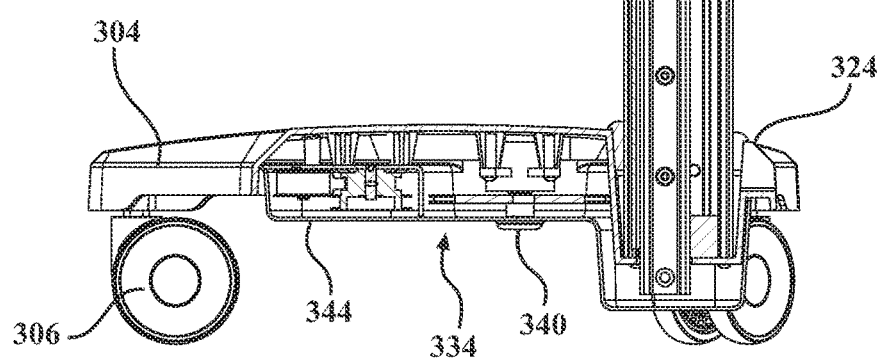
FIG. 45

HEIGHT ADJUSTABLE MEDICAL BUCKET

RELATED APPLICATIONS

This is a national entry of International Application No. PCT/US2021/014284, filed Jan. 21, 2021, which claims priority to and all the benefits of U.S. Provisional Patent Application No. 63/109,740, filed on Nov. 4, 2020, and U.S. Provisional Patent Application No. 62/963,653, filed on Jan. 21, 2020, the entire contents of each being hereby incorporated by reference.

BACKGROUND

Buckets are commonly used by healthcare professionals in operating rooms to collect surgical sponges or other objects. Some buckets commonly have a relatively low height in order to be out of (under) the sterile field hence reducing the chance of inadvertently entering the sterile field and being easy to store. Other buckets have a relatively high height in order to be more accessible during cases where a healthcare professional is primarily standing, however, these buckets lack the easy storage and opportunity to be under the sterile field during a procedure.

SUMMARY

In one example, a height-adjustable bucket is adapted to carry a medical object and the bucket includes a receptacle for carrying the medical object, a base, and a support member coupled to the base. The bucket also includes a carrier movably coupled to the support member and for supporting the receptacle. The carrier is configured to move between a relatively high position and a relatively low position along an axis defined by the support member. The bucket further includes a lifting member slidably coupled to the carrier and configured to move between a raised position and a lowered position. The lifting member includes a first end portion comprising a handle and a second end portion, opposite the first end portion, including a stop member configured to operatively engage the carrier, and a retainer selectively coupling the carrier to the support member and configured to selectively retain the carrier in the relatively high position. The lifting member is configured to be in the lowered position when the carrier is in the relatively high position and when the carrier is in the relatively low position. The stop member is spaced from the carrier when the lifting member is in the lowered position and when the carrier is in the relatively high position.

In another example, a height-adjustable stand includes a medical device to be supported, a base, a support member coupled to the base, and a carrier movably coupled to the support member and for supporting the receptacle. The carrier is configured to move between a relatively high position and a relatively low position along an axis defined by the support member. The stand also includes a lifting member slidably coupled to the carrier and configured to move between a raised position and a lowered position. The lifting member includes a first end portion comprising a handle, and a second end portion, opposite the first end portion, including a stop member configured to operatively engage the carrier. The lifting member also includes a retainer selectively coupling the carrier to the support member and configured to selectively retain the carrier in the relatively high position. The lifting member is configured to be in the lowered position when the carrier is in the relatively high position and when the carrier is in the relatively low position. The stop member is spaced from the carrier when the lifting member is in the lowered position and when the carrier is in the relatively high position.

In yet another example a height-adjustable bucket adapted to carry a medical object, includes a receptacle for carrying the medical object, a base, a support member coupled to the base, and a carrier movably coupled to the support member and the carrier for supporting the receptacle. The carrier is configured to move between a relatively high position and a relatively low position along an axis defined by the support member. The bucket also includes a retainer selectively coupling the carrier to the support member and configured to selectively retain the carrier in the relatively high position. When the carrier is in the relatively high position and the retainer is coupling the carrier to the support member, the carrier and the retainer are configured to automatically decouple from one another when contents of the receptacle has a mass greater than a predetermined mass.

In another example, a height-adjustable medical stand includes a medical device to be supported, a base, a support member coupled to the base, a carrier movably coupled to the support member and the carrier for supporting the receptacle. The carrier is configured to move between a relatively high position and a relatively low position along an axis defined by the support member. The stand also includes a retainer selectively coupling the carrier to the support member and configured to selectively retain the carrier in the relatively high position. When the carrier is in the relatively high position and the retainer is coupling the carrier to the support member, the carrier and the retainer are configured to automatically decouple from one another when contents of the receptacle has a mass greater than a predetermined mass.

In yet another example, a height-adjustable bucket adapted to carry a medical object includes a receptacle for carrying the medical object, a base, a support member coupled to the base, and a carrier movably coupled to the support member and for supporting the receptacle. The carrier is configured to move between a relatively high position and a relatively low position along an axis relative to the relatively high position. The bucket also includes a retainer selectively coupling the carrier and the support member and configured to retain the carrier in the relatively high position. Additionally, the bucket includes a lifting member coupled to the carrier and comprising a first end portion defining an exterior engagement surface, and an engagement member. The exterior engagement surface is configured to be activated by the user and the engagement member is configured to be moved from a first position to a second position upon activation of the exterior engagement surface. Additionally, the support member defines an interior engagement surface configured to be actuated by movement of the engagement member into the second position. The support member also comprises a piston configured to selectively uncouple the carrier and the support member to allow the carrier to move to the relatively low position upon actuation of the interior engagement surface by the engagement member.

In yet another example, a height-adjustable stand includes a medical device to be supported, a base, a support member coupled to the base, and a carrier movably coupled to the support member and for supporting the receptacle. The carrier is configured to move between a relatively high position and a relatively low position along an axis relative to the relatively high position. The stand also includes a retainer selectively coupling the carrier and the support member and configured to retain the carrier in the relatively high position, and a lifting member coupled to the carrier and comprising a first end portion comprising an exterior engagement surface, and an engagement member. The exterior engagement surface is configured to be activated by the user and the engagement member is configured to be moved from a first position to a second position upon activation of the exterior engagement surface. The support member defines an interior engagement surface configured to be actuated by movement of the engagement member into the second position. The support member comprises a piston configured to selectively uncouple the carrier and the support member to allow the carrier to move to the relatively low position upon actuation of the interior engagement surface by the engagement member.

In yet another example, a height-adjustable stand adapted to carry a medical object includes a medical device to be supported, a base having an upper most surface, a support member coupled to the base, and a carrier movably coupled to the support member and for supporting the medical device. The carrier is configured to move between a relatively high position and a relatively low position along an axis defined by the support member. The stand also includes a retainer selectively coupling the carrier to the support member and configured to selectively retain the carrier in the relatively high position and a dampening assembly configured to provide controlled movement of the carrier along a length of the axis defined between the relatively high position and the relatively low position. The dampening assembly includes a tension member coupled to the carrier, a dampener coupled to the base and positioned below the upper most surface of the base the dampener coupled to the tension member, and a pulley configured to change direction of the tension member between the carrier and the dampener.

In yet another embodiment, a height-adjustable stand adapted to carry a medical object includes a medical device to be supported, a base, a support member coupled to the base, and a carrier movably coupled to the support member and for supporting the medical device. The carrier is configured to move between a relatively high position and a relatively low position along an axis defined by the support member. The stand also includes a retainer selectively coupling the carrier to the support member and configured to selectively retain the carrier in the relatively high position, and a dampening assembly configured to provide controlled movement of the carrier along the axis. The dampening assembly includes a tension member coupled to the carrier and a radial dampener operably coupled to the tension member and configured to provide controlled movement of the carrier along the axis.

In yet another embodiment a height-adjustable medical stand adapted to carry a medical object includes a receptacle for carrying the medical object having a bottommost surface, a base and a support member coupled to the base. The stand also includes a carrier movably coupled to the support member for supporting a medical device. The carrier is configured to move the receptacle between a minimum height of the bottommost surface and a maximum height of the bottommost surface along an axis defined by the support member. The maximum height of the bottommost surface of the receptacle is at least two times greater than the minimum height of the bottommost surface of the receptacle.

BRIEF DESCRIPTION OF THE DRAWINGS

Referring now to the drawings, exemplary illustrations are shown in detail. Although the drawings represent examples, the drawings are not necessarily to scale, and certain features may be exaggerated or schematic in form to better illustrate and explain a particular aspect of an illustrative example. Any one or more of these aspects can be used alone or in combination with one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows:

FIG. 15 is a rear perspective view of the bucket having the receptacle in the maximum height and having the lifting member in the lowered position.

FIG. 16 is a side view of the bucket having the receptacle in the maximum height and having the lifting member in the lowered position.

FIG. 18 is a sectional rear view of the bucket having the receptacle in the maximum height and having the lifting member in the lowered position.

FIG. 23 is a sectional side view of the bucket of FIG. 21 having the receptacle in the maximum height and having the lifting member in a raised position.

FIG. 28 is a sectional rear view of the bucket of FIG. 21 having the receptacle in the maximum height and having the lifting member in the lowered position.

FIG. 45 is a sectional side view of the bucket having the receptacle in the maximum height having the lifting member in a raised position.

DETAILED DESCRIPTION

Figure 1:
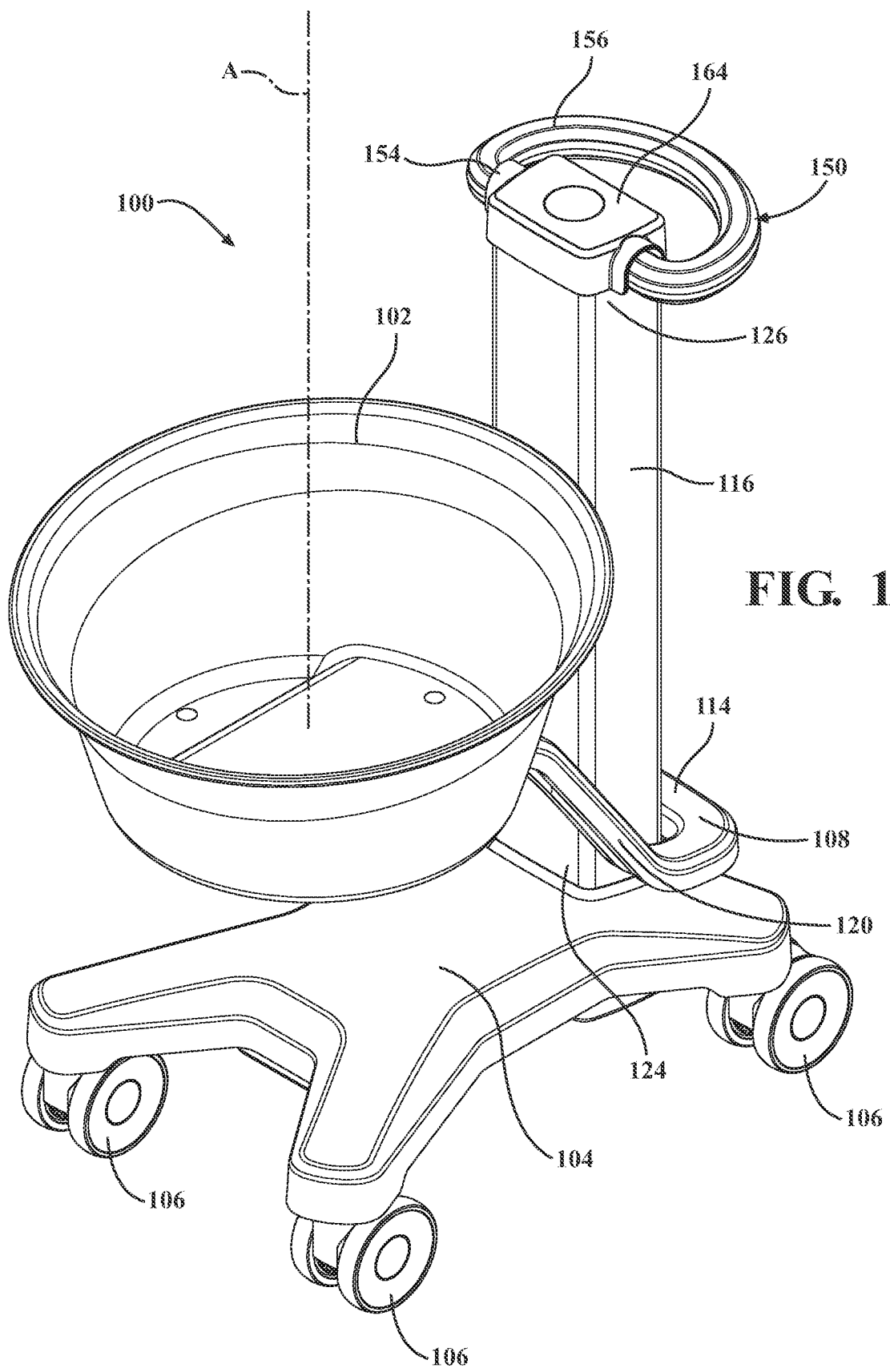
FIG. 1 is a perspective view of a bucket having a receptacle in a minimum height.

Referring to FIGS. 1-20, a height-adjustable bucket 100 or stand for collection of objects is provided. The bucket 100 often includes a receptacle 102 adapted to carry a medical object. In one example, the medical object may include surgical sponges. The receptacle 102 may be a basin. Alternatively, the receptacle 102 may be replaced with other devices to be supported, such as a table, tray, etc. In the example shown in FIG. 1, the receptacle 102 is generally round and has a sidewall configured to prevent liquids splashing out of the receptacle 102 during use. The receptacle 102 is also typically comprised of a metal such as steel or aluminum and includes a smooth surface for ease of cleaning in between uses. In the example illustrated in FIG. 1, the receptacle 102 is comprised of stainless steel and is produced by stamping. However, it is also contemplated that the receptacle 102 may be produced by another method, another material, and/or may be any shape and size. In one example, the receptacle has a depth of approximately 4-8", 4-6" or 5". The receptacle 102 may also include a bottommost surface configured to be moved between a maximum height of the bottommost surface and a minimum height of the bottommost surface. In one example, the maximum height of the bottommost surface is at least two times the minimum height of the bottommost surface.

The bucket 100 also includes a base 104 comprising one or more wheels 106 to facilitate movement across a floor surface. In one example, the wheels 106 includes casters and allow the base 104 to be lifted from the floor. In one example, the casters and wheels 106 lift the base 104 off of the floor by approximately 2-6", 3-5", or 4". In the example shown in FIG. 1, the base 104 may be comprised of stainless steel and includes a plurality of legs extending from a center location with each leg including a wheel. However, the base 104 may be of any shape and size and comprised of any material. Moreover, the bucket 100 is configured such that each of the surfaces of the base 104 are visible and accessible for cleaning regardless of the position of the receptacle 102.

Some healthcare professionals prefer to use a bucket having a maximum height receptacle for some procedures and a bucket having a minimum height receptacle for other procedures as each has advantages. For example, the receptacle at the minimum height has the advantages of being easier to store and being more accessible during cases where the healthcare professional is primarily sitting. A receptacle at the maximum height on the other hand, has the advantages of being more ergonomic during retrieving/counting-out process, being more accessible during cases where the healthcare professional is primarily standing, and allowing the receptacle to be seen and more easily used when the receptacle is on the opposite side of a table. Additionally, some operating rooms include air filtration systems which blow sterile air through the sterile field. Having a bucket which is below the sterile field prevents potential contamination of the sterile air flow from the bucket and its contents.

A height-adjustable bucket 100 enables a single product that has all these advantages in one system. The adjustable height bucket 100 has the ability to adjust the vertical position of the receptacle 102 between a maximum height (having a height that is at least 700 mm, 800 mm, 900 mm, or 1000 mm" height) and a minimum height (having a height that is less than 600 mm, 500 mm, 450 mm, or 400 mm height).

The bucket 100 includes a carrier 108 for supporting the receptacle 102. The carrier 108 is configured to move between a relatively high position (FIGS. 8-18) and a relatively low position (FIGS. 1-7) along a vertical axis A relative to the relatively high position (FIGS. 8-18). As described herein, the carrier 108 being in the relatively high position (FIGS. 8-18) corresponds with the receptacle 102 being in the maximum height and the carrier 108 being in the relatively low position (FIGS. 1-7) corresponds with the receptacle 102 being in the minimum height.

Figure 2:
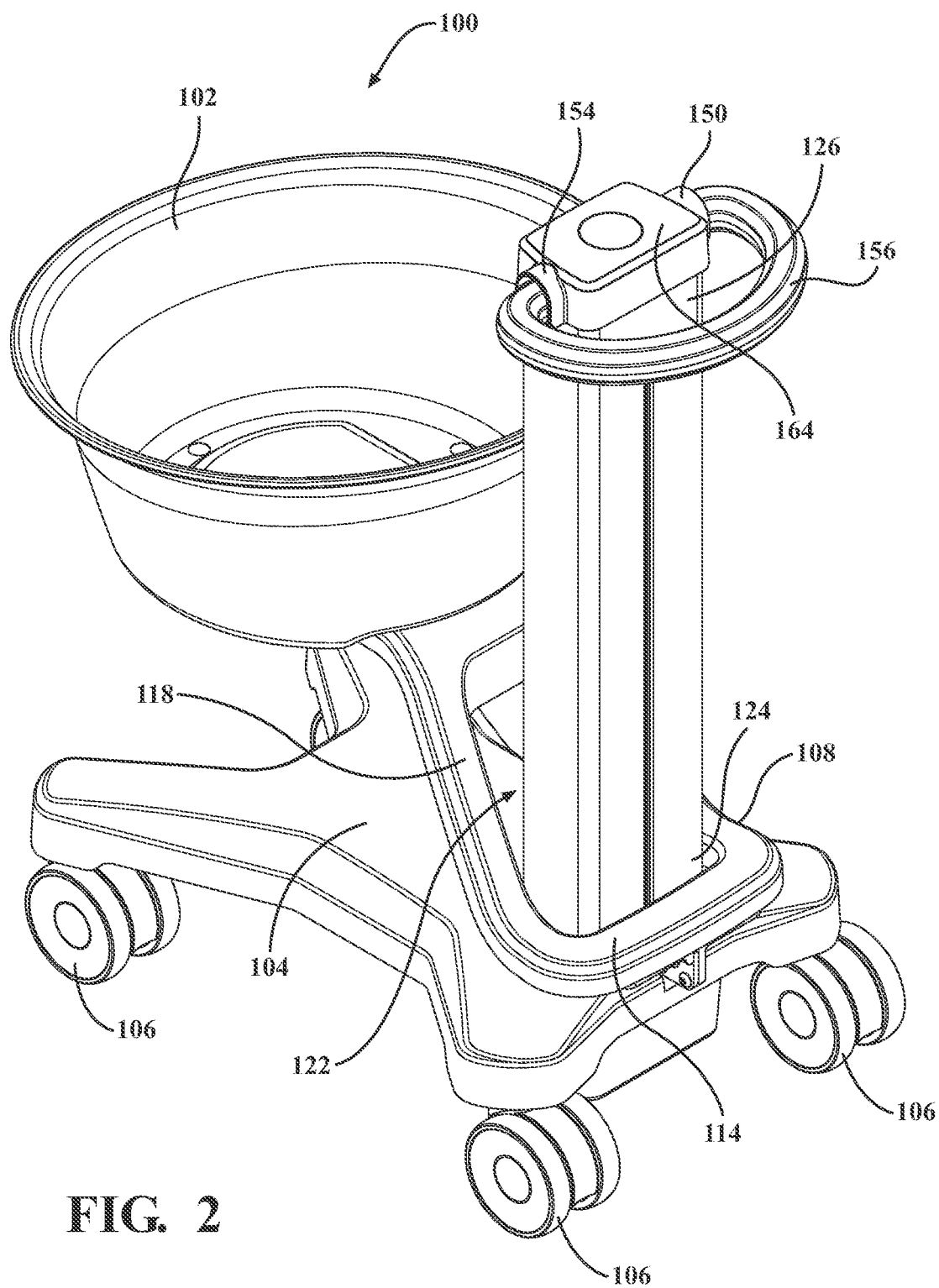
FIG. 2 is a rear perspective view of the bucket having the receptacle in the minimum height.
Figure 3:
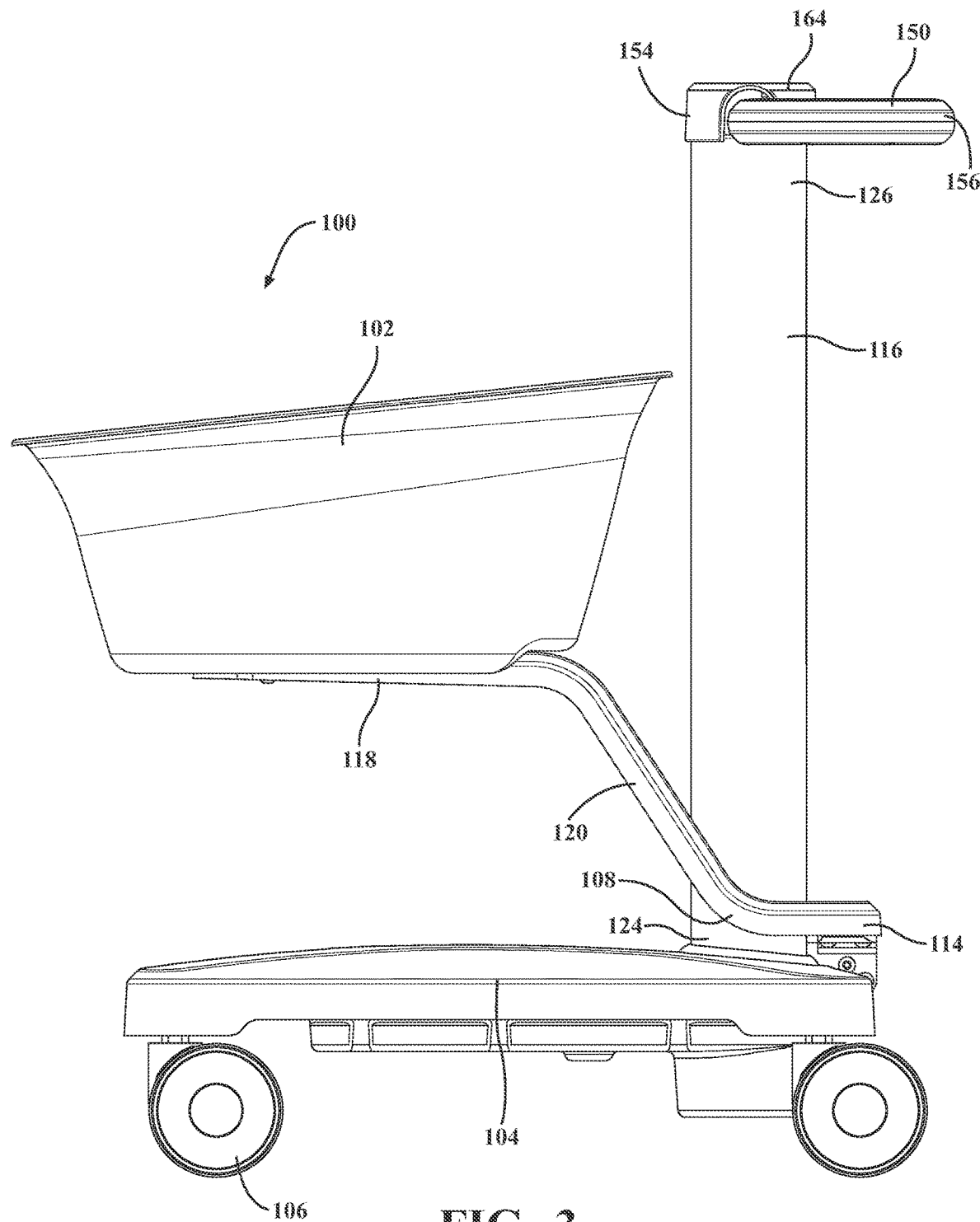
FIG. 3 is a side view of the bucket having the receptacle in the minimum height and having a lifting member in a lowered position.
Figure 4:
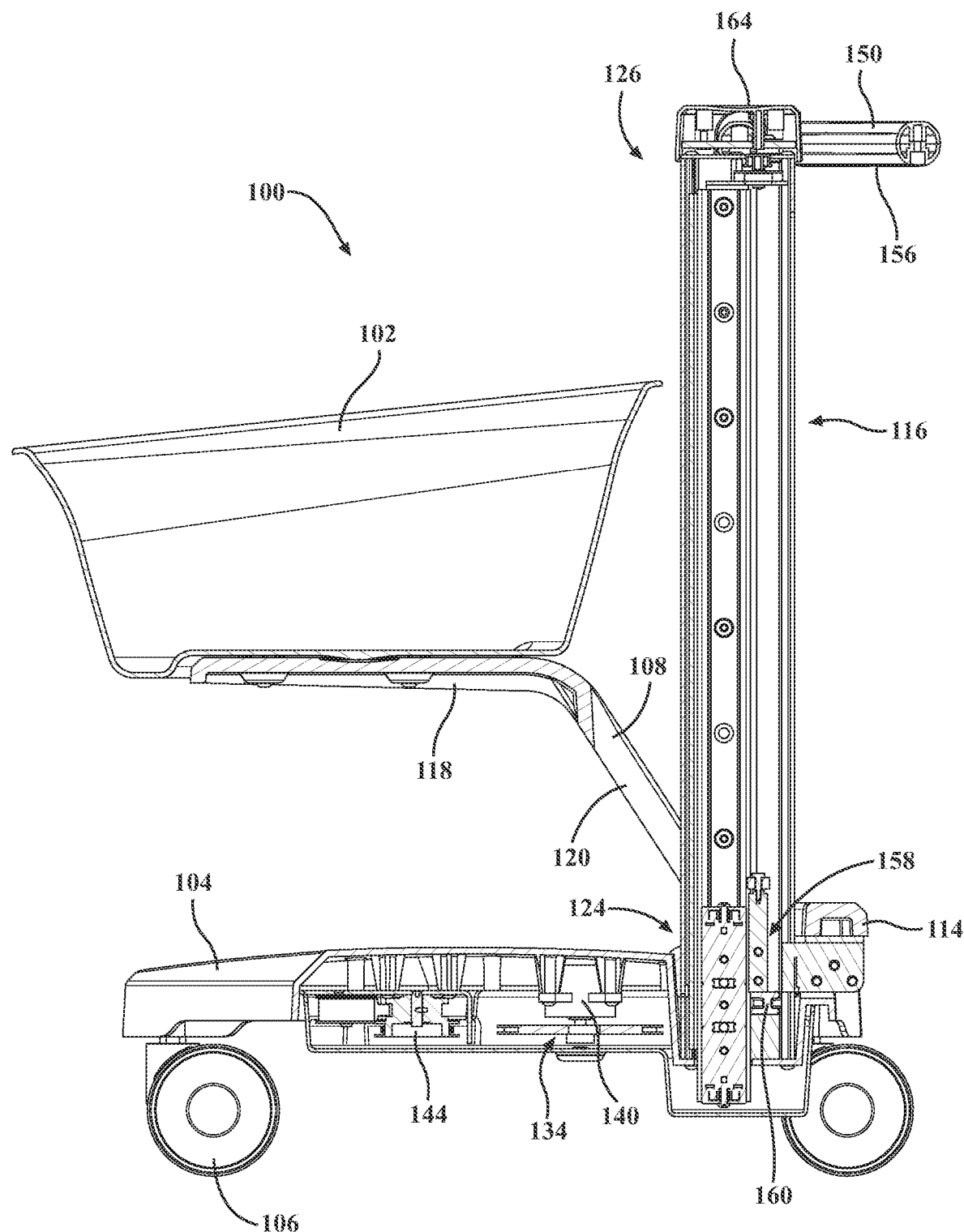
FIG. 4 is a sectional side view of the bucket having the receptacle in the minimum height and having the lifting member in the lowered position.
Figure 5:
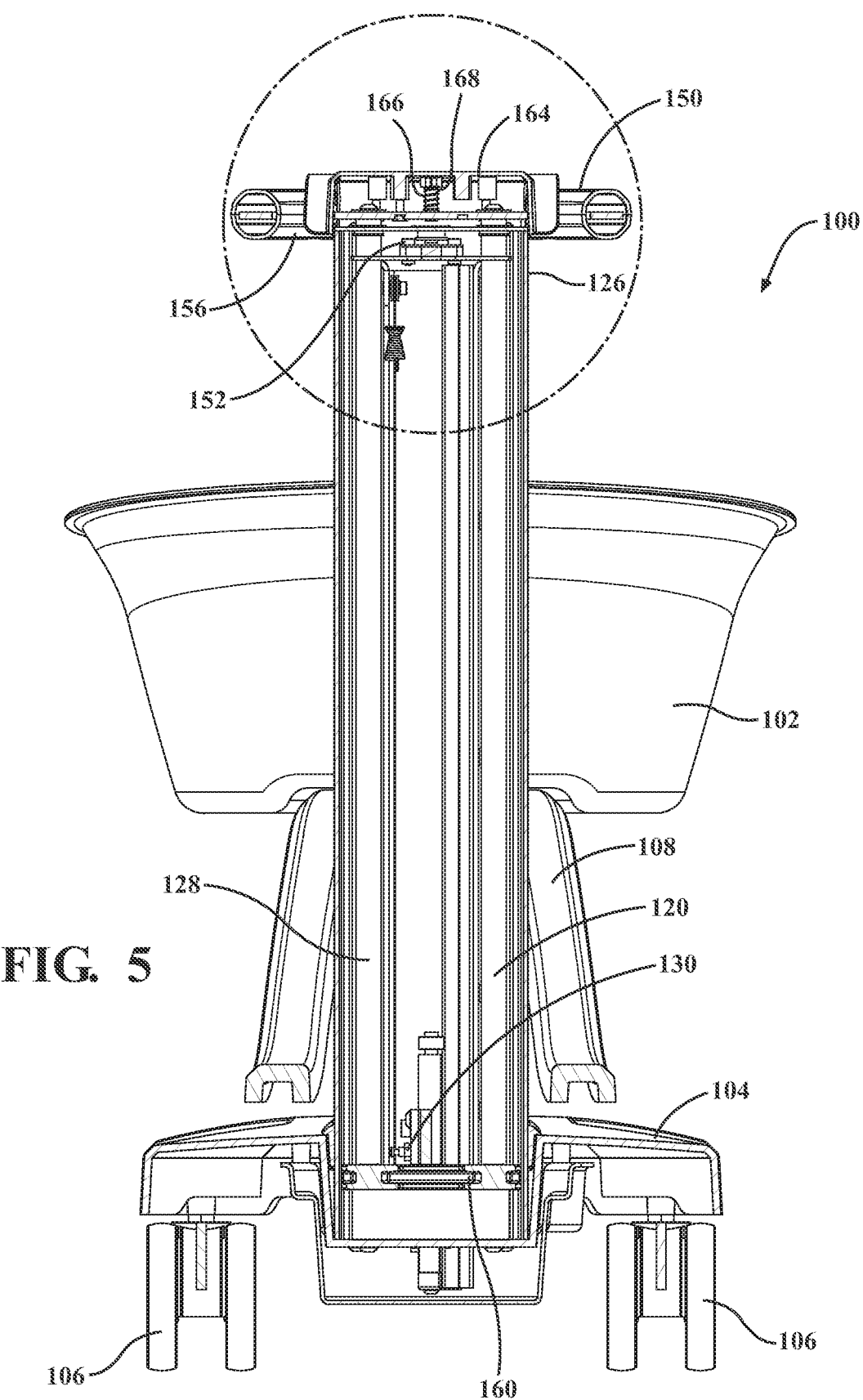
FIG. 5 is a sectional rear view of the bucket having the receptable in the minimum height and having the lifting member in the lowered position.

In the example shown in FIGS. 1 and 2, the carrier 108 has a lower portion 114 coupled to a support member 116 of the bucket 100 and an upper portion 118 coupled to the receptacle 102. As best shown in FIG. 3 the carrier 108 has a step-up form between the lower portion 114 and the upper portion 118. In other words, the carrier 108 includes an angled portion 120 which couples the lower portion 114 of the carrier 108 with the upper portion 118 of the carrier 108. The angled portion 120 allows the receptacle 102 to be moved between the minimum height and the maximum height while maintaining an open, easy to clean design. The lower portion 114 of the carrier 108 also defines a first aperture 122 disposed therethrough. The first aperture 122 is configured is allow the support member 116 to be disposed therethrough, yet still providing excellent rigidity. The upper portion 118 of the carrier 108 may be coupled to the receptacle 102 by any coupling method including, but not limited to, welding, gluing, or a plurality of fasteners. In the example illustrated in FIG. 3, the upper portion 118 of the carrier 108 is an attachment arm configured to be attached to an inset portion on an underside of the receptacle 102.

Referring still to FIG. 1, the support member 116 includes a lower end portion 124 and an opposite upper end portion 126. The support member 116 is coupled to the base 104 at the lower end portion 124 of the support member 116 and extends vertically to the upper end portion 126. Moreover, when the receptacle 102 is in the minimum height, the carrier 108 is in the relatively low position (FIGS. 1-7) and disposed adjacent to the base 104. Conversely, when the receptacle 102 is in the maximum height, the carrier 108 is in the relatively high position (FIGS. 8-18) and the carrier 108 is disposed adjacent to the upper end portion 126 of the support member 116.

As briefly described above, and as illustrated in FIG. 1, the support member 116 is coupled to the base 104 at a lower end portion 124 and extends therefrom to an upper end portion 126 along the axis A. The support member 116 also includes a rail 128 and a carriage assembly 130 and is configured to assist the movement of the carrier 108 between the relatively high position (FIGS. 8-18) and the relatively low position (FIGS. 1-7). More specifically, the support member 116 defines the rail 128 and the carrier 108 includes the carriage assembly 130 movably coupled to the rail 128. The support member 116 is sized such that when the receptacle 102 is in the minimum height, the upper end portion 126 of the support member 116 extends at a height greater than the height of the receptacle 102. Similarly, when the receptacle 102 is in the maximum height, the receptacle 102 is higher than the support member 116 such that the height of the receptacle 102 is greater than the height of the support member 116.

Figure 6:
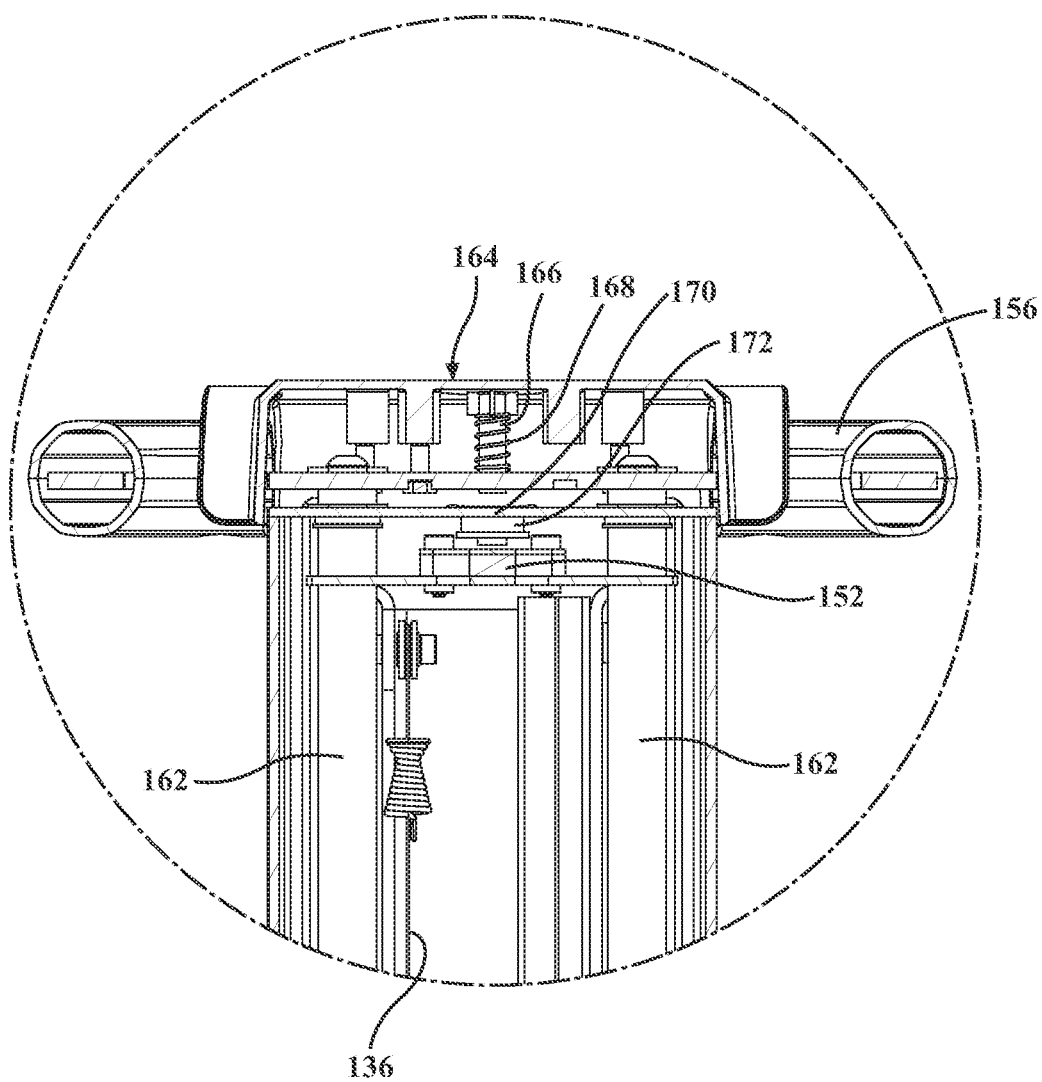
FIG. 6 is a magnified portion of FIG. 5.
Figure 13:
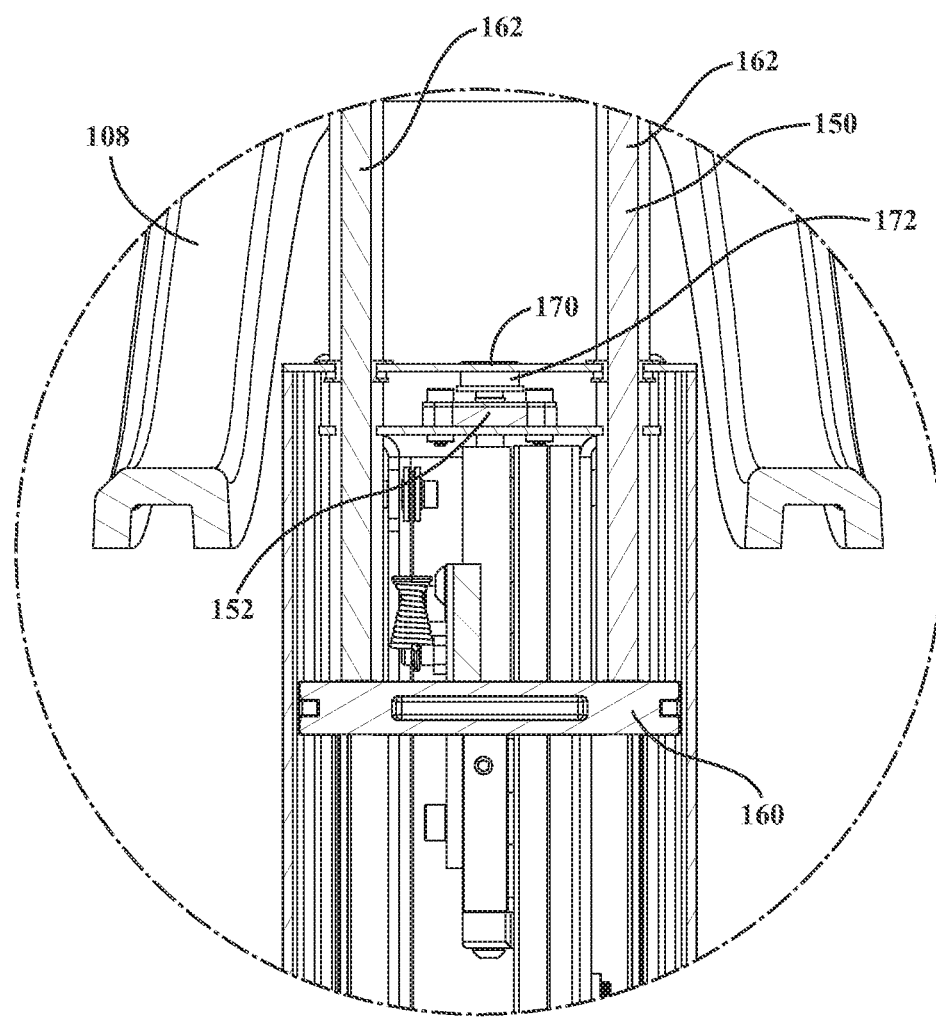
FIG. 13 is a magnified view of a portion of FIG. 12.
Figure 14:
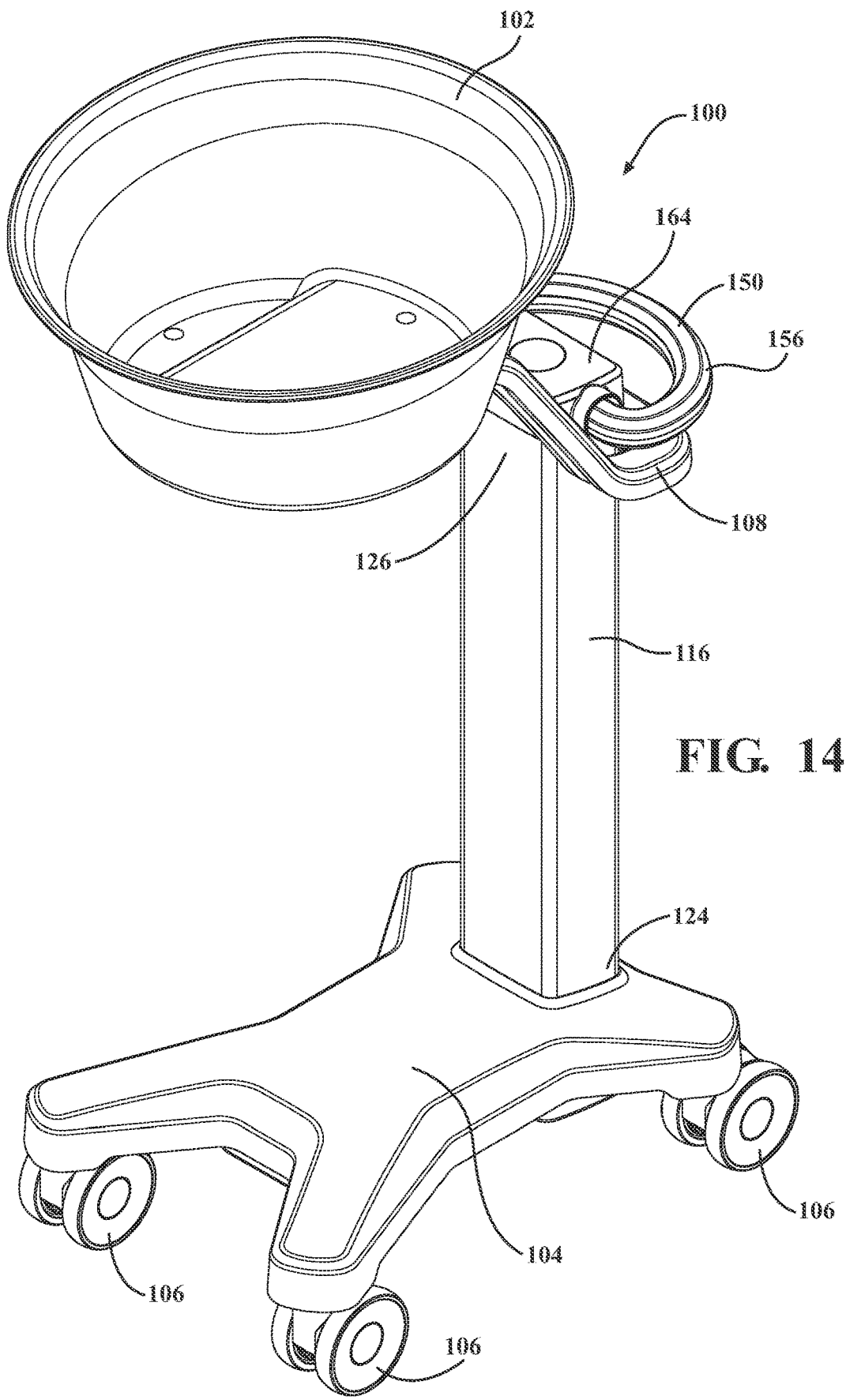
FIG. 14 is a front perspective view of the bucket having the receptacle in the maximum height and having the lifting member in the lowered position.

As best illustrated in FIGS. 6, 13, and 18, the bucket 100 also includes a retainer assembly including a retainer 152 for selectively coupling the carrier 108 and the support member 116. The retainer 152 is configured to retain the carrier 108 in the relatively high position (FIGS. 8-18). In one example, the retainer 152 and the carrier 108 are magnetically coupled to one another in the relatively high position (FIGS. 8-18). In the example shown in FIG. 1, the retainer 152 includes a first coupling member and the carrier 108 includes a second coupling member and at least one of the first coupling member and the second coupling member comprise magnetic material such that a magnetic force retains the carrier in the relatively high position. More specifically, in the example shown in FIG. 6, the first coupling member is a first magnetic element 131 disposed on the retainer and the second coupling member is a second magnetic element 133 disposed on the carrier 108. One or more of the first magnetic element 131 and the second magnetic element 133 may be comprised of magnetic material such that the first magnetic element 131 and the second magnetic element 133 are configured to be magnetically coupled to one another when the carrier 108 is in the relatively high position. Various other retaining mechanisms which retain the carrier in the relatively high position have also been contemplated.

Figure 7:
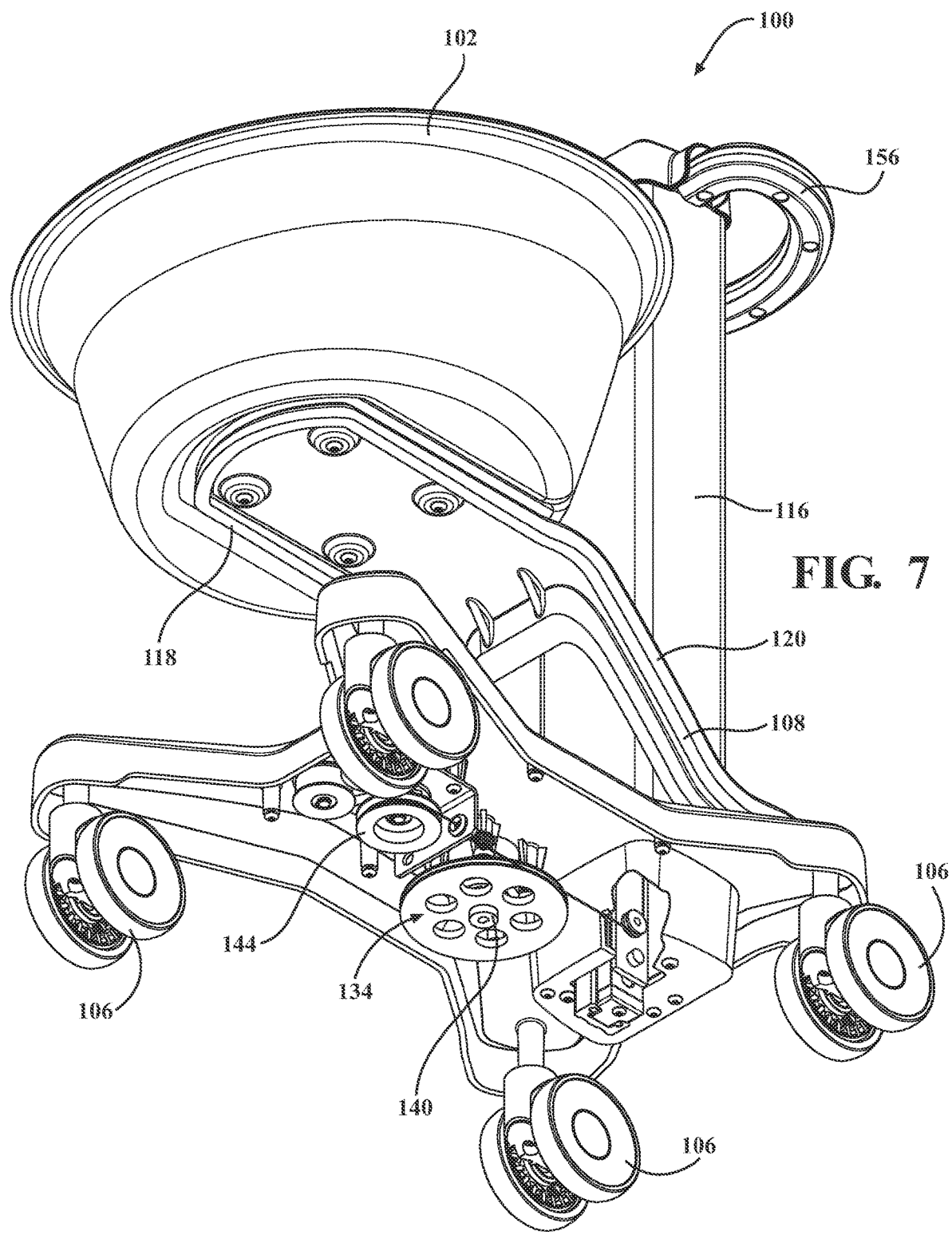
FIG. 7 is a front perspective view of the underside of the bucket having the receptacle in the minimum height and having the lifting member in the lowered position.
Figure 8:
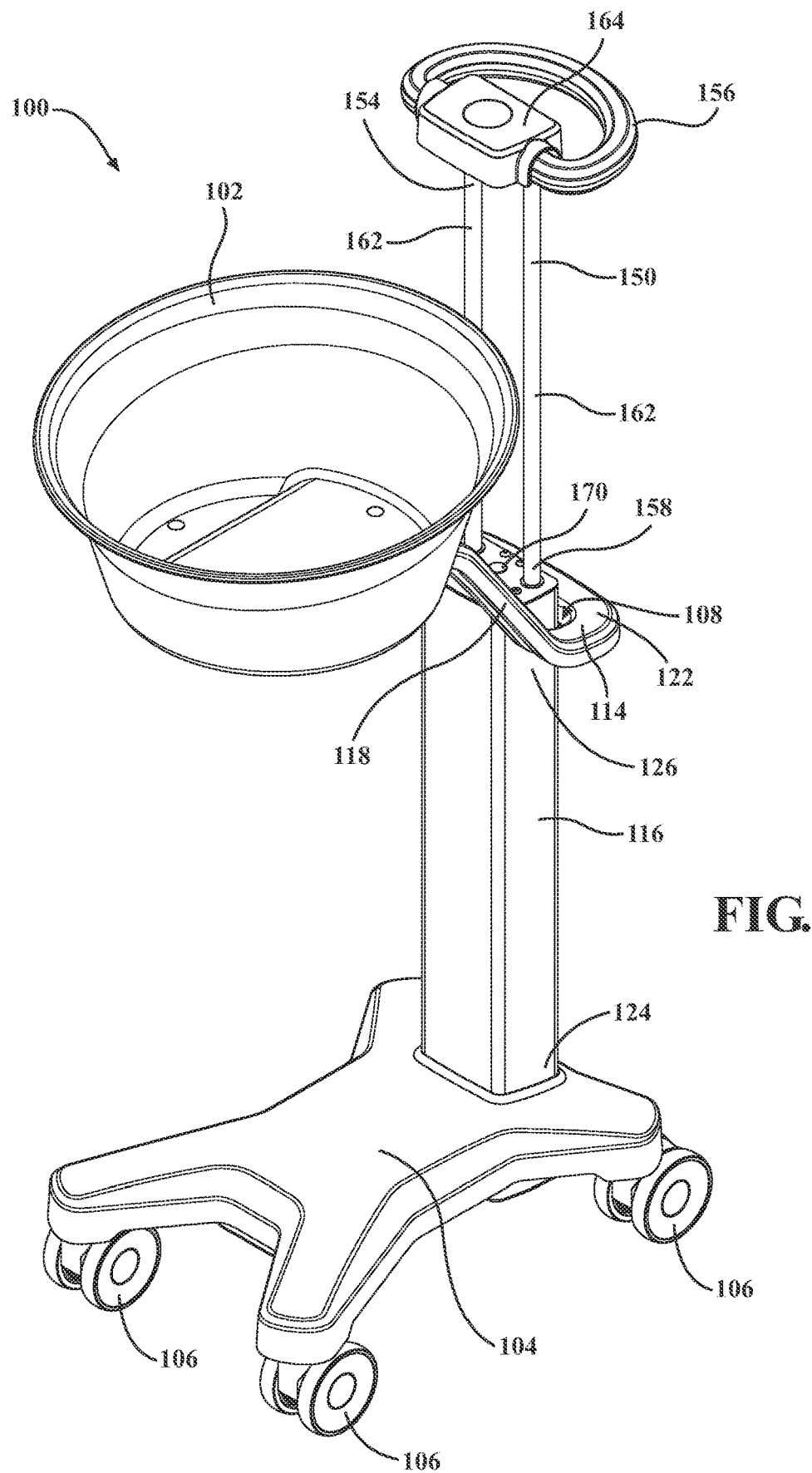
FIG. 8 is a front perspective view of the bucket having the receptacle in a maximum height and having the lifting member in a raised position.
Figure 9:
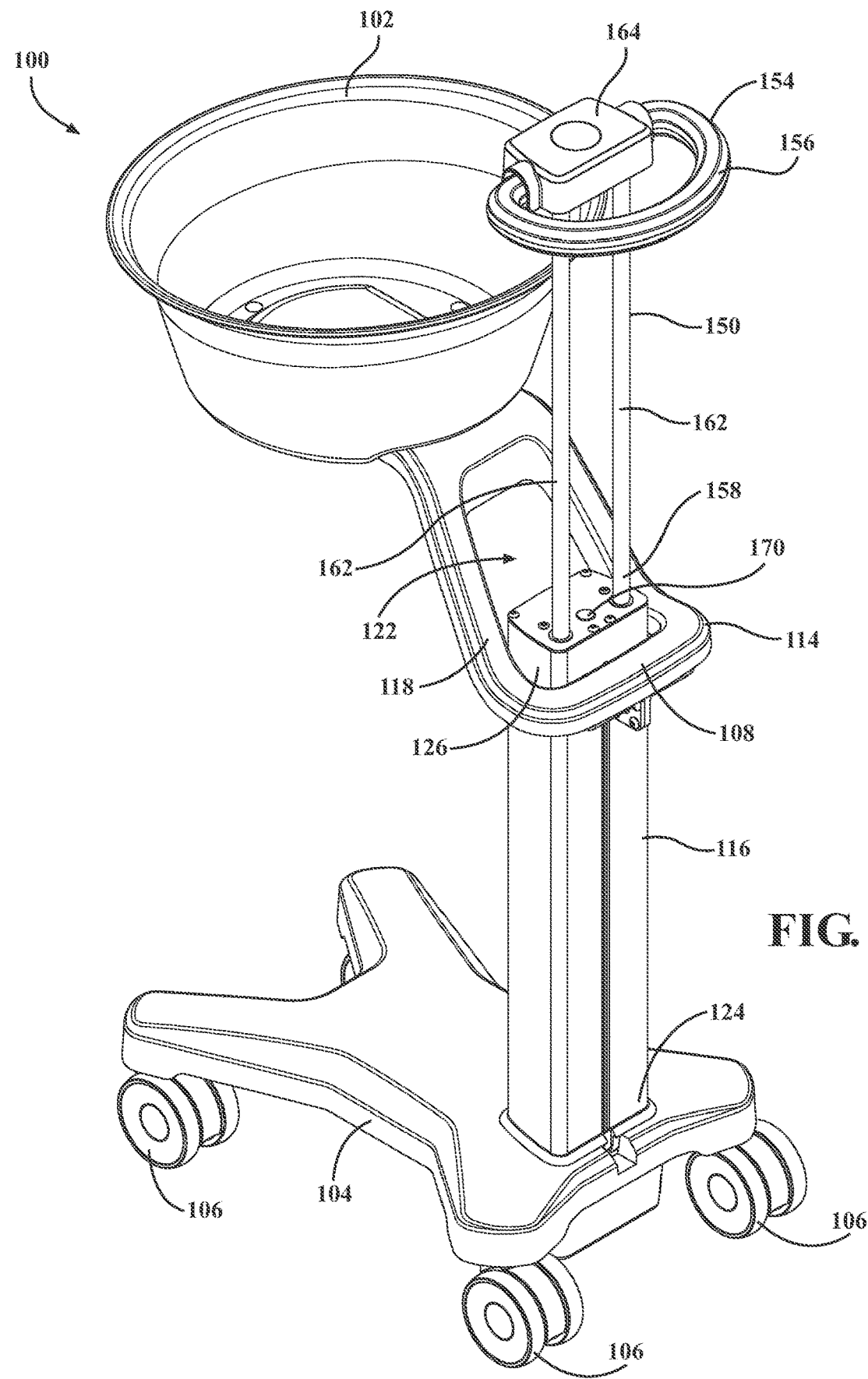
FIG. 9 is a rear perspective view of the bucket having the receptacle in the maximum height and having the lifting member in a raised position.
Figure 10:
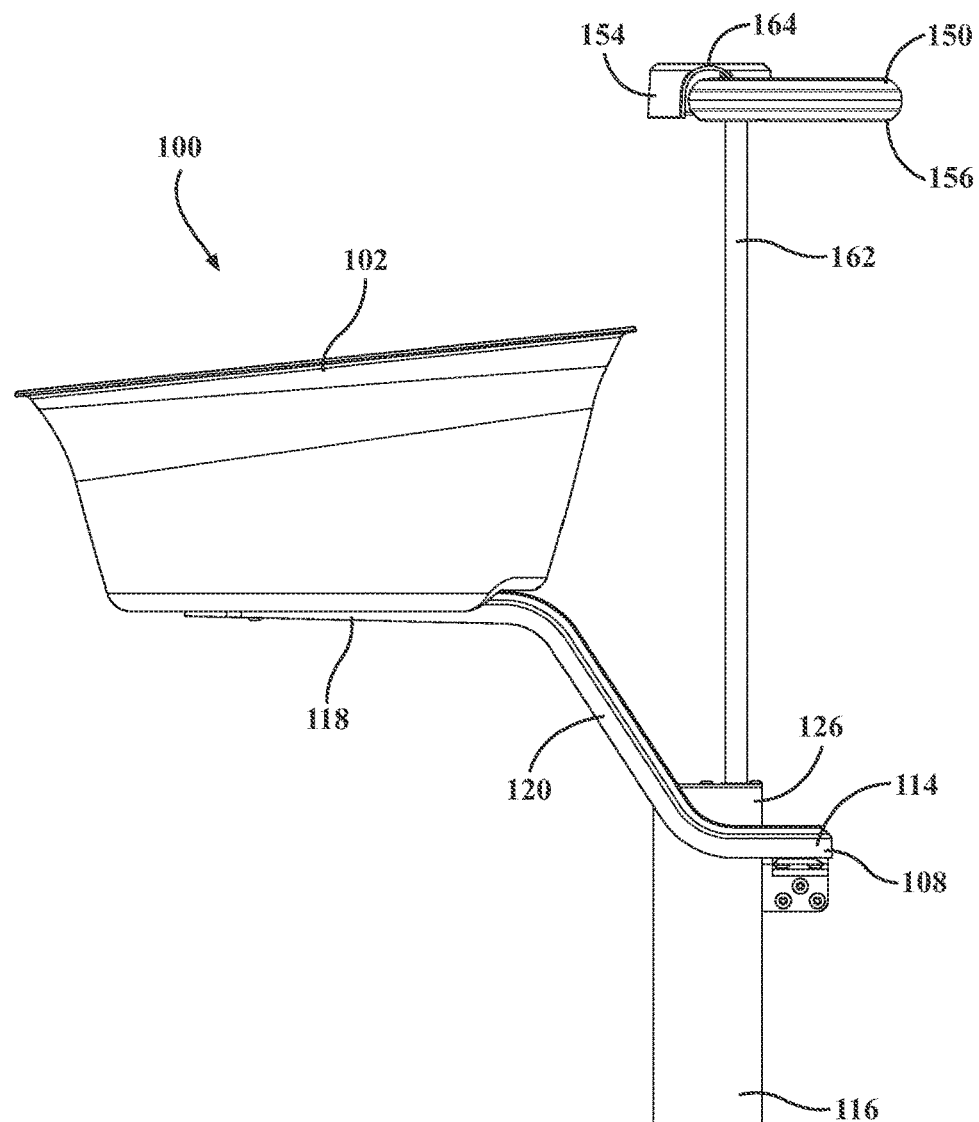
FIG. 10 is a side view of the bucket having the receptacle in the maximum height and having the lifting member in a raised position.
Figure 11:
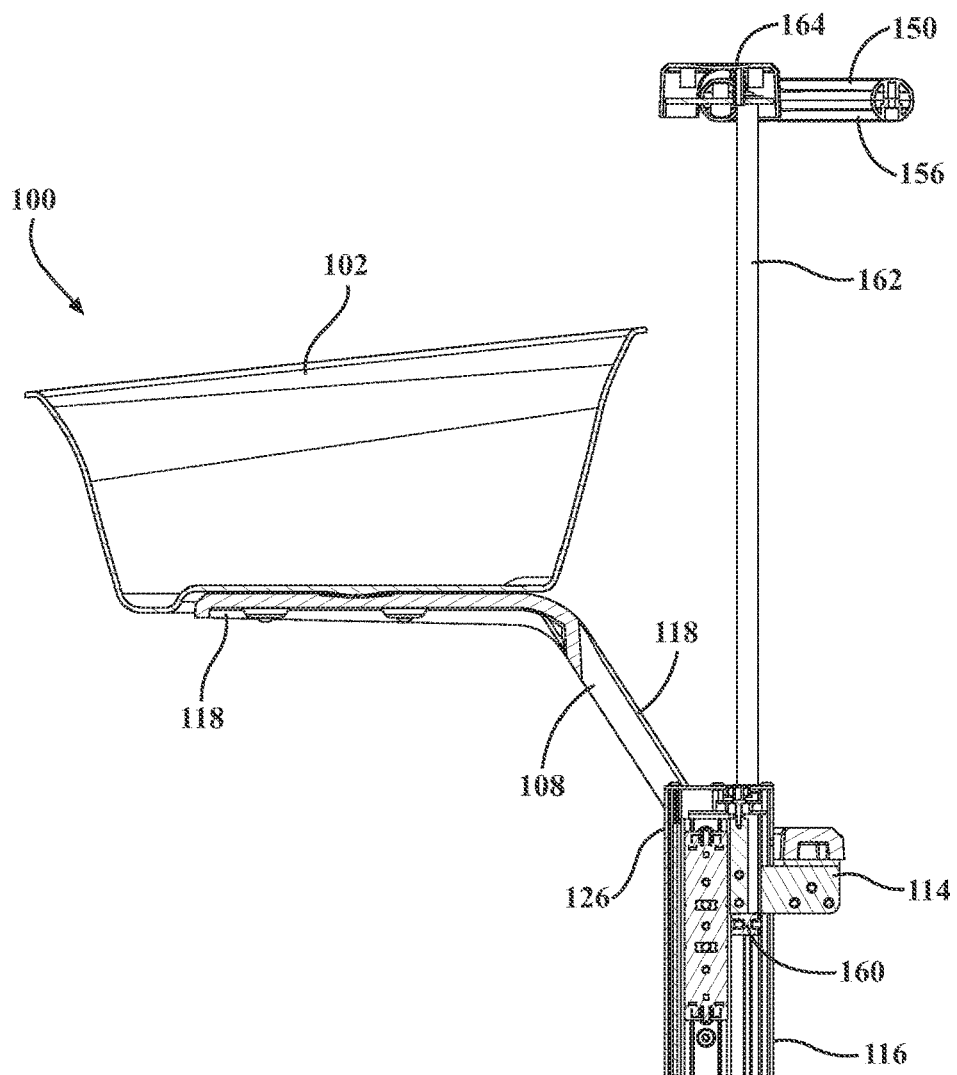
FIG. 11 is a sectional side view of the bucket having the receptacle in the maximum height having the lifting member in a raised position.
Figure 12:
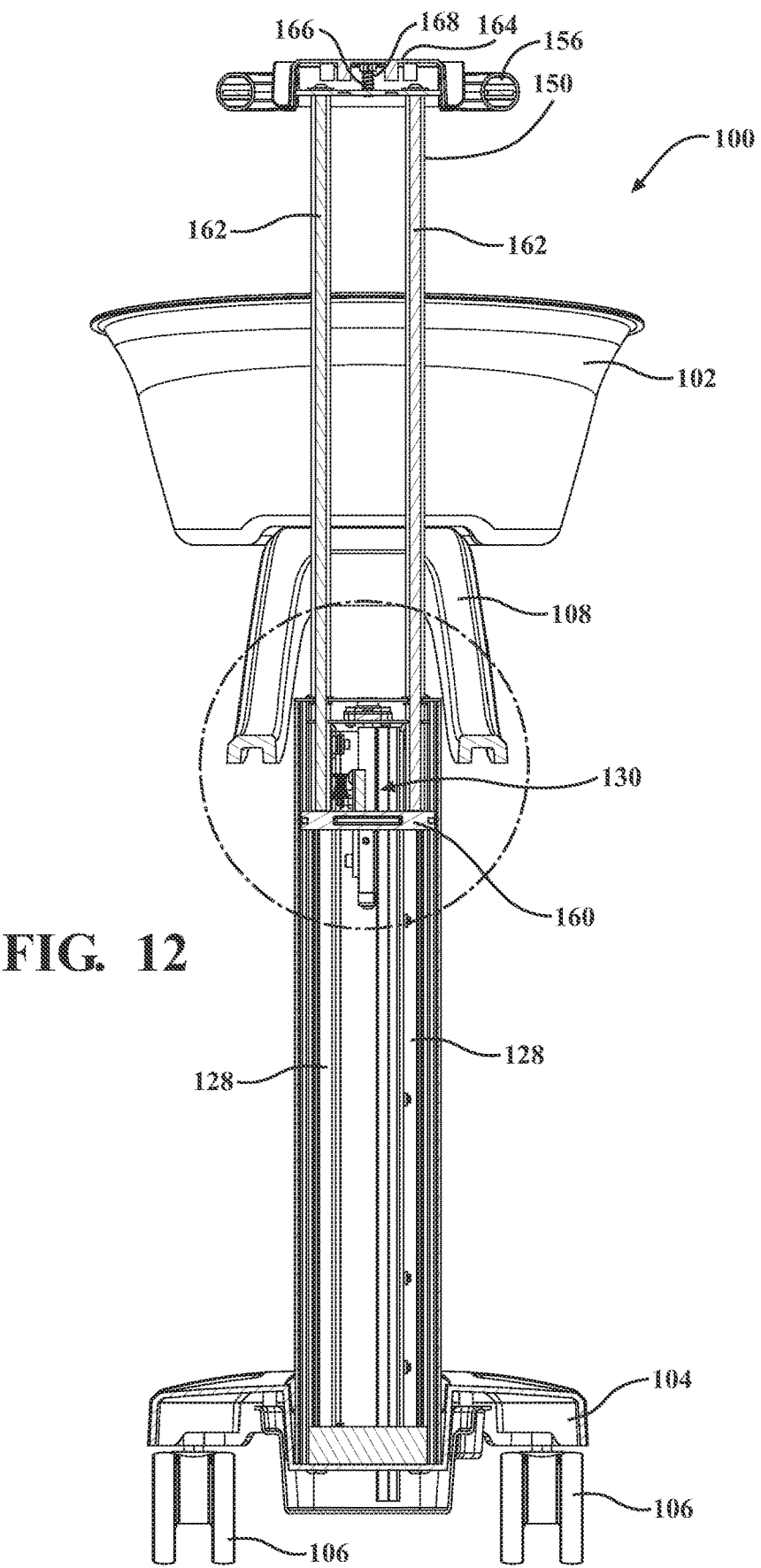
FIG. 12 is a sectional rear view of the bucket having the receptacle in the maximum height and having the lifting member in a raised position.

Referring now to FIGS. 6 and 7 the bucket 100 may also include a dampening assembly 134 configured to provide controlled movement of the carrier 108. The dampening assembly 134 is configured to dampen and slow down movement of the carrier 108 between the relatively high position (FIGS. 8-18) and the relatively low position (FIGS. 1-7). The dampening assembly 134 may be configured to absorb some of the movement forces from the carrier 108 and/or may be configured to resist the movement of the carrier 108 in order to provide controlled movement of the carrier 108. In one example, best illustrated in FIGS. 4 and 7, the dampening assembly 134 is a single direction system such that the dampening assembly 134 is configured to provide controlled movement of the carrier 108 only from the relatively high position (FIGS. 8-18) to the relatively low position (FIGS. 1-7). In this case, the dampening assembly 134 is configured to provide resistance in the opposite direction of the movement of the carrier 108, i.e. during movement of the carrier from the relatively high position (FIGS. 8-18) to the relatively low position (FIGS. 1-7), the dampening assembly is configured to provide resistance in direction from the relatively low position (FIGS. 1-7) to the relatively high position (FIGS. 8-18), thereby providing controlled movement of the carrier from the relatively high position (FIGS. 8-18) to the relatively low position (FIGS. 1-7). However, a multi-direction system such that the dampening assembly 134 is also configured to provide controlled movement of the carrier 108 from the relatively low position (FIGS. 1-7) to the relatively high position (FIGS. 8-18) has also been contemplated.

In one example, the dampening assembly 134 includes a tension member 136, a pulley 138, and a dampener 140. The tension member 136 extends between the dampener 140 and the carrier 108 to assist in moving the carrier 108 between the relatively high position (FIGS. 8-18) and the relatively low position (FIGS. 1-7). The movement of the carrier 108 exerts a force on the tension member 136. As a result, the exerted forces act on the dampener 140 which creates resistance against the exerted forces thereby dampening and slowing the movement of the carrier 108. In one example, the dampener 140 may be a rotary dampener and include fluid therein which passes though the rotary dampener to provide the dampening effect. As best shown in FIG. 7, the dampener 140 may include a rotatable spool portion having a circumference and configured to receive the tension member about the circumference. In one example, the dampener 140 is configured to exert a force on the tension member though a rotational force exerted on the spool portion. Therefore, when the carrier is in the relatively high position less than one circumference length of the tension member is received by the spool portion and when the carrier is in the relatively low position more than one circumference length of the tension member is received by the spool portion. More specifically, multiple circumference lengths of the tension member may be wrapped around the spool portion when the carrier is in the relatively low position.

In the example shown in FIGS. 4-7, the tension member 136 extends vertically from the second end of the support member 116 to an underside of the base 104. At the underside of the base 104, the pulley 138 is configured to facilitate a change in direction of the tension member 136 such that the tension member 136 extends horizontally along the underside of the base 104 from the pulley 138 to the dampener 140. The pulley 138 is disposed between the carrier 108 and the dampener 140. In one example, the pulley is coupled to the base. In another example, the pulley is coupled to a lower end of the support member 116. Other coupling locations of the pulley have also been contemplated. It is also contemplated that the dampening assembly 134 may also include a constant force spring, a spring reel, or another tension member to help facilitate controlled movement of the carrier 108.

The tension member 136 of the dampening assembly 134 may be further configured to assist movement of the carrier 108 between the relatively high position (FIGS. 8-18) and the relatively low position (FIGS. 1-7) and a winder 144. The tension member 136 typically extends from the second end of the support member 116 to the underside of the base 104 where extra slack may be contained by the winder 144. The winder 144 is rotatably coupled to the tension member 136 such that configured to wind extra slack of the tension member 136, typically when the carrier 108 is moved from the relatively high position (FIGS. 8-18) to the relatively low position (FIGS. 1-7). It is also contemplated that the winder 144 may be configured to wind extra slack of the tension member 136 during any movement of the carrier 108. In the example illustrated in FIG. 7 the winder 144 is disposed on the underside of the base 104 adjacent to the pulley 138, however, it is also contemplated that the winder 144 may be disposed elsewhere on the bucket 100, including but not limited to another location on the underside of the base 104 or on the support member 116. It is also contemplated that a constant force spring may replace the winder 144 such that the constant force spring is configured to wind extra slack of the tension member 142 during movement of the carrier 108.

The bucket 100 may also include various other components configured to prevent impact having a potentially damaging force when the carrier is moved from the relatively high position to the relatively low position. Examples of additional components include but are not limited to one or more rubber gaskets, shims, or the like.

Figure 46:
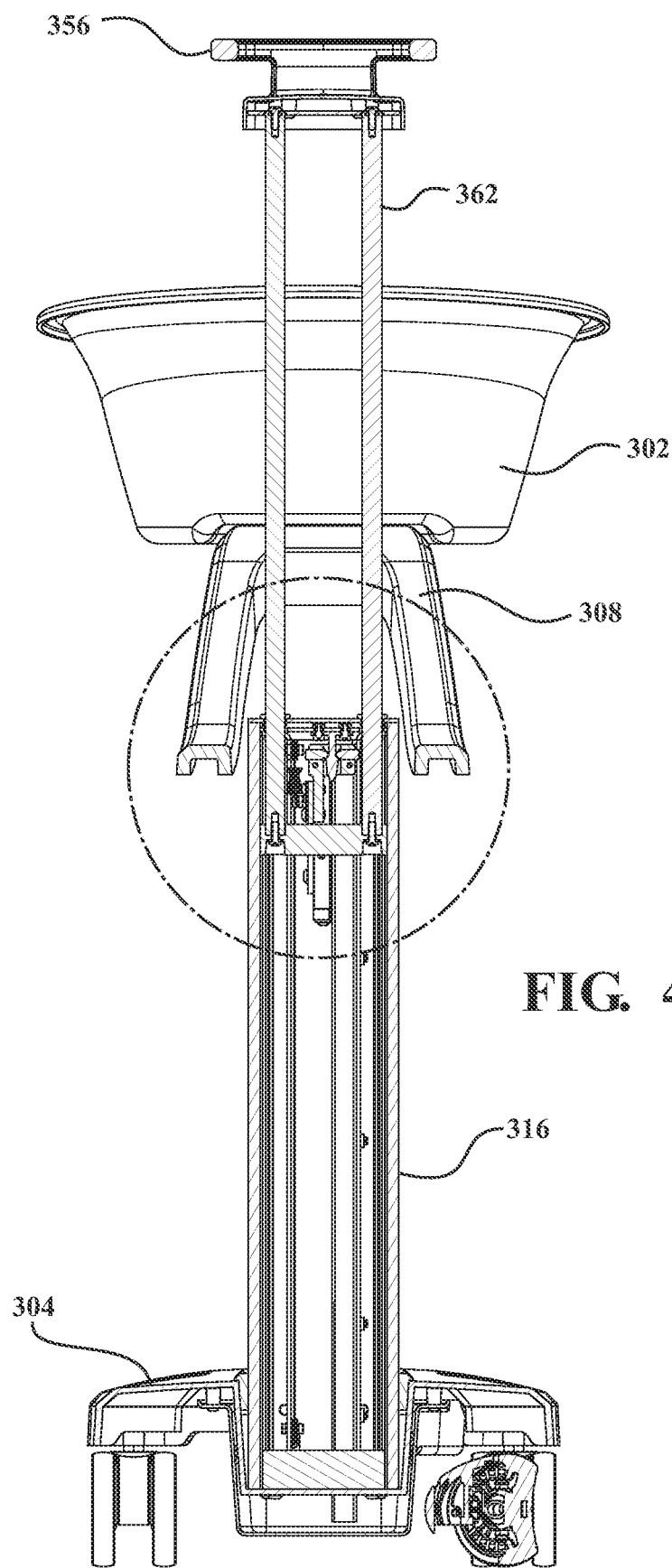
FIG. 46 is a sectional rear view of the bucket having the receptacle in the maximum height and having the lifting member in a raised position.
Figure 47:
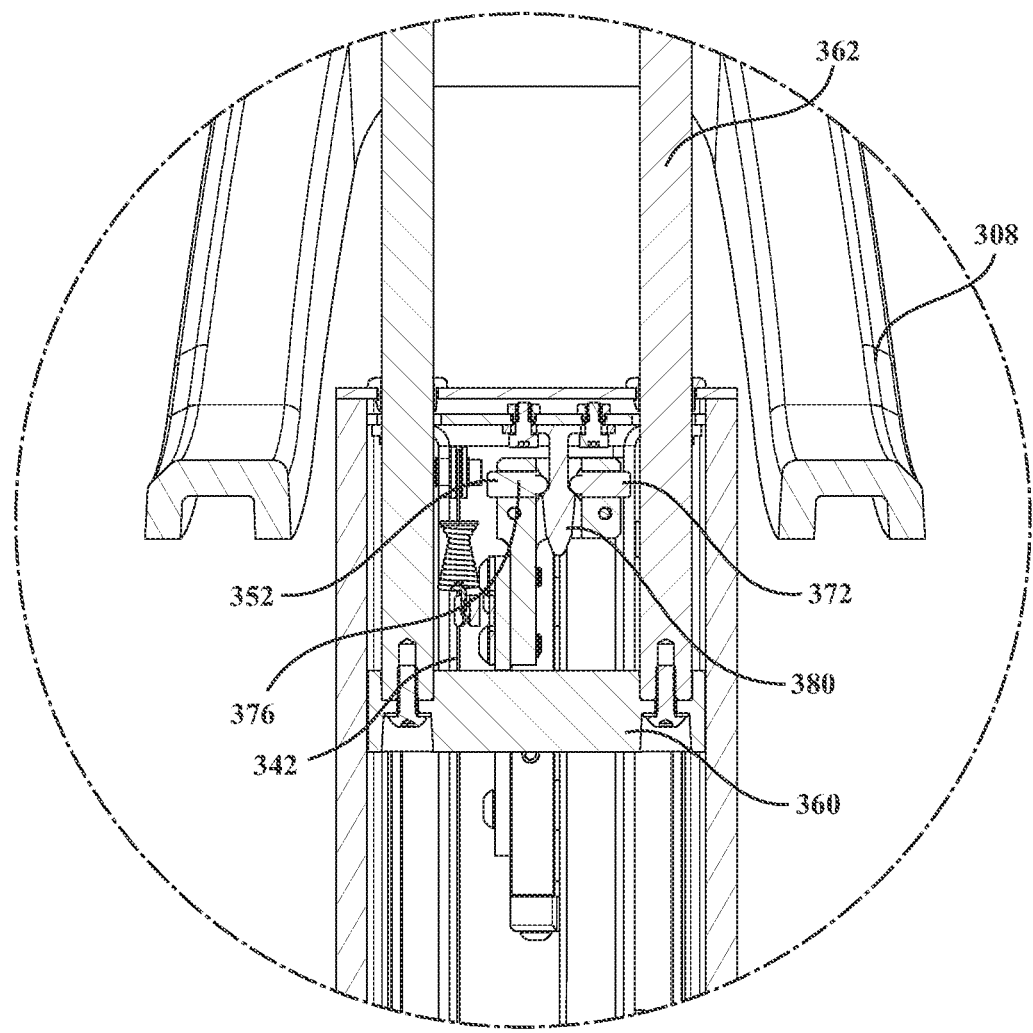
FIG. 47 is a magnified view of a portion of FIG. 46.
Figure 48:
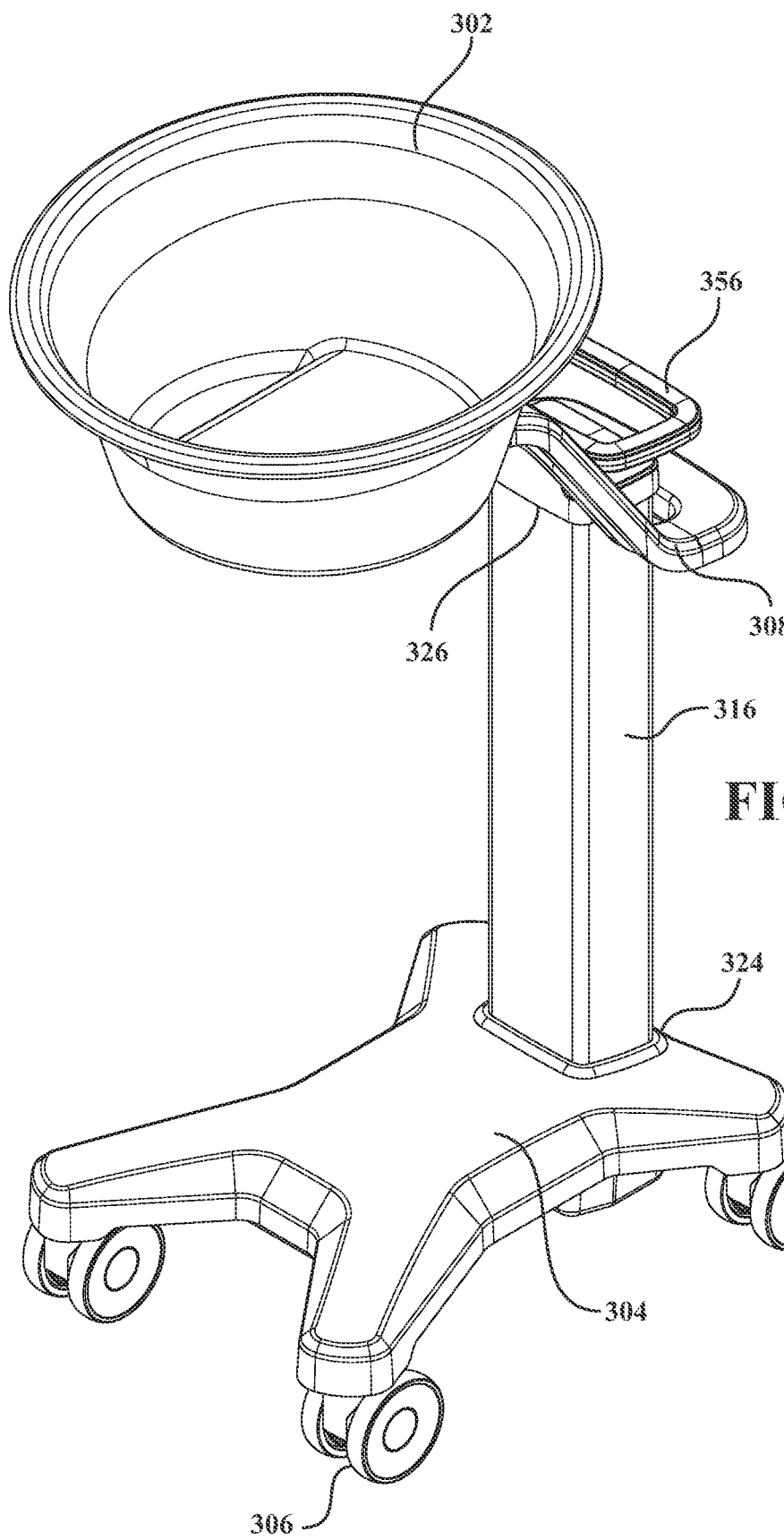
FIG. 48 is a front perspective view of the bucket having the receptacle in the maximum height and having the lifting member in the lowered position.
Figure 49:
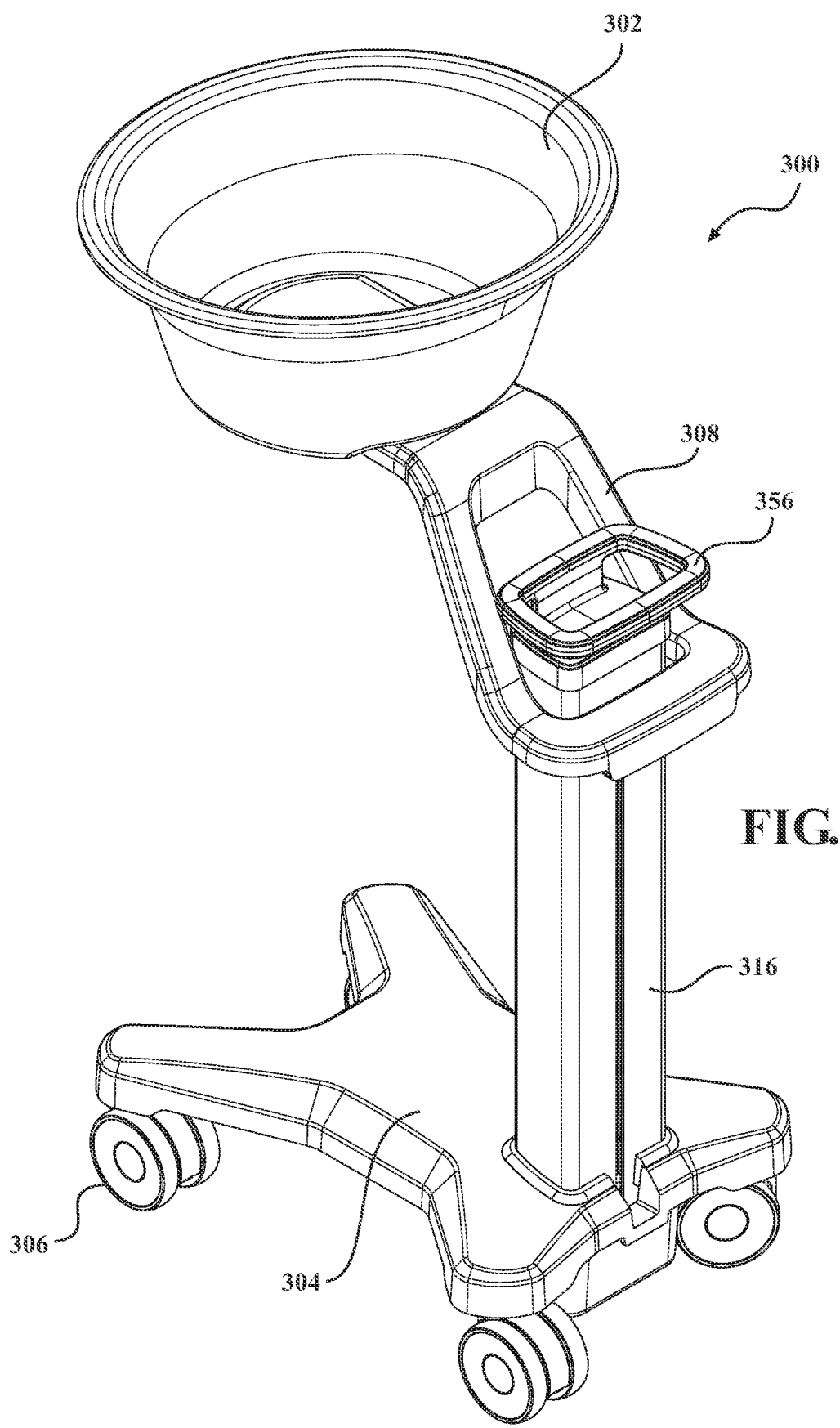
FIG. 49 is a rear perspective view of the bucket having the receptacle in the maximum height and having the lifting member in the lowered position.
Figure 50:
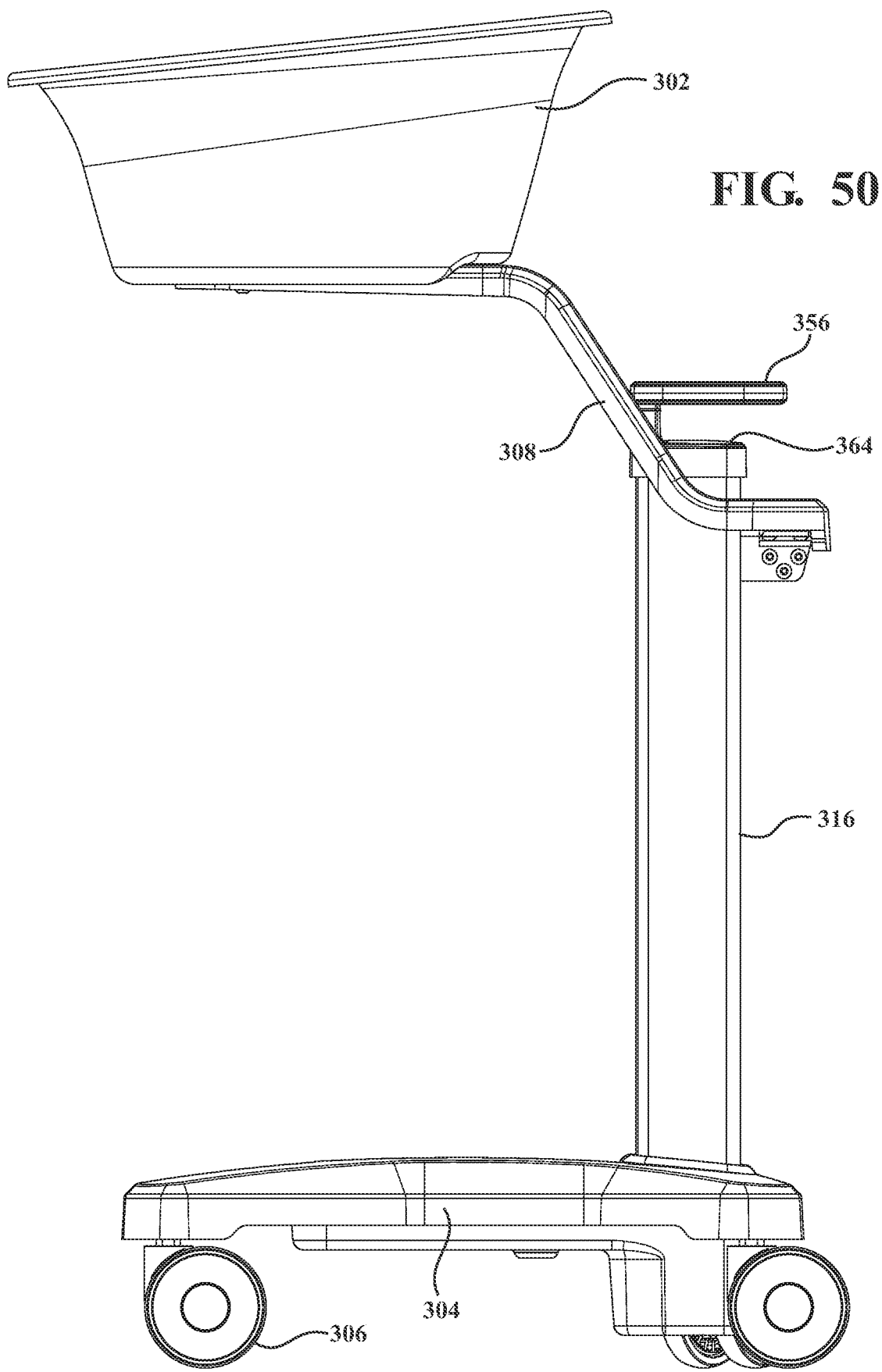
FIG. 50 is a side view of the bucket having the receptacle in the maximum height and having the lifting member in the lowered position.
Figure 51:
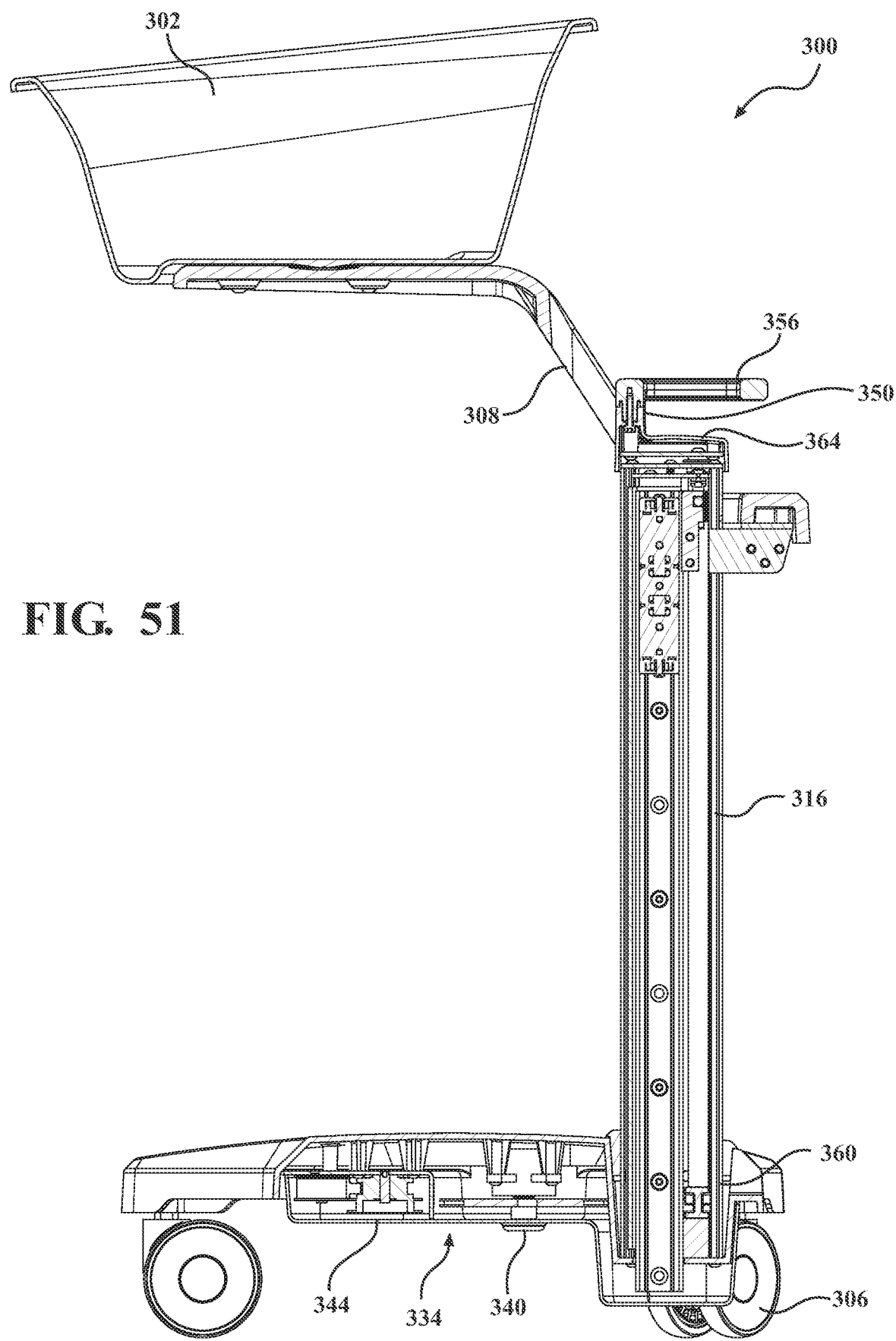
FIG. 51 is a sectional side view of the bucket having the receptacle in the maximum height and having the lifting member in the lowered position.
Figure 52:
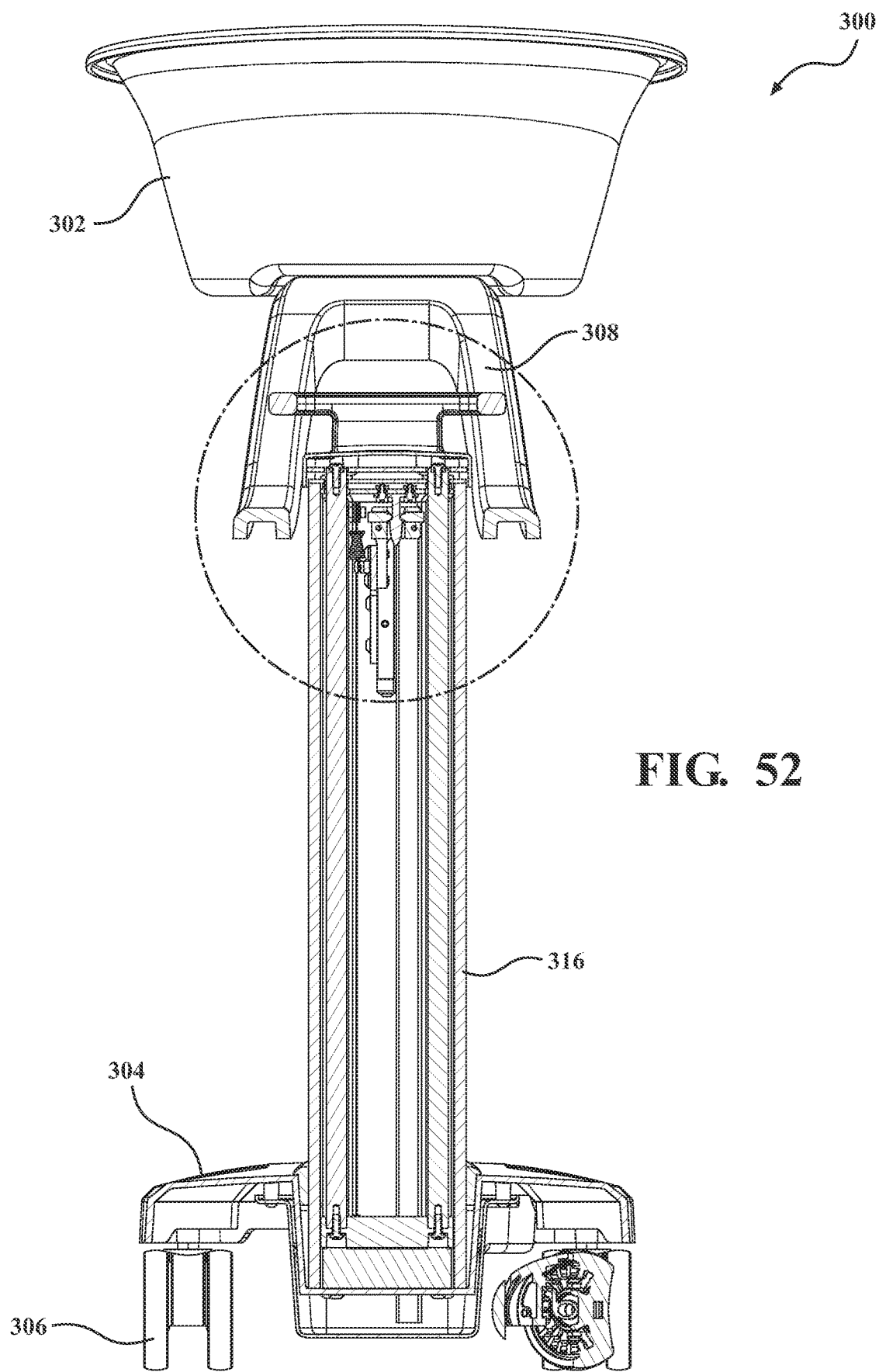
FIG. 52 is a sectional rear view of the bucket having the receptacle in the maximum height and having the lifting member in the lowered position.

The bucket 100 also includes the lifting member 150 slidably coupled to the carrier 108. Moreover, the lifting member 150 is configured to move between a raised position (FIGS. 8-13) and a lowered position (FIGS. 1-7 and 14-19). In one example, when the lifting member 150 is in the lowered position, an upper most surface of the lifting member is below an upper most portion of the receptacle 102 when the receptacle 102 is in the maximum position. This configuration allows the entire bucket 100 to be store under the sterile zone if desired by a user. More specifically, the lifting member 150 is configured to move from the lowered position to the raised position and back to the lowered position. The lifting member 150 includes a first end portion 154 which includes a handle 156 and a second end portion 158 which is opposite the first end portion 154. As best shown in FIG. 46, The lifting member may comprise one or more cylinders 162 extending between the first end portion 154 and the second end portion 158. The handle 156 may be of any size and shape and configured to allow engagement of a user to move the lifting member 150 between the raised position and the lowered position. The second end portion 158 also includes a stop member 160 configured to operatively engage the carrier 108 (see FIGS. 11-13). More specifically, when a user moves the handle 156 from the lowered position to the raised position, the stop member 160 engages an underside of the lower portion 114 to the carrier 108 and assists to move the carrier 108 from the relatively low position (FIGS. 1-7) to the relatively high position (FIGS. 8-18). The stop member 160 may be any size and shape configured to engage the carrier 108 and assist the movement of the carrier 108. Moreover, it is contemplated that the stop member 160 may engage the base 104 when the lifting member 150 is in the lowered position. The stop member 160 may be an integral piece of the second end portion 158 of the lifting member 150 or may be a separate piece circumferentially arranged around the second end portion 158 of the lifting member 150. In the example where the lifting member 150 comprises multiple cylinders 162, the stop member 160 may extend around one or more cylinders 162. It is also contemplated that the base 104 may have a recess configured to allow second end of the lifting member 150 to rest in the recess when the lifting member 150 is in the lowered position such that second end of the lifting member 150 engages the base 104 and the stop member 160 does not engage the base 104 when the lifting member 150 is in the lowered position.

In the example shown in FIG. 1-20, the lifting member 150 includes two cylinders 162 extending vertically between the first end and the second end of the lifting member 150. As shown in FIG. 1, the cylinders 162 may be disposed spaced apart from and parallel to each other from the handle 156 to the stop member 160. In one example, the handle 156 may be configured to connect the cylinders 162. Additionally, or alternatively, the stop member 160 may be configured to connect the cylinders 162. In the example shown, the stop member 160 extends perpendicularly to the cylinders 162 and is disposed around and configured to connect both cylinders 162. However, it is contemplated that the lifting member 150 may include more or less cylinders 162 and the stop member 160 may be configured to be disposed around one or more of the cylinders 162 in order to assist the carrier 108 in moving from the relatively low position (FIGS. 1-7) to the relatively high position (FIGS. 8-18). The cylinders 162 and stop member 160 may be comprised of any material including but not limited to stainless steel, plastic, or another material.

Figure 17:
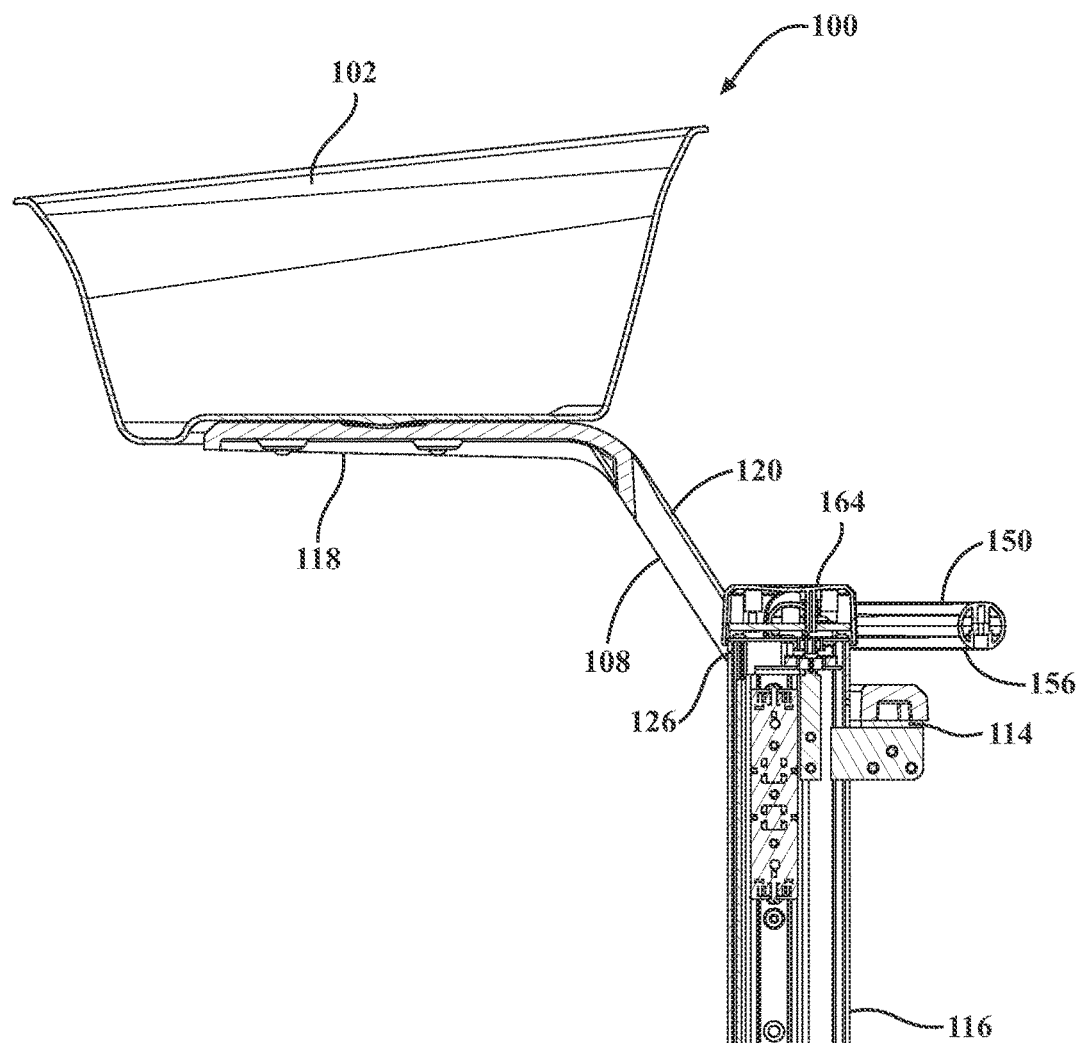
FIG. 17 is a sectional side view of the bucket having the receptacle in the maximum height and having the lifting member in the lowered position.
Figure 19:
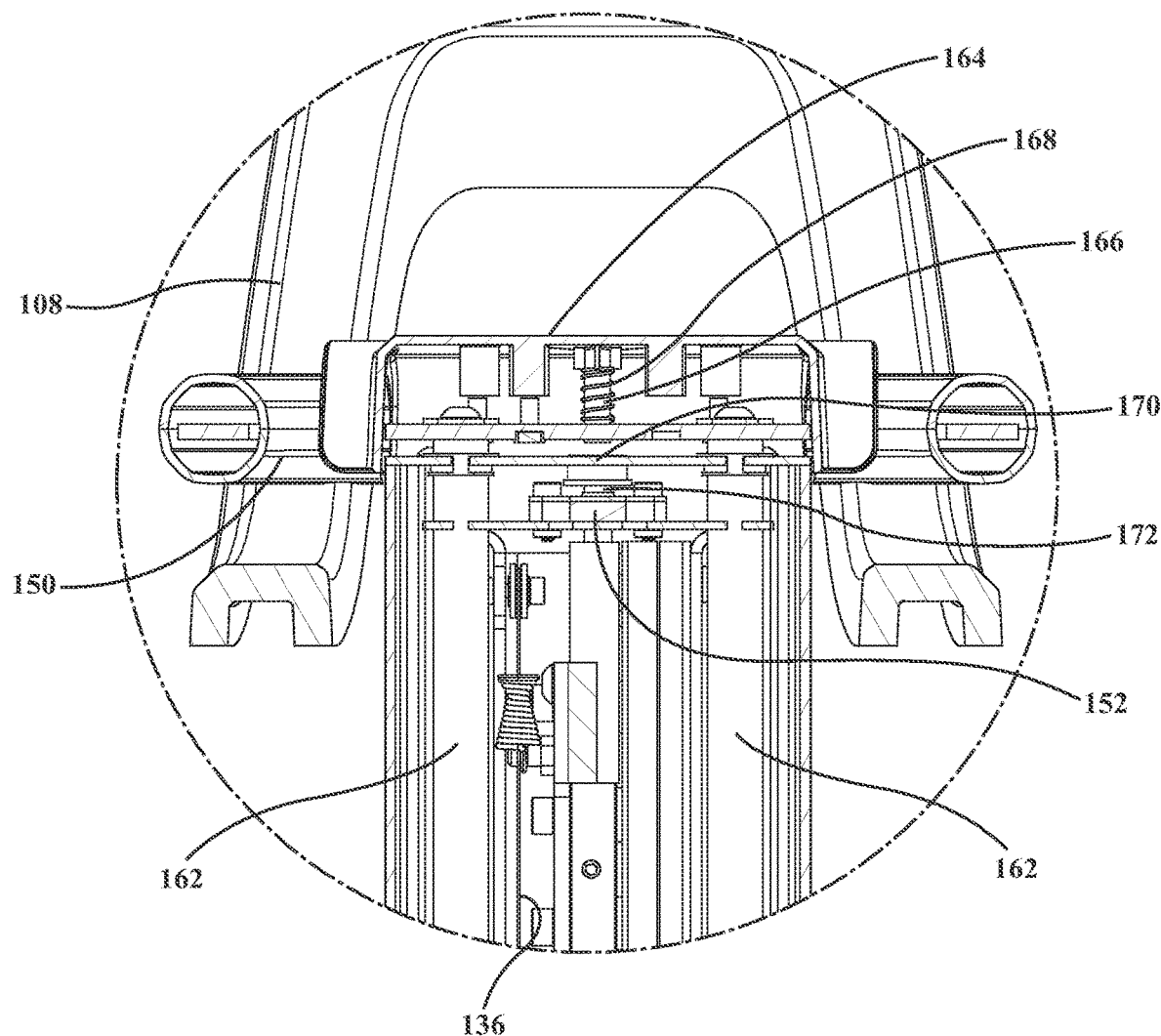
FIG. 19 is a magnified view of a portion of FIG. 18.
Figure 20:
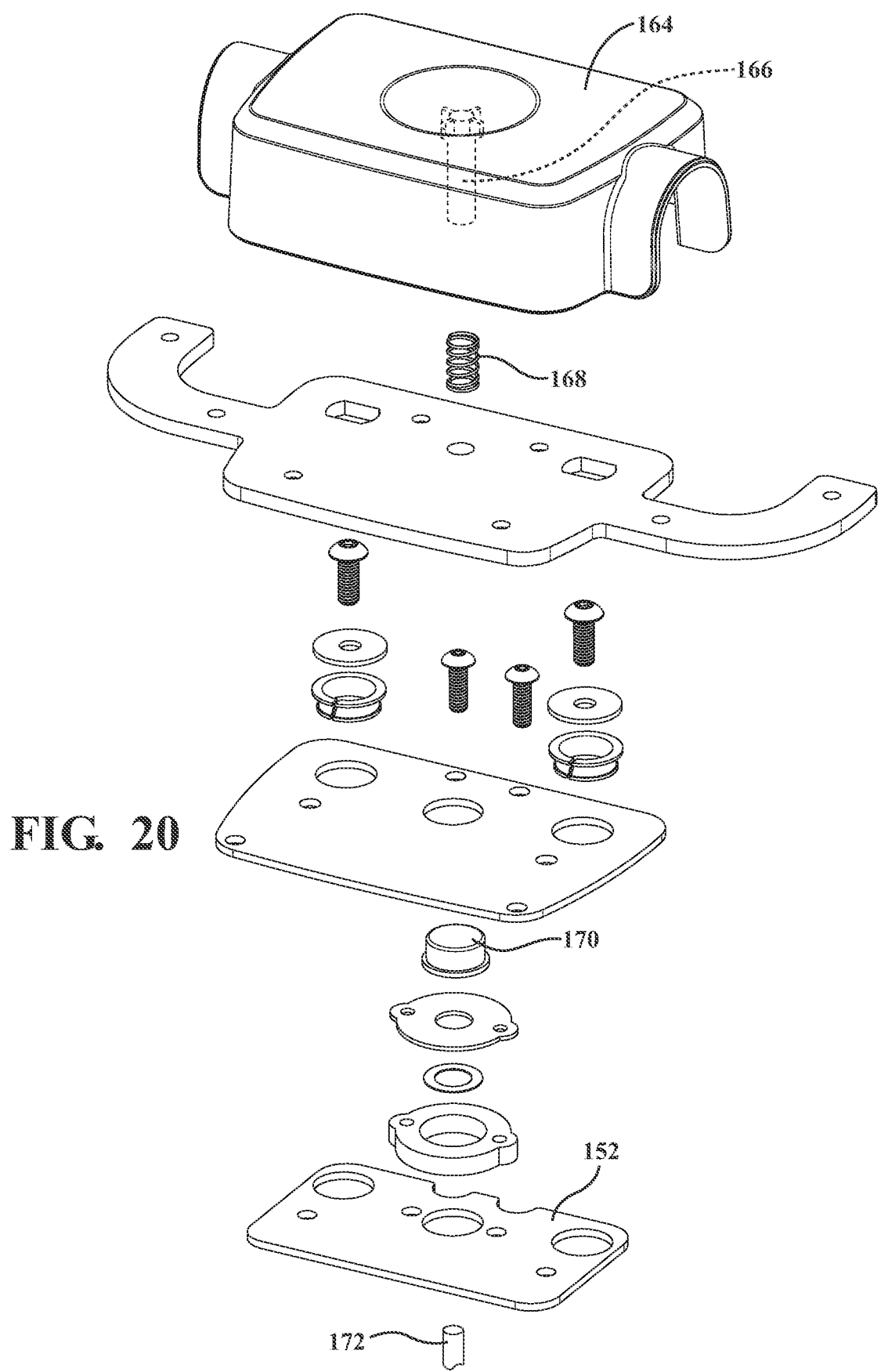
FIG. 20 is an exploded view of an exterior engagement surface of the lifting member and an interior engagement surface of a support member of the bucket of FIG. 1.
Figure 21:
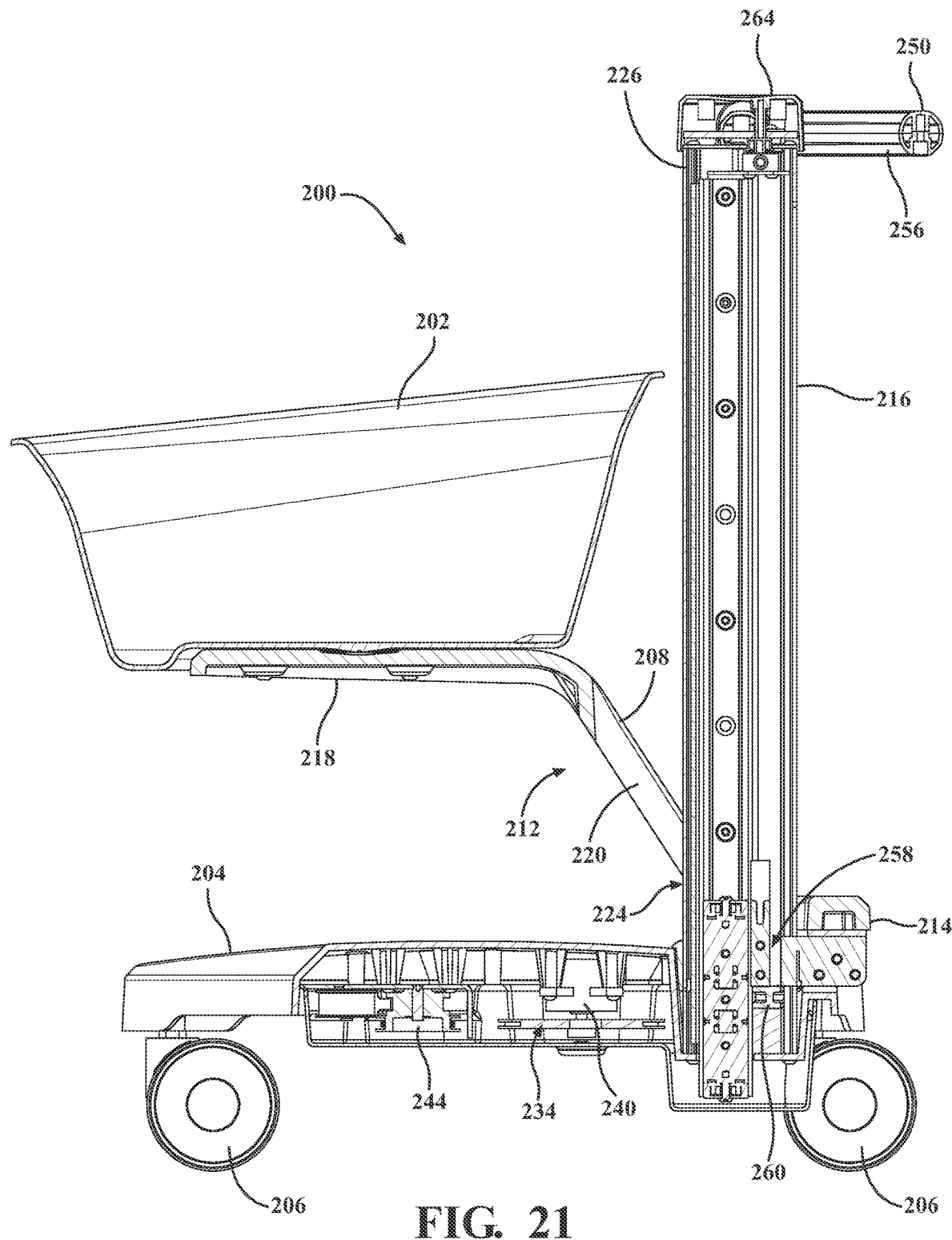
FIG. 21 is a sectional side view of another example of a bucket having a receptacle in a minimum height and having the lifting member in the lowered position.
Figure 22:
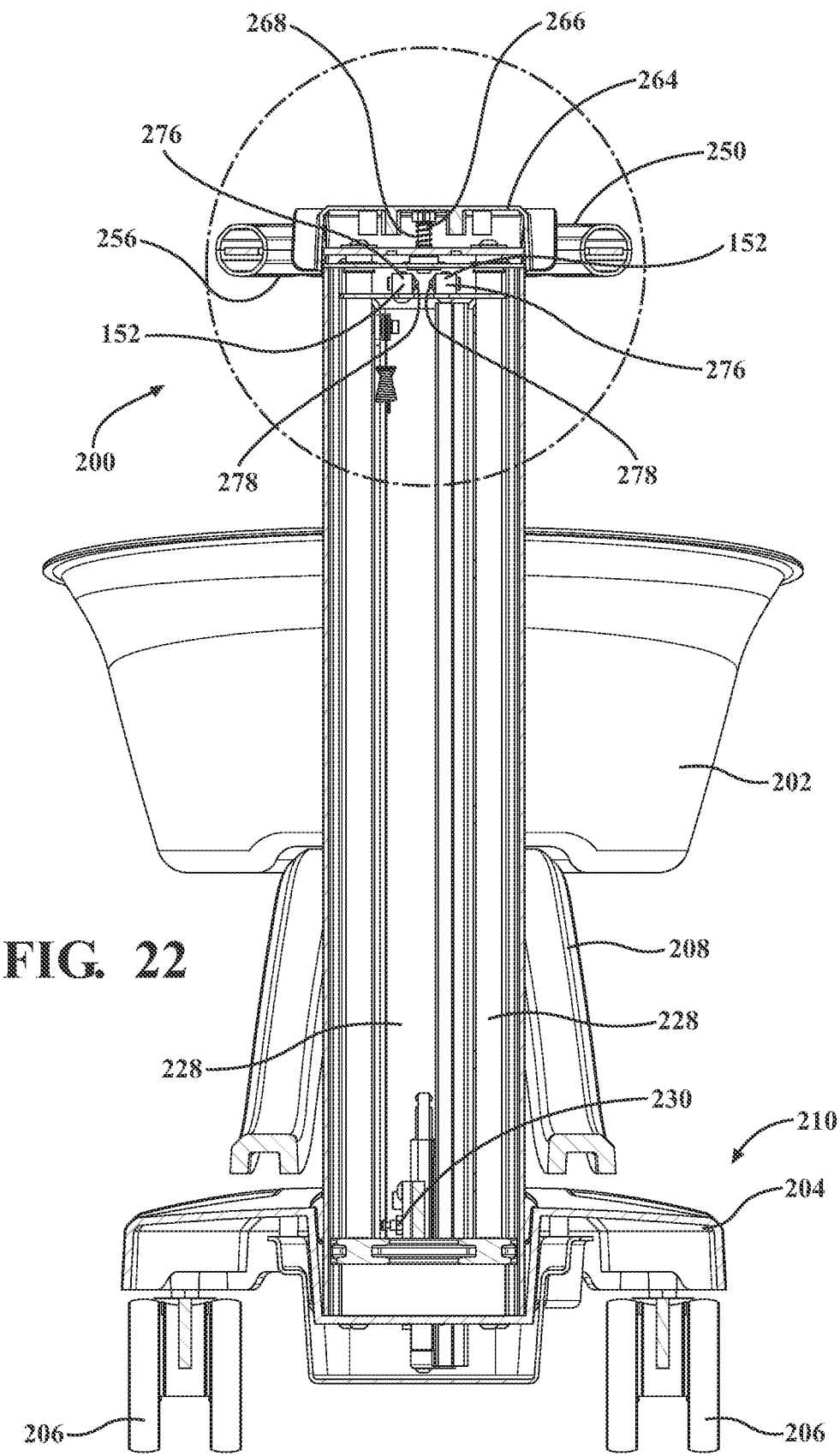
FIG. 22 is a sectional rear view of the bucket of FIG. 21 having the receptable in the minimum height and having the lifting member in the lowered position.
Figure 23:
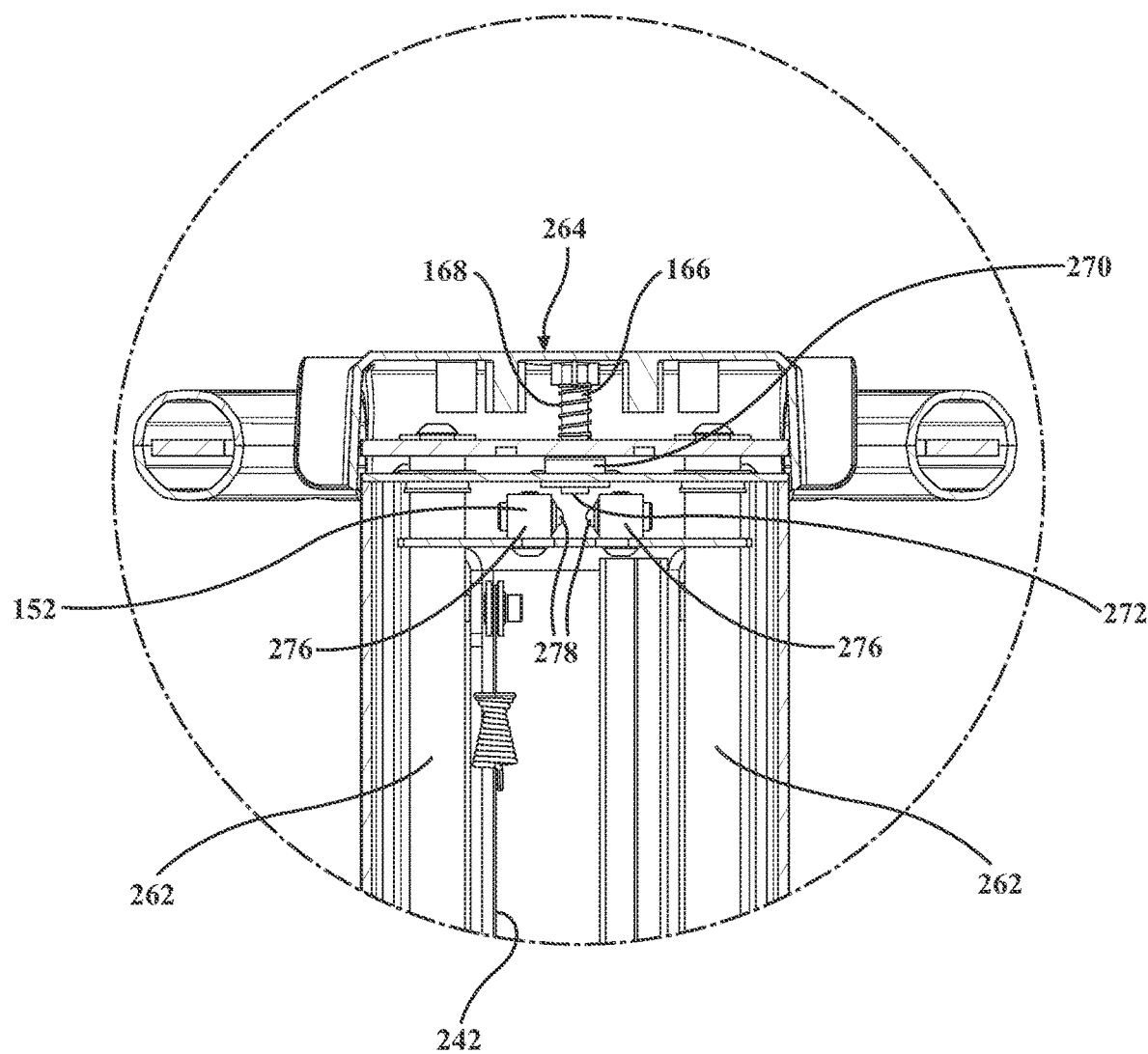
FIG. 23 is a magnified portion of FIG. 22.
Figure 24:
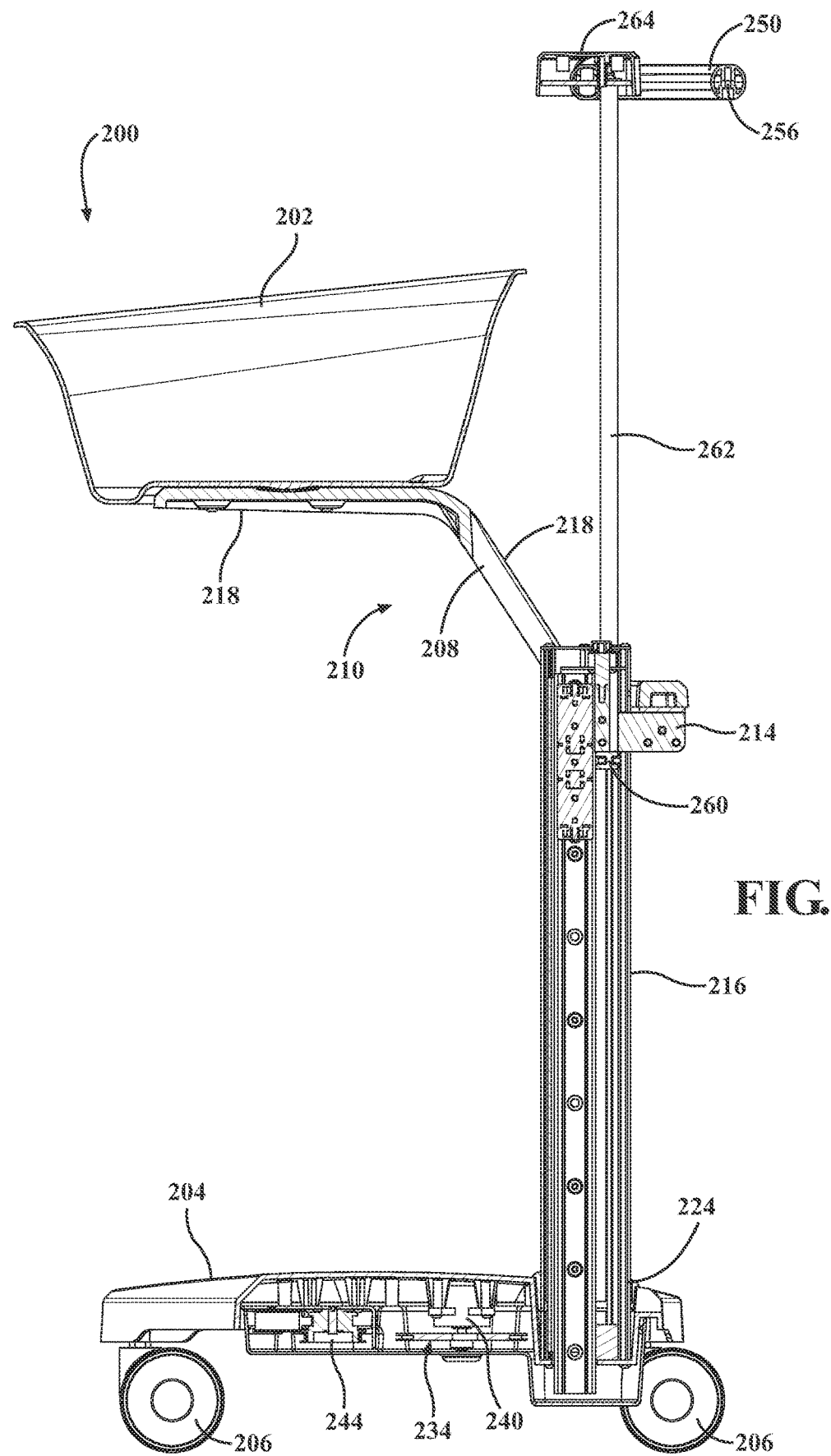
Figure 25:
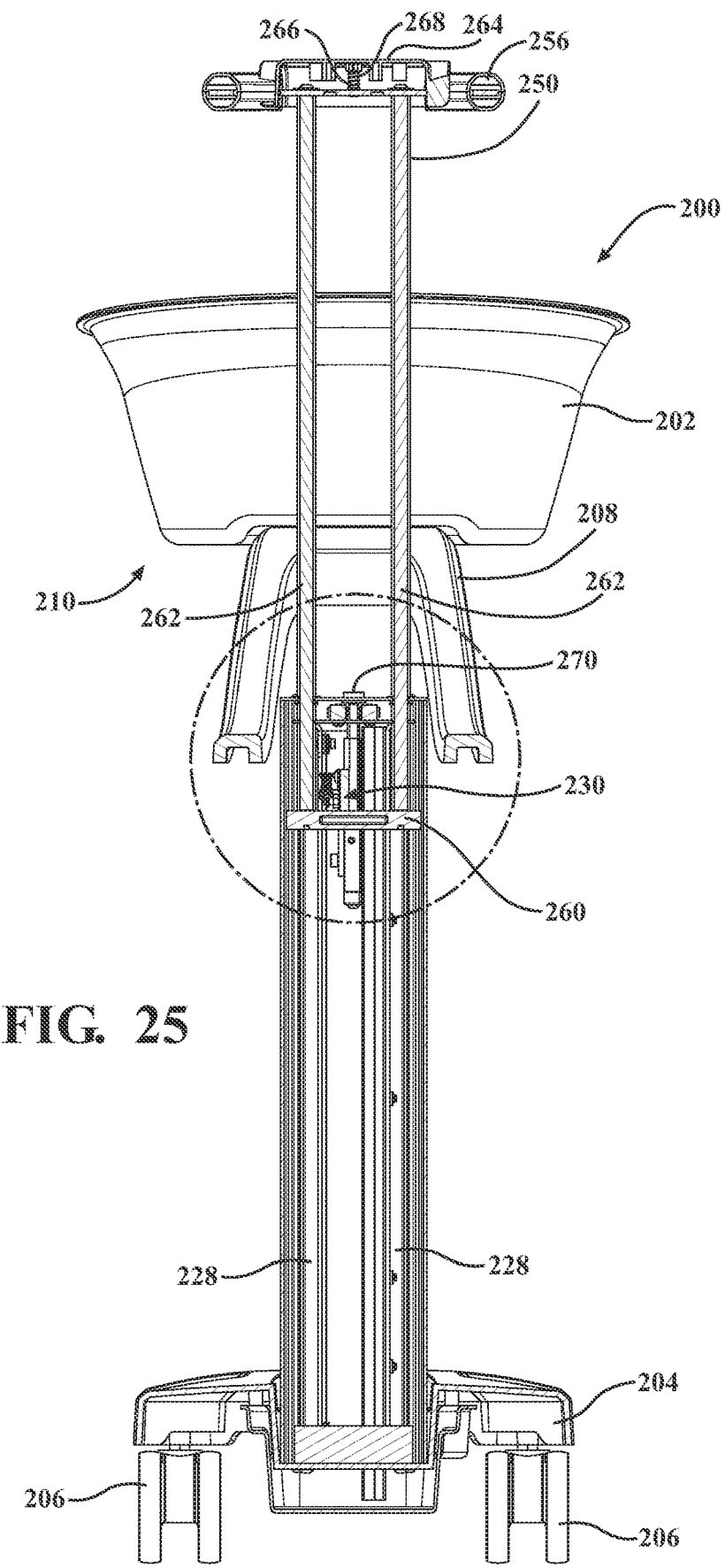
FIG. 25 is a sectional rear view of the bucket of FIG. 21 having the receptacle in the maximum height and having the lifting member in a raised position.
Figure 26:
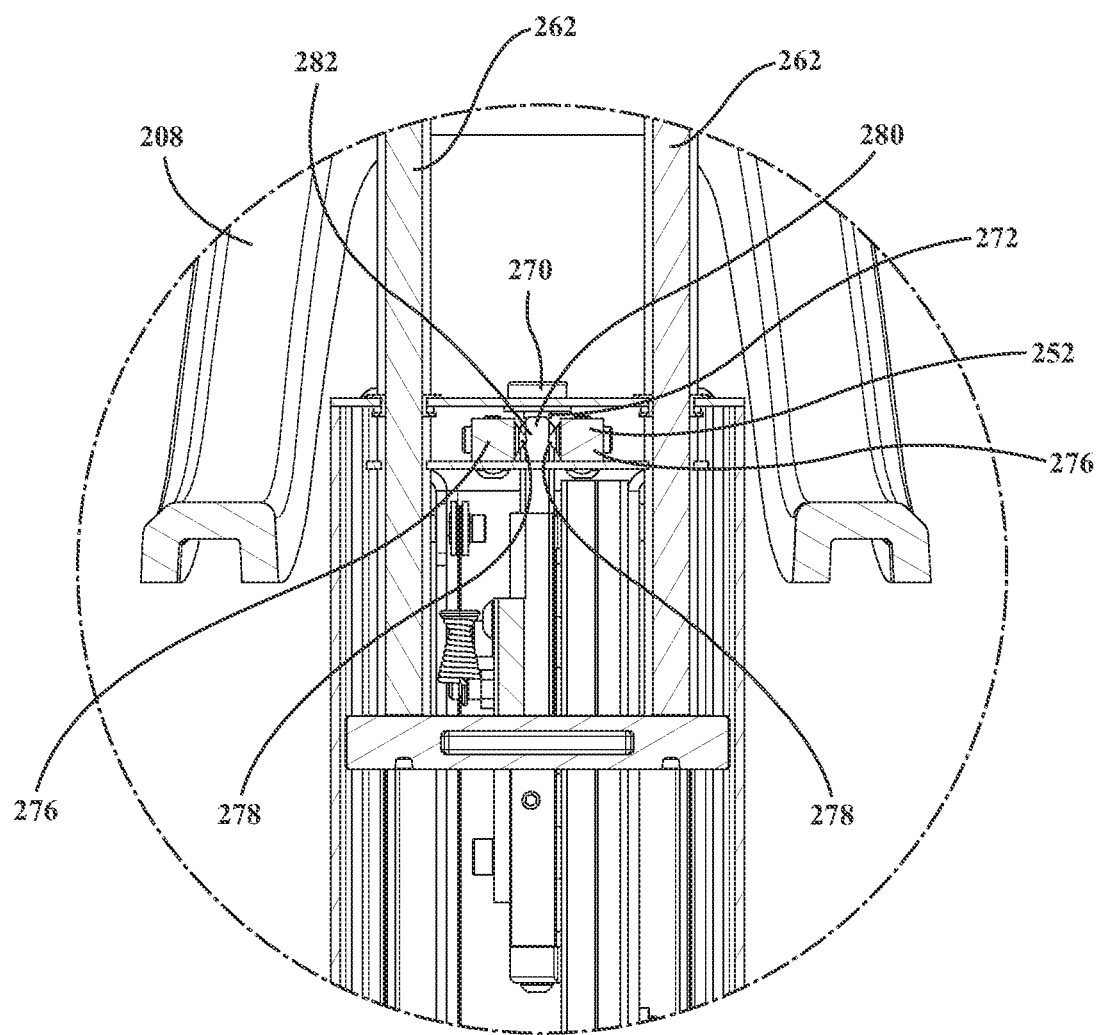
FIG. 26 is a magnified view of a portion of FIG. 25.
Figure 27:
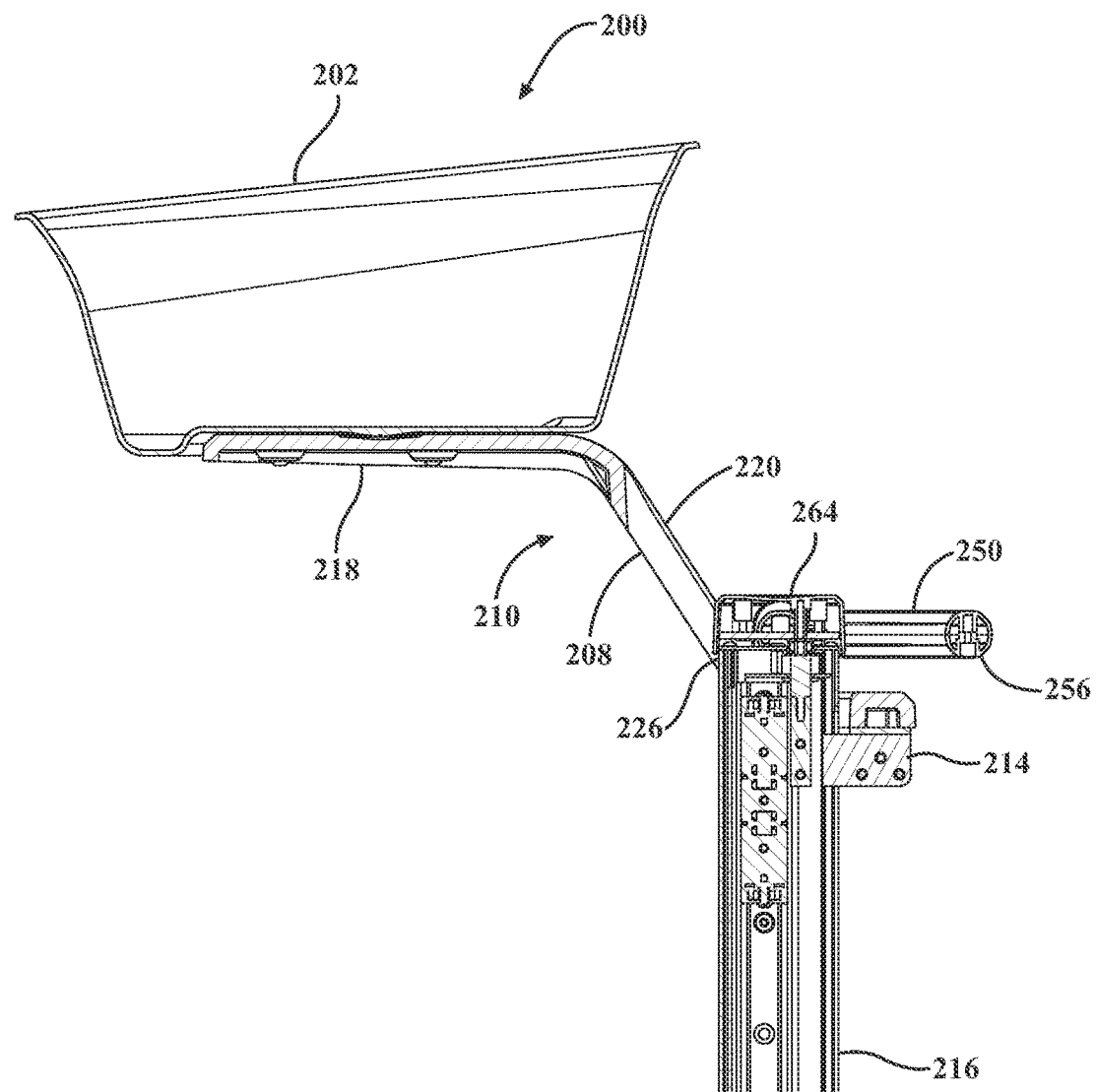
FIG. 27 is a sectional side view of the bucket of FIG. 21 having the receptacle in the maximum height and having the lifting member in the lowered position.
Figure 29:
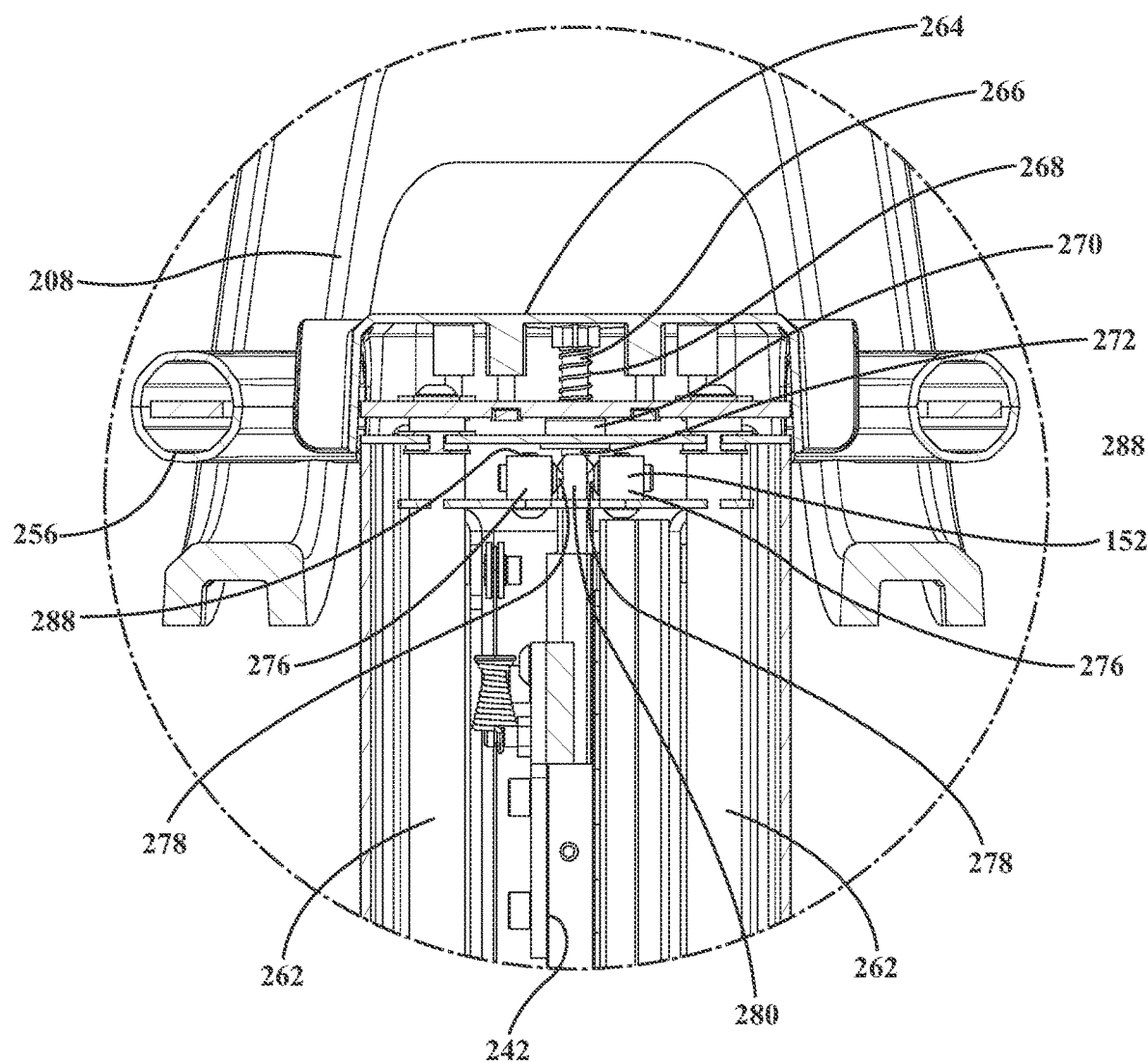
FIG. 29 is a magnified view of a portion of FIG. 28.

Referring still to FIGS. 1-20 the lifting member 150 is configured to be in the lowered position when the carrier 108 is in the relatively high position (FIGS. 8-18) and when the carrier 108 is in the relatively low position (FIGS. 1-7). Moreover, as shown in FIG. 17, the stop member 160 of the lifting member 150 is spaced from the carrier 108 when the lifting member 150 is in the lowered position and when the carrier 108 is in the relatively high position (FIGS. 8-18). More specifically, as best shown in FIGS. 1-7, when the receptacle 102 is in the minimum height the lower portion 114 of the carrier 108 is disposed adjacent to the first end of the support member 116 and the lifting member 150 is in the lowered position such that the handle 156 of the lifting portion is adjacent the second end of the support member 116. As best shown in FIGS. 8-19, when the receptacle 102 is in the maximum height, the lower portion 114 of the carrier 108 is disposed adjacent to the second end of the support member 116. Moreover, when the receptacle 102 is in the maximum height, the lifting member 150 may be in the lowered position (FIGS. 14-19) as described above or may be in the raised position such that the handle 156 is vertically spaced from the second end of the support member 116, as illustrated in FIGS. 8-13.

Referring to FIG. 15, the lifting member 150 defines an exterior engagement surface 164 configured to be activated by a user. The lifting member 150 also defines an engagement member 166 coupled to the exterior engagement surface 164 and configured to be moved from a first position to a second position upon activation of the exterior engagement surface 164. In one example, the first position of the engagement member 166 is the position the engagement member 166 is in prior to any engagement of the exterior engagement surface 164. When the engagement member 166 is moved to the second position, the engagement member 166 moves further from an underside of exterior engagement surface 164. The lifting member 150 may also include a biasing member 168 configured to return the engagement member 166 back to the first position from the second position. In the example shown in FIG. 6A, the exterior engagement surface 164 is a surface configured to be engaged by the user which extends an entire second end surface of the support member 116 such that a user can actuate the engagement member 166 by pressing at any location on the exterior engagement surface 164. Having the exterior engagement surface 164 as the entire second end surface of the support member 116 maintains an easy to clean surface while lessening the dexterity needed to actuate the engagement member 166. It is also contemplated that the exterior engagement surface 164 may be a foot pedal or other actuation mechanism.

Moreover, the exterior engagement surface 164 illustrated in FIGS. 1-20 is coupled to the handle 156 such that when a user lifts the handle 156 to move the lifting member 150 to the raised position, the exterior engagement surface 164 moves with the handle 156 to the raised position such that the exterior engagement surface 164 is spaced vertically from the second end of the support member 116. In the example illustrated in FIG. 6B, the exterior engagement surface 164 may be coupled to the support member 116 using the plurality of cylinders 162 which extend from the second end of the support member 116 when the lifting member 150 is moved to the raised position. It is also contemplated that the exterior engagement surface 164 may be coupled using any other configuration which allows the exterior engagement surface 164 to be moved along with the lifting member 150 to the raised position. Other locations for the exterior engagement surface 164 have been contemplated including but not limited to on only a portion of the surface of the second end of the support member 116, on the side of the support member 116, or within the handle 156 of the lifting member 150.

Additionally, the upper end portion 126 of the support member 116 defines an interior engagement surface 170 configured to be actuated by movement of the engagement member 166 into the second position. The support member 116 also includes a piston 172 configured to selectively uncouple the carrier 108 and support member 116 to allow the carrier 108 to move to the relatively low position (FIGS. 1-7) upon actuation of the interior engagement surface 170 by the engagement member 166. In the example illustrated in FIGS. 1-20, the piston 172 moves from a rest position to an engaged position upon activation of the interior engagement surface 170 by the engagement member 166. In the rest position, the piston 172 is disposed closed to the interior engagement surface and in the engaged position, the piston 172 is moved away from the interior engagement surface 170 and towards the carrier 108. Movement of the piston 172 from the rest position to the engaged position actively decouples the carrier 108 and the support member 116 to allow the carrier 108 to move to the relatively low position (FIGS. 1-7). In the example shown in FIG. 1-20, the interior engagement surface 170 is not visible when the lifting member 150 is in the lowered position. Having the interior engagement surface 170 be covered protects the interior engagement surface 170 from contamination and fluids which may be present during use of the bucket 100.

Additionally, in the example shown in FIG. 1-20, user engagement of the interior engagement surface 170 does not actuate movement of the carrier 108 from the relatively high position (FIGS. 8-18) to the relatively low position (FIGS. 1-7). By only allowing actuation of the exterior engagement surface 164 to uncouple the carrier 108 and support member 116 to allow the carrier 108 to move to the relatively low position (FIGS. 1-7), a user is discouraged from engaging the interior engagement surface 170 when the lifting member 150 is in the raised position preventing potential contamination of the interior components of the bucket 100 and preventing failure due to contamination.

As best illustrated in FIG. 13, the retainer 152 selectively couples the carrier 108 and the support member 116 and is configured to retain the carrier 108 in the high position. In one example, the retainer 152 includes a first coupling member and the carrier 108 includes a second coupling member. It is contemplated that one or more of the first and second coupling member may comprise magnetic material such that the coupling between the carrier 108 and the support member 116 is a magnetic coupling when the carrier 108 is in the relatively high position (FIGS. 8-18). More specifically, in the example illustrated in FIG. 13, the first coupling member is a first magnetic element disposed on the carrier and the second coupling member is a second magnetic element. As described above, in the example shown in FIG. 13, the first coupling member is a first magnetic element 131 disposed on the retainer and the second coupling member is a second magnetic element 133 disposed on the carrier 108. In the example shown in FIGS. 1-20, when the piston 172 is moved from the rest position to the engaged position, the piston 172 engages the first coupling member with enough force to decouple the first and second coupling members.

In one example, when the carrier 108 is in the relatively high position (FIGS. 8-18) and the retainer 152 is coupling the carrier 108 and the support member 116, the carrier 108 and the retainer 152 may be configured to automatically decouple from one another when contents of the receptacle 102 has a mass greater than a predetermined mass. In some examples, the predetermined mass may be from 4-10 kg, however, various predetermined masses have been contemplated including but not limited to any mass or range of masses between and including 0.5 kg-20 kg. In some configurations the predetermined mass is less than 10 lbs, less than 8 lbs, less than 6 lbs, or less than 4 lbs. Having the carrier 108 and the retainer 152 automatically decouple from one another when contents of the receptacle 102 has a mass greater than a predetermined mass prevents the receptacle 102 from having an impact which may be potentially damaging to one or more elements of the bucket 100 when returning to the lowered position. Therefore, in applications having incremental mass increases, such as a medical sponge collection application, the carrier 108 and the retainer 152 may be configured to automatically decouple after the next sponge is entered into the receptacle 102 as contents of the receptacle 102 has reached a mass greater than the predetermined mass. This ensures the dampening assembly 134 can provide smooth movement of the receptacle 102 from the high position to the low position without the weight of the receptacle 102 causing damage of or failure to the dampening assembly 134 or remaining portions of the bucket 100.

Figure 31:
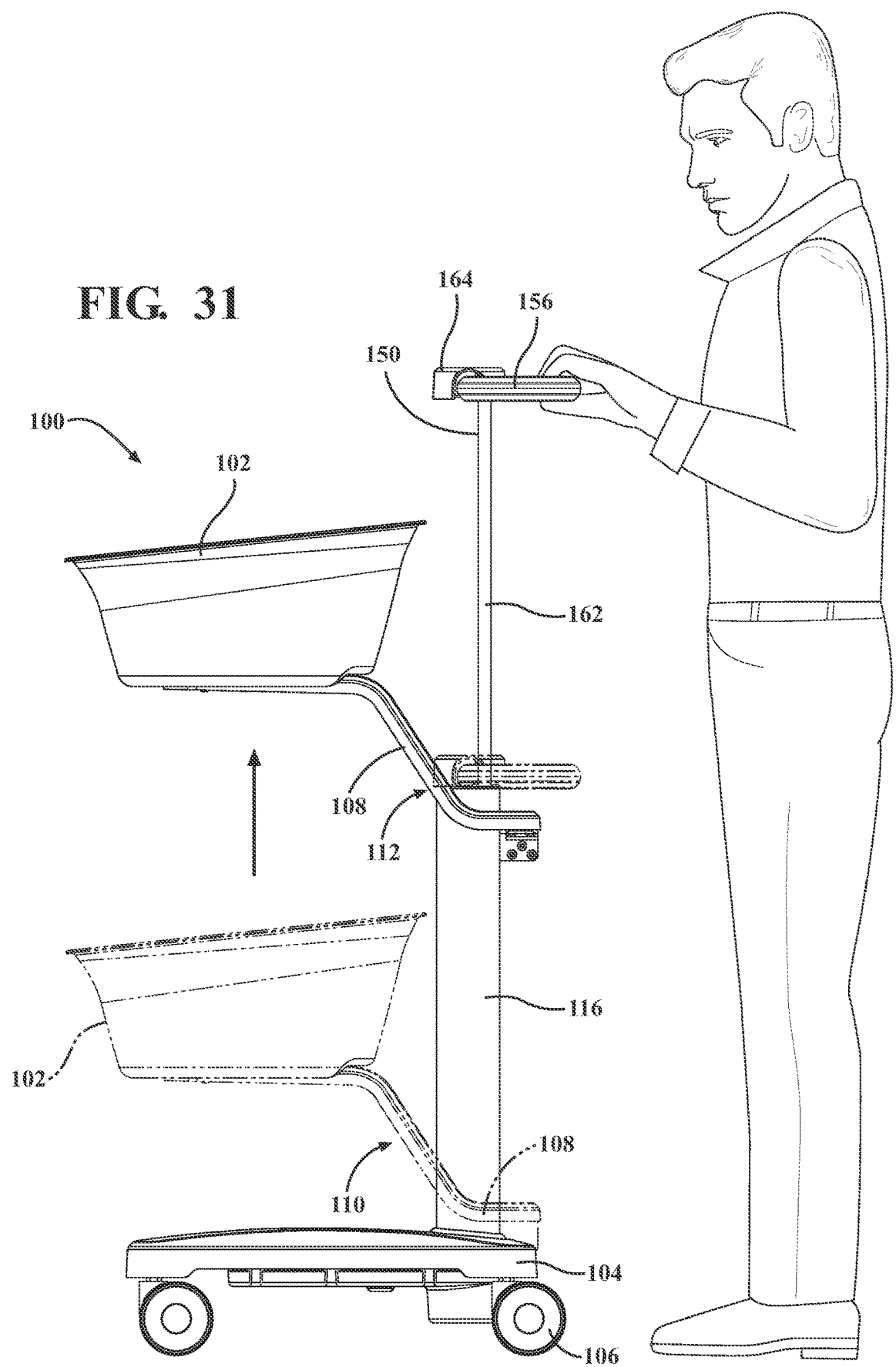
FIG. 31 is a schematic view of a user operating the bucket of FIG. 1 or of FIG. 21 by moving the lifting member from the lowered position to the raised position to thereby move the receptacle from the minimum height to the maximum height.
Figure 32:
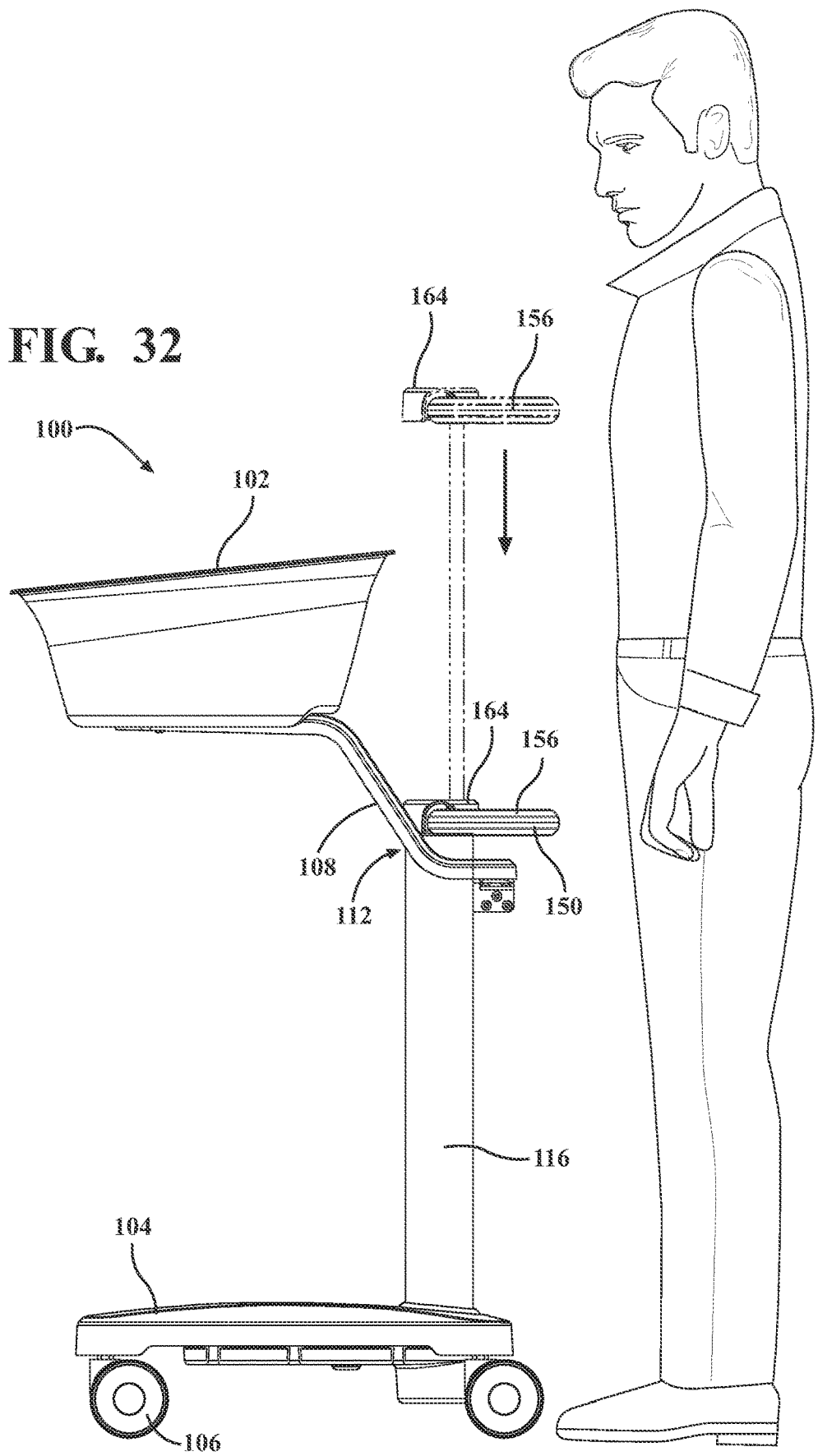
FIG. 32 is a schematic view of the lifting member returning to the lowered position, while the receptacle is maintained in the maximum height.
Figure 33:
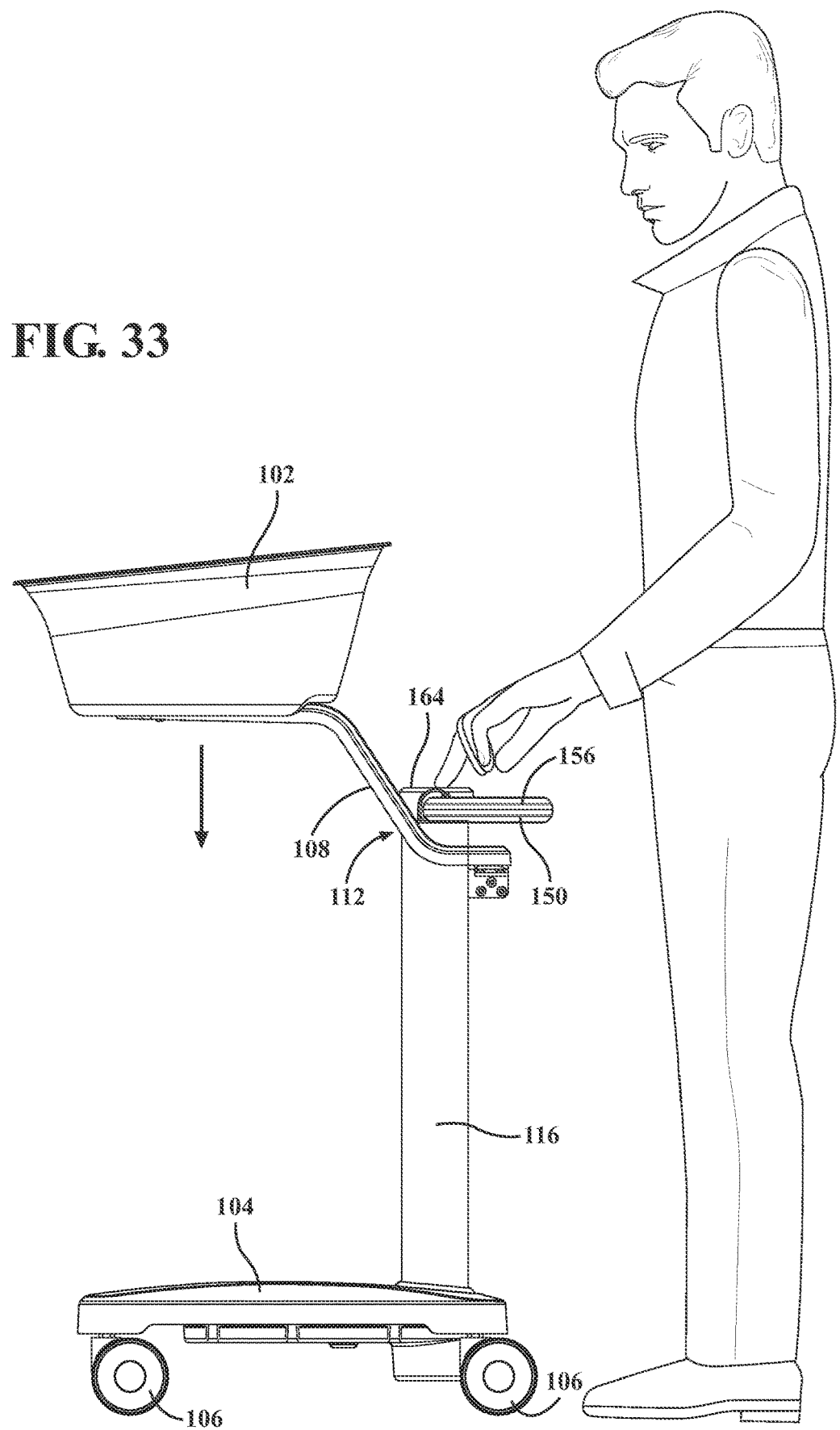
FIG. 33 is a schematic view of the user engaging the exterior engagement surface to return the receptacle to the minimum height, while the lifting member is in the lowered position.
Figure 34:
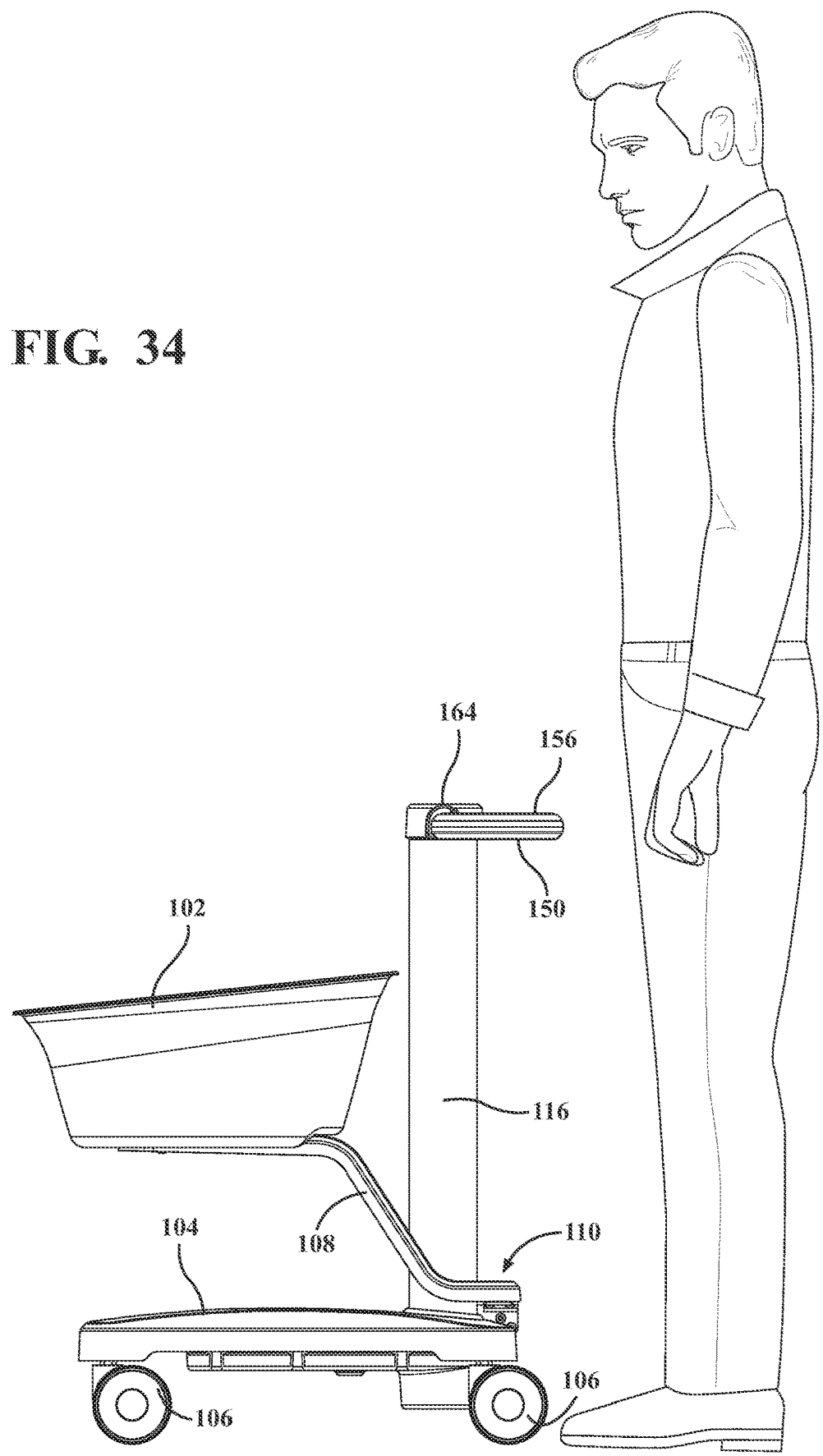
FIG. 34 is a schematic view of the receptacle returned to the minimum height, with the lifting member being in the lowered position.
Figure 35:
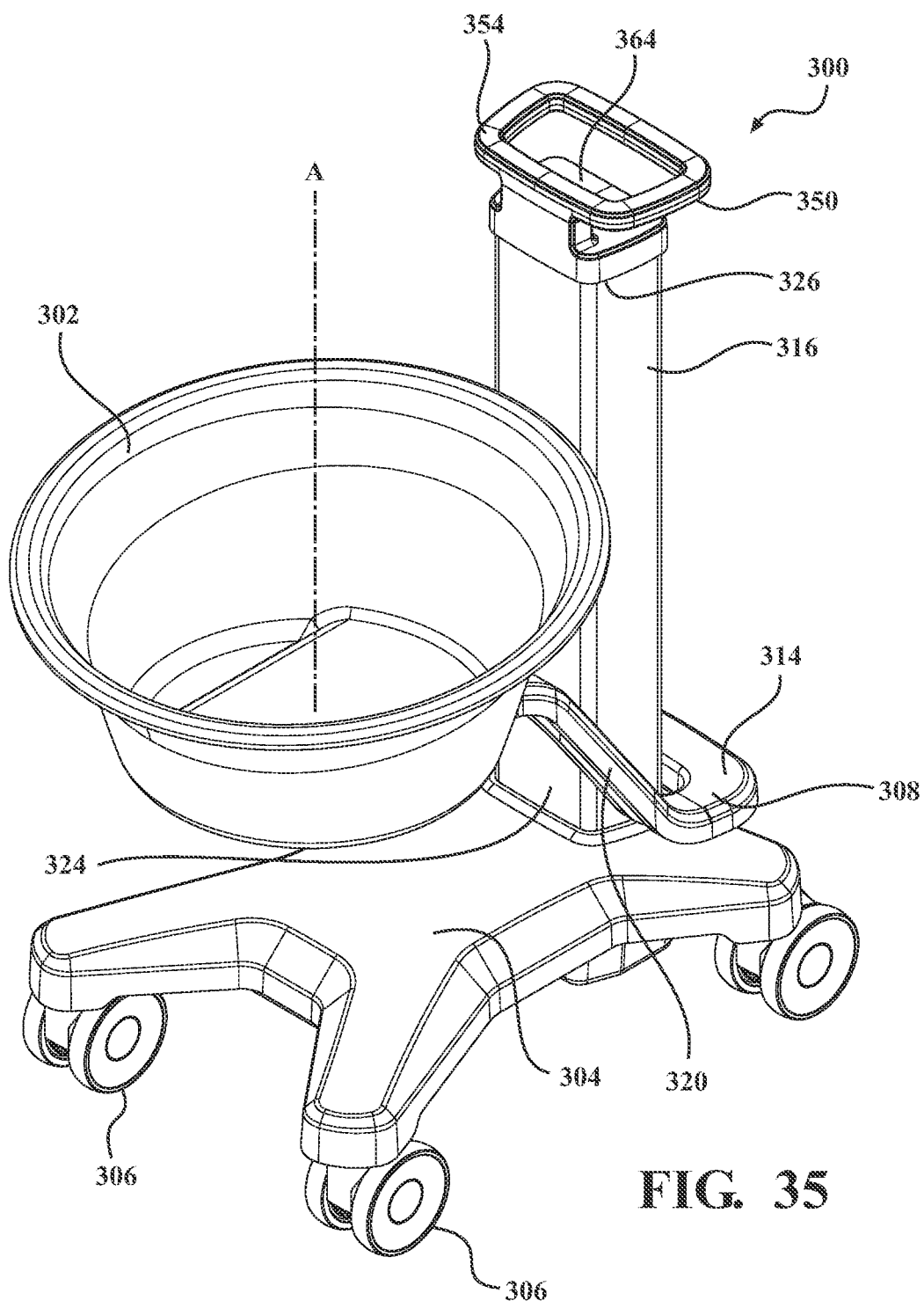
FIG. 35 is a perspective view of another example of a bucket having a receptacle in a minimum height.
Figure 36:
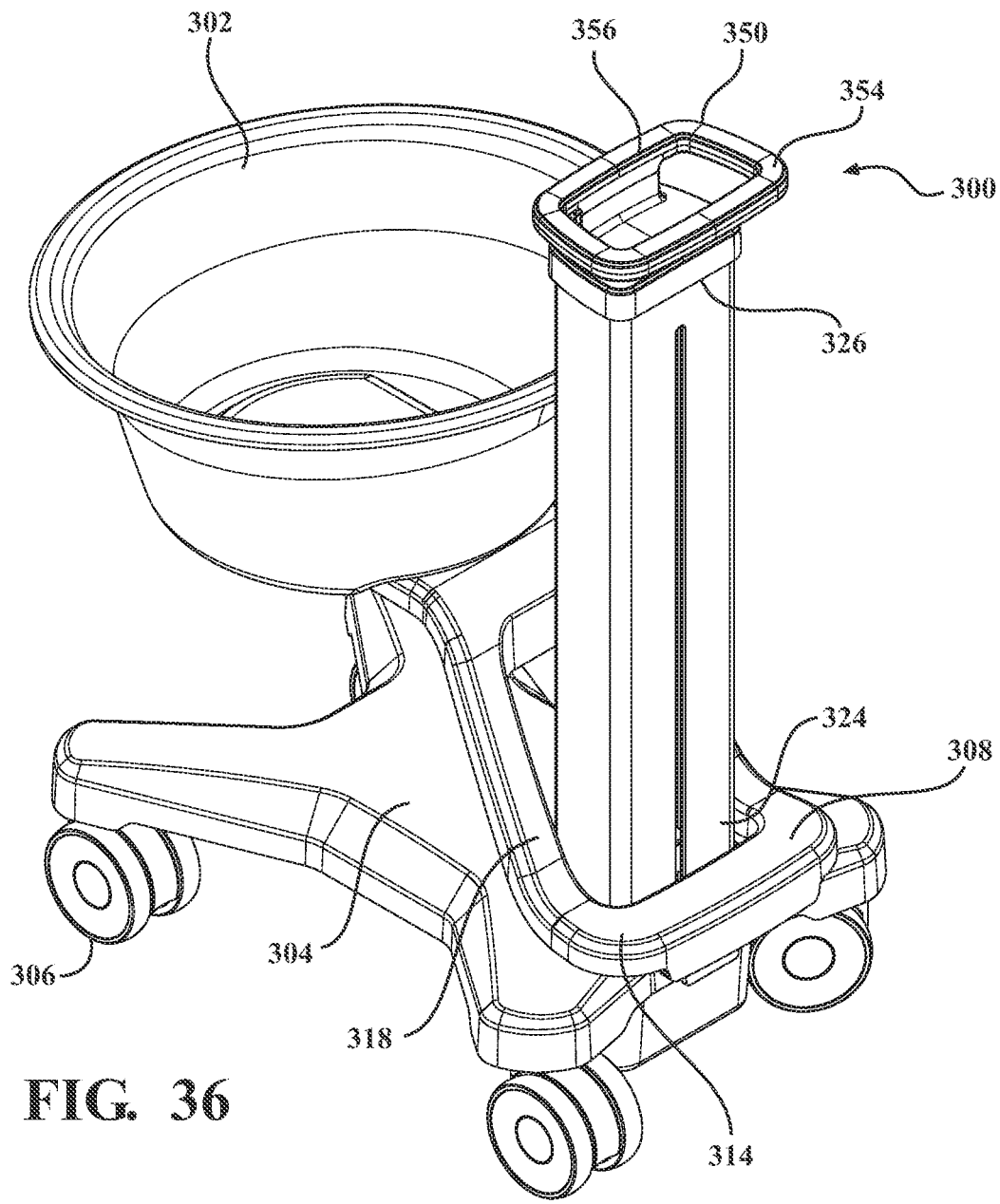
FIG. 36 is a rear perspective view of the bucket having the receptacle in the minimum height.

Referring to FIGS. 31-44, in operation, the receptacle 102 is in the minimum height (see FIG. 31 in phantom) corresponding with the carrier 108 being in the relatively low position (FIGS. 1-7) and the lifting member 150 being in the lowered position. When desired for the receptacle 102 to be in the maximum height, the user would engage the handle 156 of the lifting member 150 and lift the handle 156 vertically to move the handle 156 to the raised position. When the handle 156 is lifted, the stop member 160 of the lifting member 150 engages the underside of the carrier 108 to move the carrier 108 to the relatively high position (FIGS. 8-18). When the carrier 108 reaches the relatively high position (FIGS. 8-18), corresponding with the receptacle 102 being in the maximum height, the retainer 152 engages the carrier 108 to retain the carrier 108 in the relatively high position (FIGS. 8-18). Once the retainer 152 and the carrier 108 are engaged, i.e., the carrier 108 is retained in the relatively high position (FIGS. 8-18), the user may release the handle 156 of the lifting member 150 which allows the lifting member 150 to slide back through the support member 116 and return to the lowered position while the receptacle 102 remains in the maximum height (see FIG. 32). When desired, the user can engage the exterior engagement surface 164 (see FIG. 33) which actuates the engagement member to engage the interior engagement surface 170 which moves the piston to release the carrier 108 from the retainer 152. The action of engaging the exterior engagement surface 164 when the handle 156 is in the lowered position returns the receptacle 102 to the minimum height and the carrier 108 to the lowered position (see FIG. 34).

Referring now to the example shown in FIGS. 21-30, a bucket 200 is shown. The bucket 200 illustrated in FIGS. 21-30, may include the same features as shown in the bucket 100 illustrated in FIGS. 1-20, and as described above including but not limited to a receptacle 202, a base 204, a support member 216, a carrier 208, and a lifting member 250 similar to and including the features described above with respect to the corresponding receptacle 102, base 104, support member 116, carrier 108, and lifting member 150. However, the bucket 200 illustrated in FIG. 21 includes a carrier 208 configured such that the carrier 208 and a retainer 252 are mechanically coupled to one another when the carrier 208 is in the relatively high position.

Figure 30:
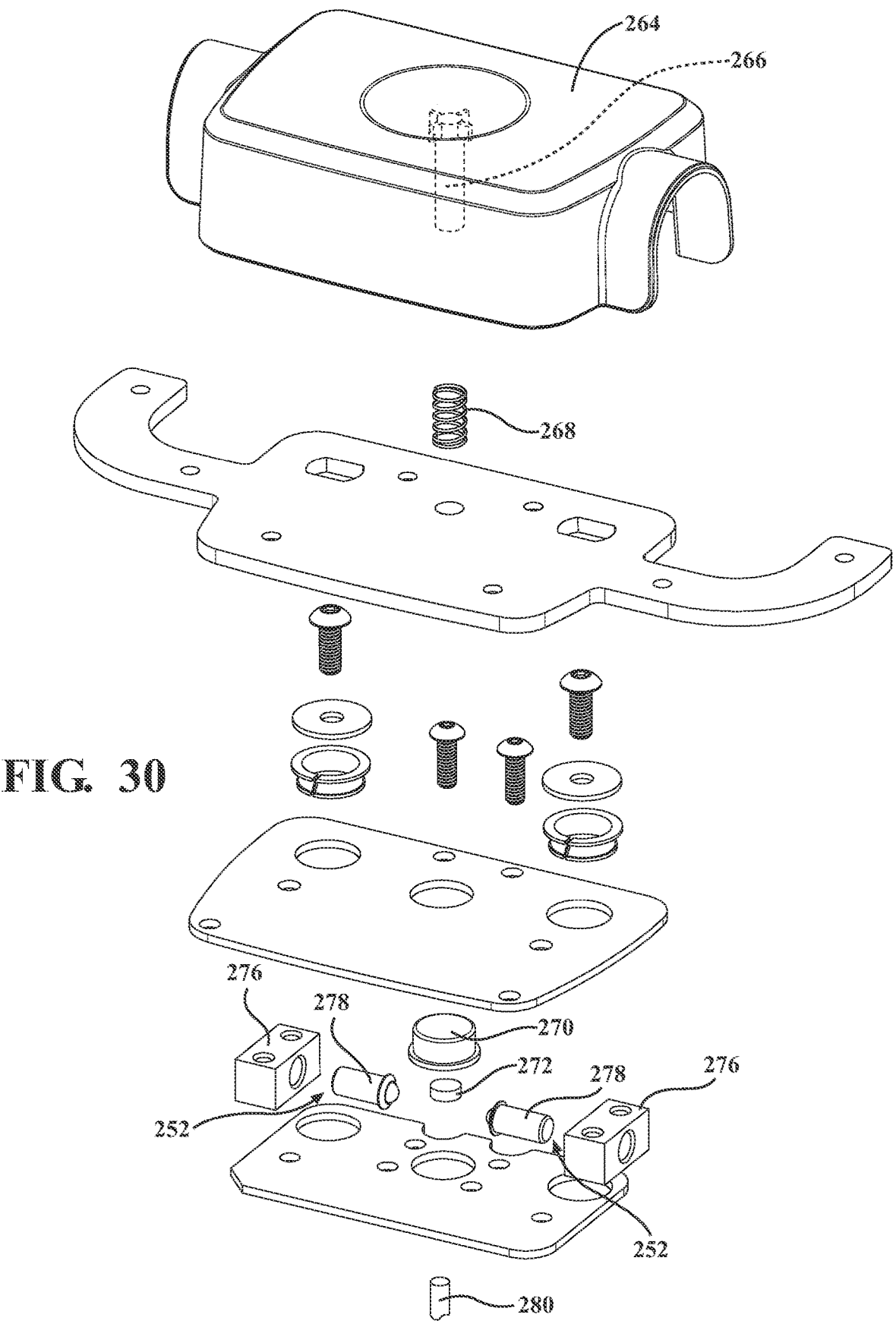
FIG. 30 is an exploded view of an exterior engagement surface of the lifting member and an interior engagement surface of a support member of the bucket of FIG. 21.

More specifically, the retainer 252 includes a first coupling member and the carrier includes a second coupling member. In the example shown in FIGS. 21-30, and as best illustrated in FIGS. 23, 27, 29, and 30, the first coupling member is one or more ball-nose plungers 276. In the example shown in FIGS. 21-30, the second coupling member is a rod 280 having a detent 282 configured to be engaged by the one or ball-nose plungers 276 to retain the carrier 208 in the relatively high position (FIGS. 8-18). As illustrated in FIG. 30, the bucket 200 may include a plurality of ball-nose plungers configured to engage the rod 280. In this example, similar to the magnetic coupling example described above with respect to FIGS. 1-20, when the piston 272 is moved from the rest position to the engaged position, the piston 272 engages the rod 280 with enough force to decouple the first and second coupling members which allows the carrier 208 to return to the relatively low position. With respect to the automatic decoupling feature described above with respect to FIGS. 1-20, the carrier 208 and the retainer 252 may similarly be configured to automatically decouple from one another when contents of the receptacle 202 has a mass greater than a predetermined mass. In the example shown in FIGS. 21-30, when the mass of the contents of the receptacle 202 reach the predetermined mass, the rod 280 is configured to be disengaged from the ball-nose plunger 276 due to the mass of the contents of the receptacle and the receptacle 202 is returned to the minimum height. Various other mechanical couplings have also been contemplated.

Referring now to the example shown in FIGS. 35-53, a height-adjustable stand or bucket 300 is shown. The bucket 300 illustrated in FIGS. 35-53, may include the same features as shown in the bucket 100 illustrated in FIGS. 1-20 and/or in the bucket 200 illustrated in FIGS. 21-30, and as described above including but not limited to a receptacle 302, a base 304, a support member 316, a carrier 308, and a lifting member 350 similar to and including the features described above with respect to the corresponding receptacle 102, 202, base 104, 204, support member 116, 216, carrier 108, 208 and lifting member 150, 250. Similar to the bucket 200 illustrated in FIG. 21, the bucket 300 illustrated in FIGS. 35-53 includes a carrier 308 configured such that the carrier 308 and a retainer 352 are mechanically coupled to one another when the carrier 308 is in the relatively high position.

Figure 37:
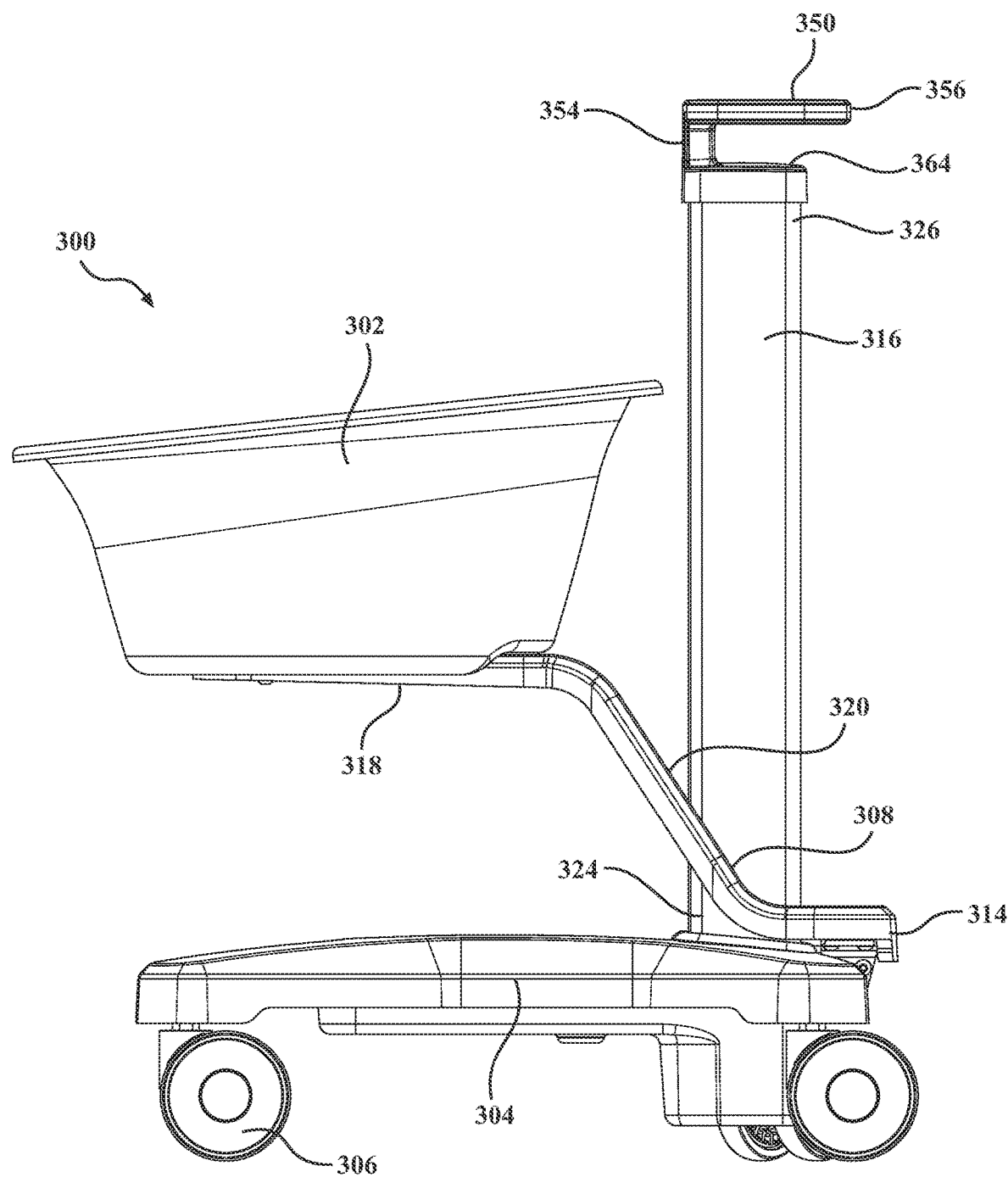
FIG. 37 is a side view of the bucket having the receptacle in the minimum height and having a lifting member in a lowered position.
Figure 38:
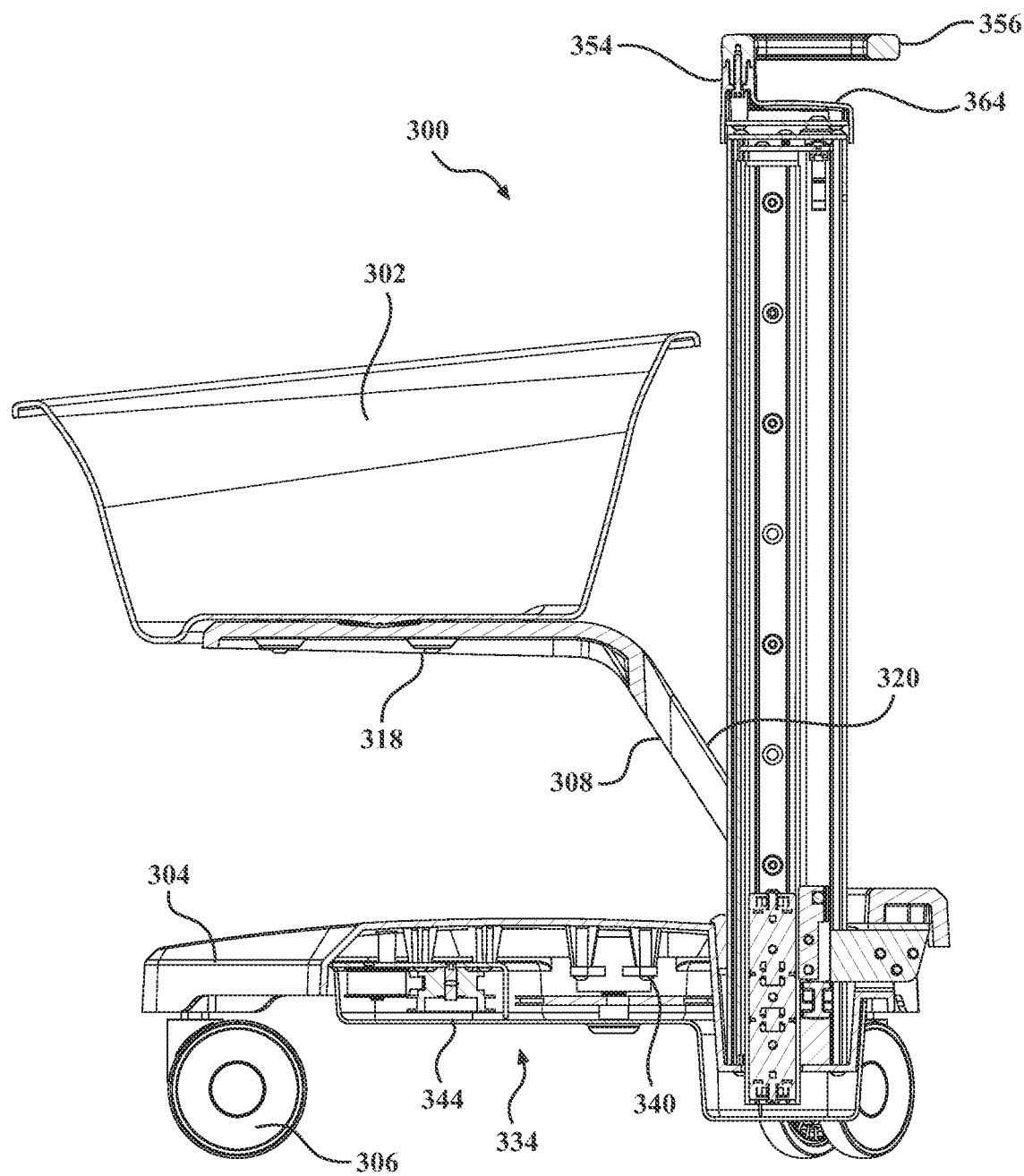
FIG. 38 is a sectional side view of the bucket having the receptacle in the minimum height and having the lifting member in the lowered position.
Figure 39:
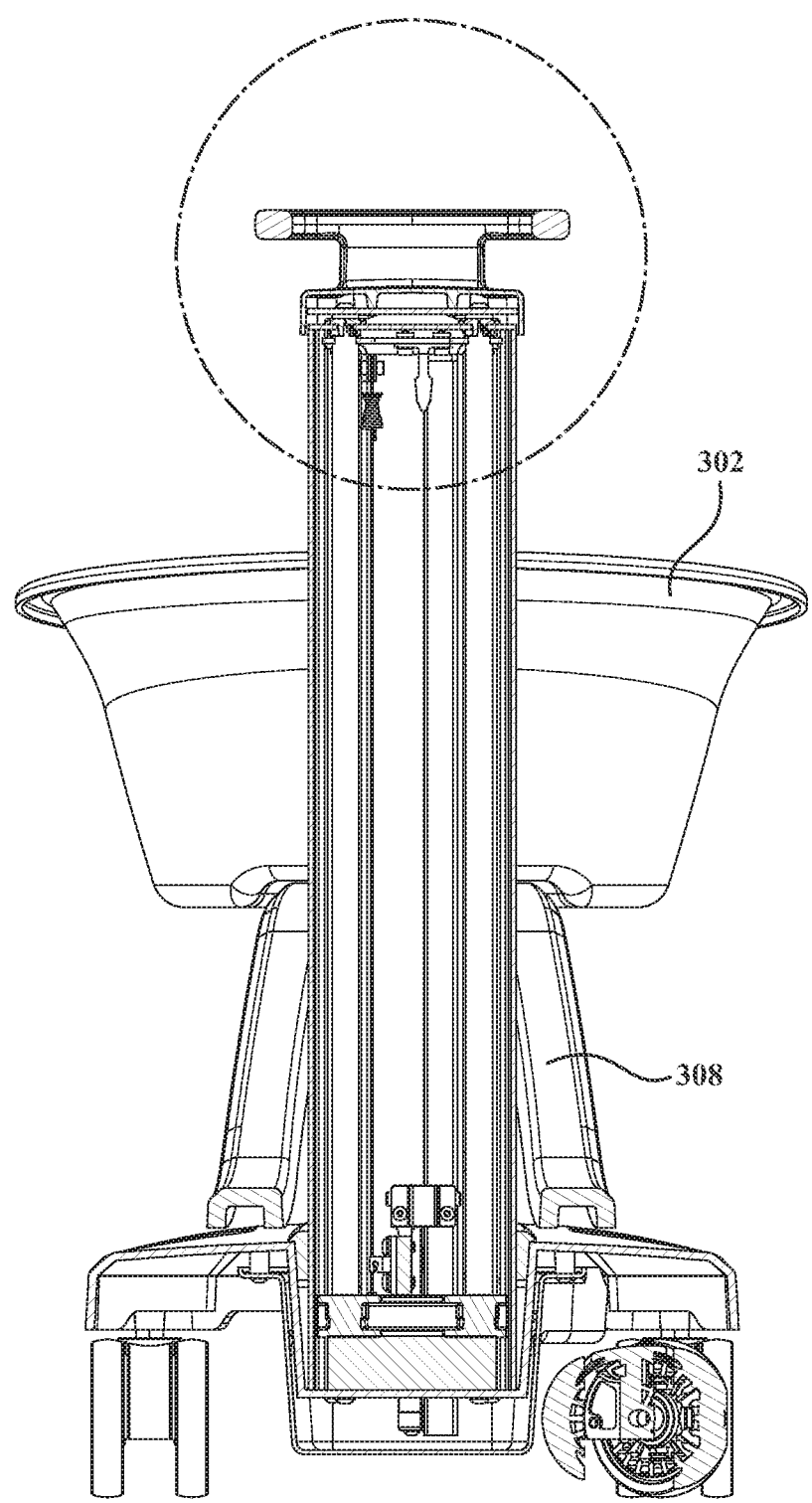
FIG. 39 is a sectional rear view of the bucket having the receptable in the minimum height and having the lifting member in the lowered position.

As best illustrated in FIG. 37, the lifting member 350 of the bucket 300 may include a handle 356 disposed on an upper end of the lifting member 350. In one example, the handle 356 is disposed spaced from and above an exterior engagement surface 364. Having the handle 356 disposed above the exterior engagement surface 364 allows the axis of the handle 356 to be closer to cylinders 362 of the lifting member 350 in order to prevent undesirable lifting of wheels 306 during movement of the lifting member 350 by a user though use of the handle 356.

Figure 40:
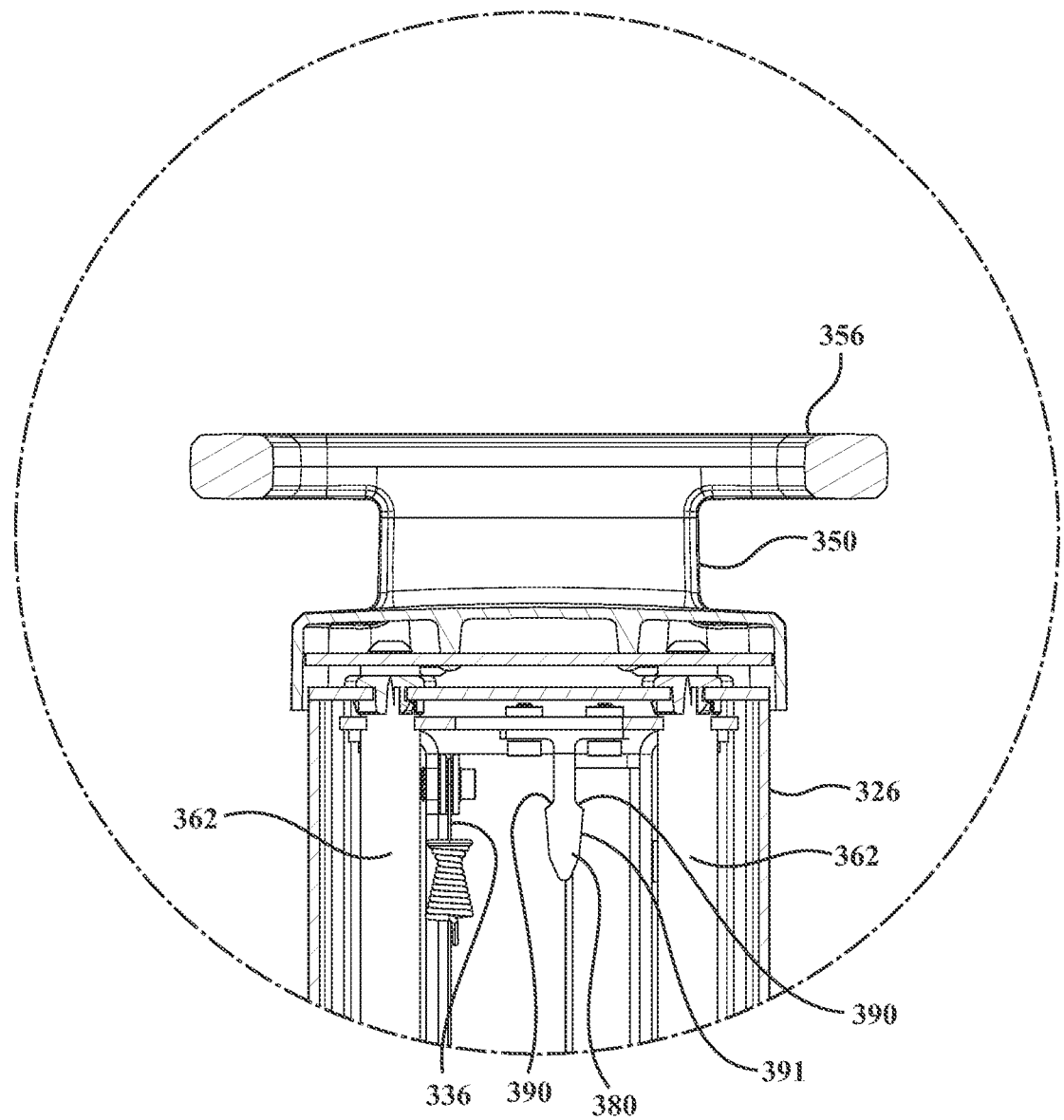
FIG. 40 is a magnified portion of FIG. 39.
Figure 53:
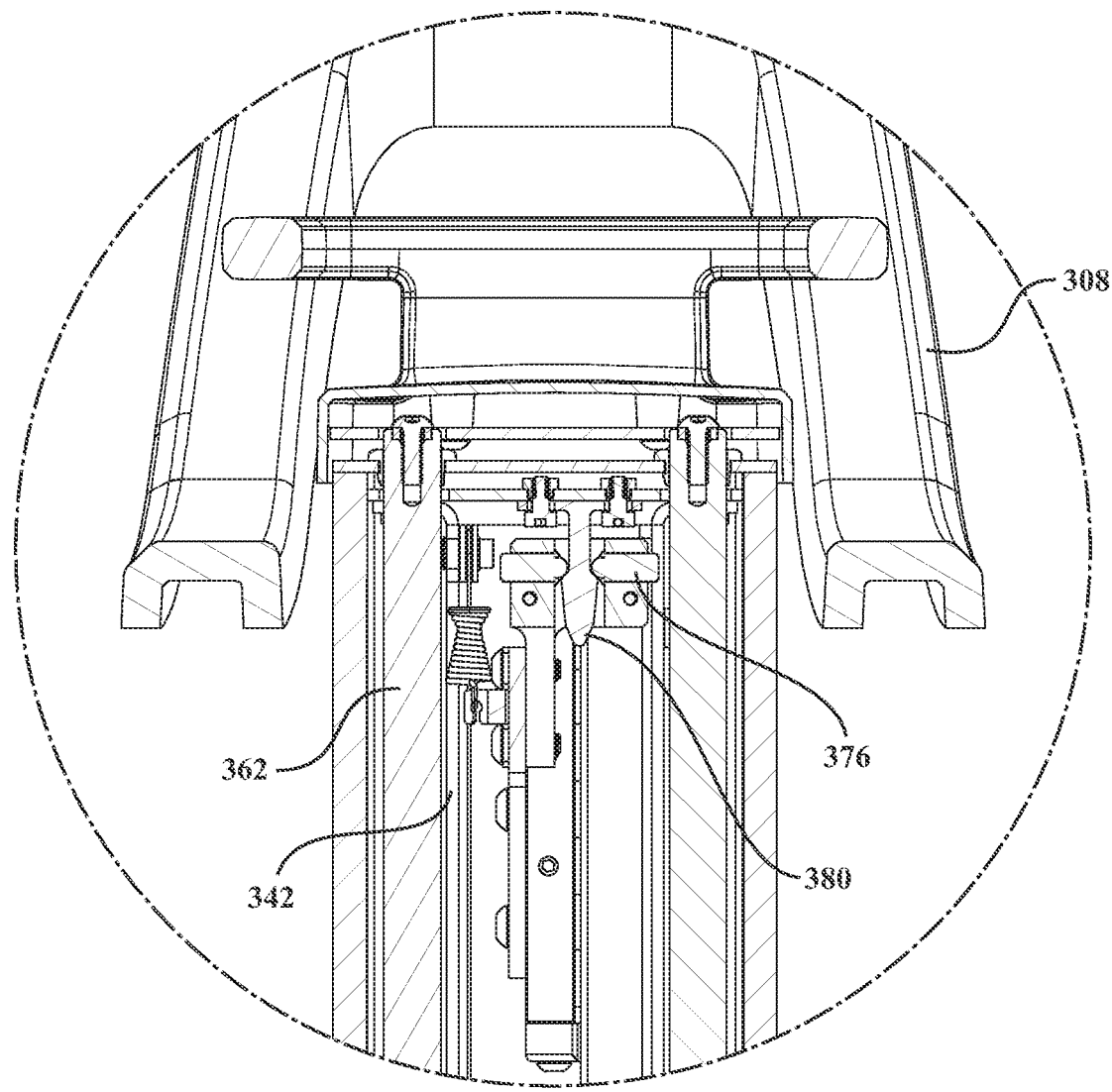
FIG. 53 is a magnified view of a portion of FIG. 52.

As best illustrated in FIGS. 40, 46, and 53, the retainer 352 includes a first coupling member and the carrier 308 includes a second coupling member and a least one of the first coupling member and the second coupling member engage one another to retain the carrier 308 in the relatively high position. The engagement of the first and second coupling members further defines a force between the first and second coupling members. Moreover, one of the first and second coupling member comprise a rod 380 including a shoulder 382 configured to be engaged with the other of the first and second coupling members. The rod 380 may also include at least one ramped surface 390 disposed below the shoulder 382 along the axis A. In other words, in the example shown in FIGS. 40, 46, and 53, the first coupling member is the rod 380 including the shoulder 382. However, it is also contemplated that the second coupling member may be the rod 380 including the shoulder 382. In the example best illustrated in FIGS. 40, 46, and 53 the second coupling member includes at least one ball-nose plunger 376 configured to be engaged with the shoulder 382 of the rod 380 to retain the carrier 308 in the relatively high position. However, it is also contemplated that the first coupling member may be the ball-nose plunger 376. In operation, the ball-nose plunger 376 may slide along the ramped surface 390 of the rod 380 during movement of the carrier 308 from the relatively low position to the relatively high position. It is also contemplated that the ball-nose plunger 376 may be spring loaded to assist the sliding movement of the ball-nose plunger 376 along the ramped surface 390 of the rod 380. In the example shown in FIG. 40, the bucket 300 includes two ball-nose plungers 376, however, any number of ball-nose plungers 376 may be used. In one example, the rod 380 extends to a narrow tip configured to provide alignment to the carrier during movement of the carrier 308 from the relatively low position to the relatively high position. The ramped surface 390 typically has a shallow angle, i.e. an angle less than 45 degrees. The shallow angle of the ramped surface 390 allows the carrier 308 to be moved along the rod 390 and into the relatively high position using a force less than the force necessary to lift a portion of the base 304 or wheels 306 off of the ground. The shallow angle may continue from the narrow tip of the rod 380 to the shoulder 382. However, it is also contemplated that the angle may change from the shallow angle of the ramped surface 390 to a second ramped 391 surface having a second angle. The second ramped surface 391 is disposed between the ramped surface 390 and the shoulder 382 and may be any angle which would allow the carrier 308 to be moved along the rod 390 and into the relatively high position using a force less than the force necessary to lift a portion of the base 304 or wheels 306 off of the ground.

In order to decouple the rod 380 and the ball-nose plunger 376, a user may exert a force on the carrier 308 which is greater than the force defined between the rod 380 and the ball-nose plunger 376 such that the ball-nose plunger 376 and the rod 380 are configured to be repeatability decoupled, i.e. without breaking or damaging either the rod 380 or the ball-nose plunger 376. The bucket 300 is configured such that the exertion of a force by the user may be done on any portion of the carrier 308 or the receptacle 302. In other words, the first coupling member and the second coupling member are designed to each able to withstand a force greater than the force securing the rod 380 and the ball-nose plunger 376 when the carrier 308 is retained in the relatively high position to allow repeated decoupling by a user without damage to any component.

Referring still to the example shown in FIGS. 35-53, the bucket 300 also includes a dampening assembly 334, similar to the dampening assembly 134 described above with respect to the example shown in FIGS. 1-20. More specifically, the dampening assembly 334 is configured to provide controlled movement of the carrier along a length of the axis A between the relatively high position and the relatively low position. In one example, the dampening assembly 334 is configured to provide a dampening force which is within 20% of the force between the retainer 352 and the carrier 308. It is also contemplated that the dampening assembly 334 may be configured to provide a dampening force which is within 30% of the force between the retainer 352 and the carrier 308. In one example, the dampening assembly 334 is a one-way dampening assembly. However, a two-way dampening assembly has also been contemplated. The dampening assembly 334 includes a tension member 342 coupled to the carrier 308 and a dampener 340 coupled to the base 304. In one example, the dampening assembly 334 may also include a pulley 338 coupled to one of the base 304 or the support member and coupled between the carrier 308 and the dampener 340 such that the pulley 338 is configured to change direction of the tension member 342 between the carrier 308 and the dampener 340. In another example, the dampener 340 may be a radial dampener. In one example, the dampener 340 is coupled to the base 304 and is positioned below an upper most surface of the base 304, i.e. on an underside of the base 304. The coupling of the dampener 340 below the upper most surface of the base 304 allows for a maximum travel distance of the carrier 308 between the relatively high position and the relatively low position providing a comfortable working position with the high position of the receptacle 302 while still allowing the entire bucket 300 to be below the sterile zone when the receptacle 302 is in the low position. Coupling of the dampener 340 below the upper most surface of the base 304 also provides protection of the dampener 340 from fluids or other contaminants.

Figure 41:
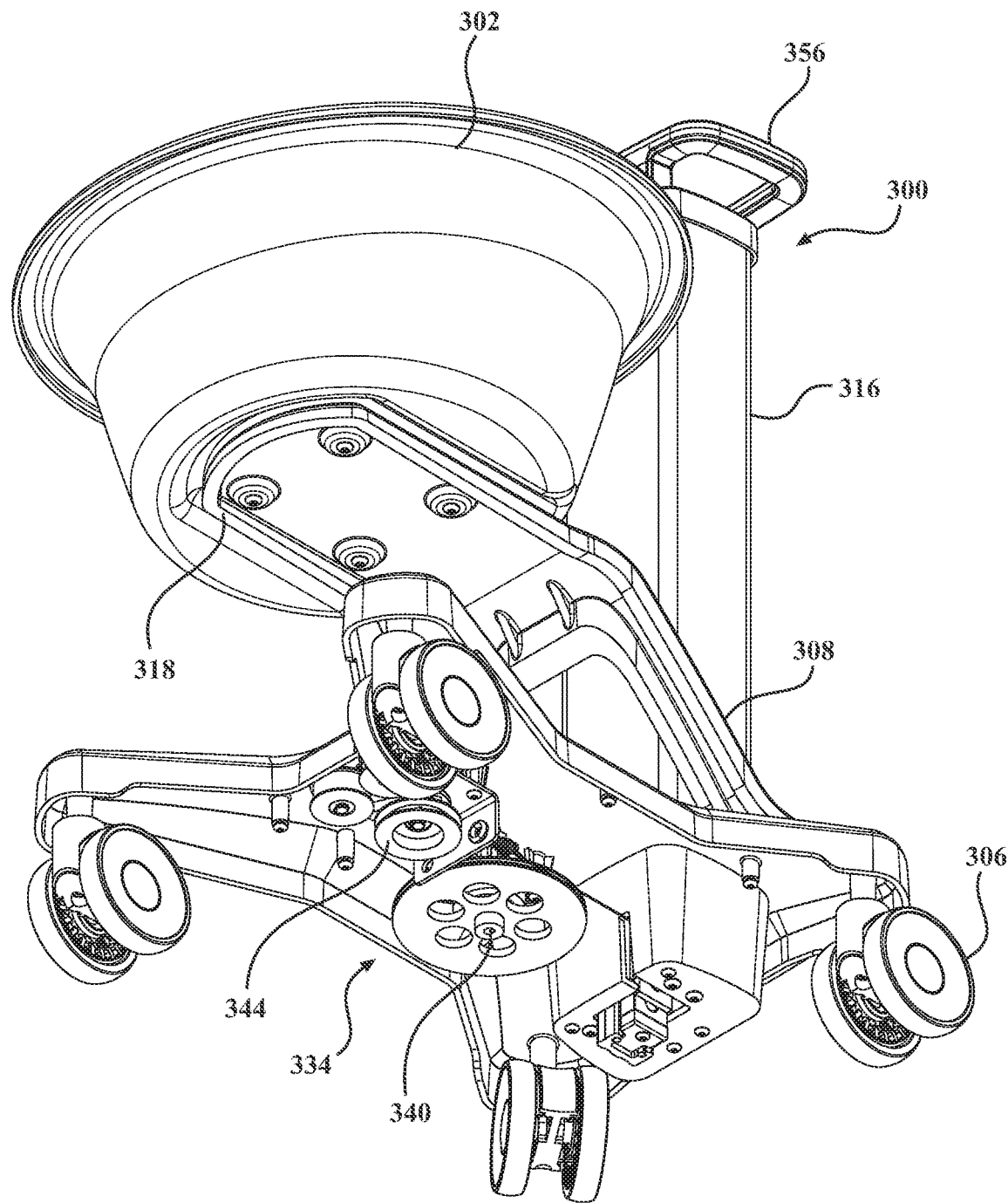
FIG. 41 is a front perspective view of the underside of the bucket having the receptacle in the minimum height and having the lifting member in the lowered position.
Figure 42:
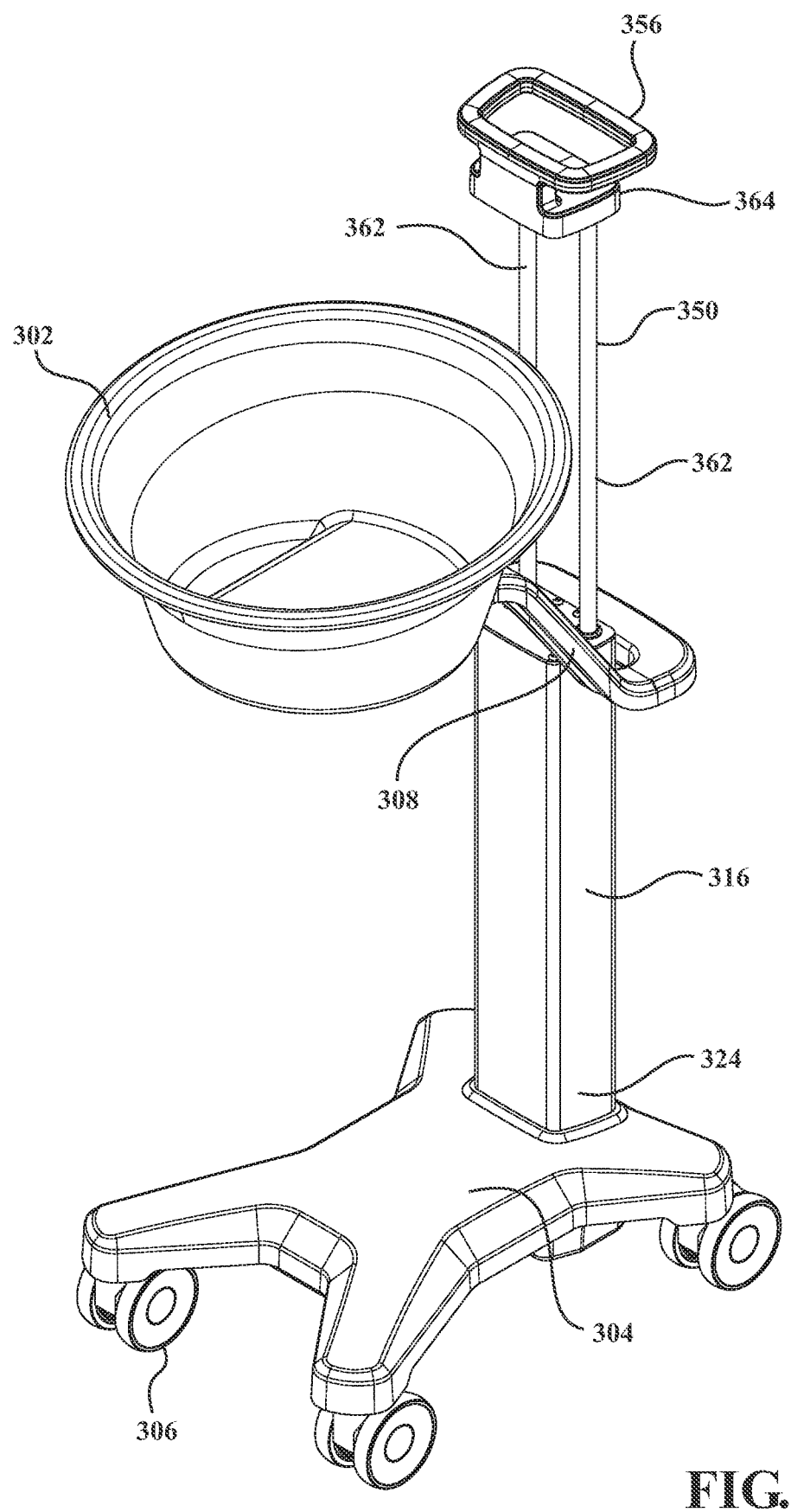
FIG. 42 is a front perspective view of the bucket having the receptacle in a maximum height and having the lifting member in a raised position.
Figure 43:
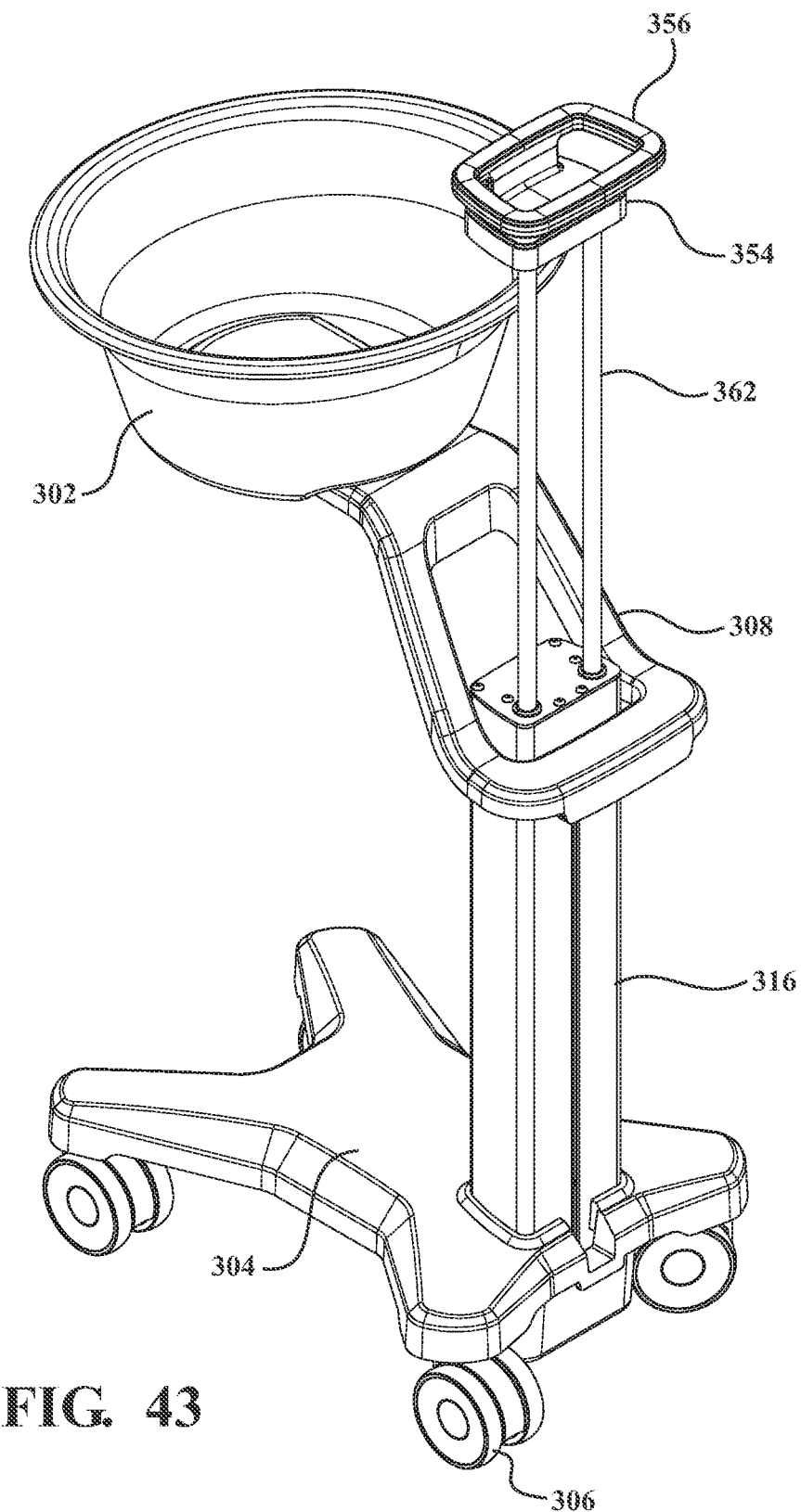
FIG. 43 is a rear perspective view of the bucket having the receptacle in the maximum height and having the lifting member in a raised position.
Figure 44:
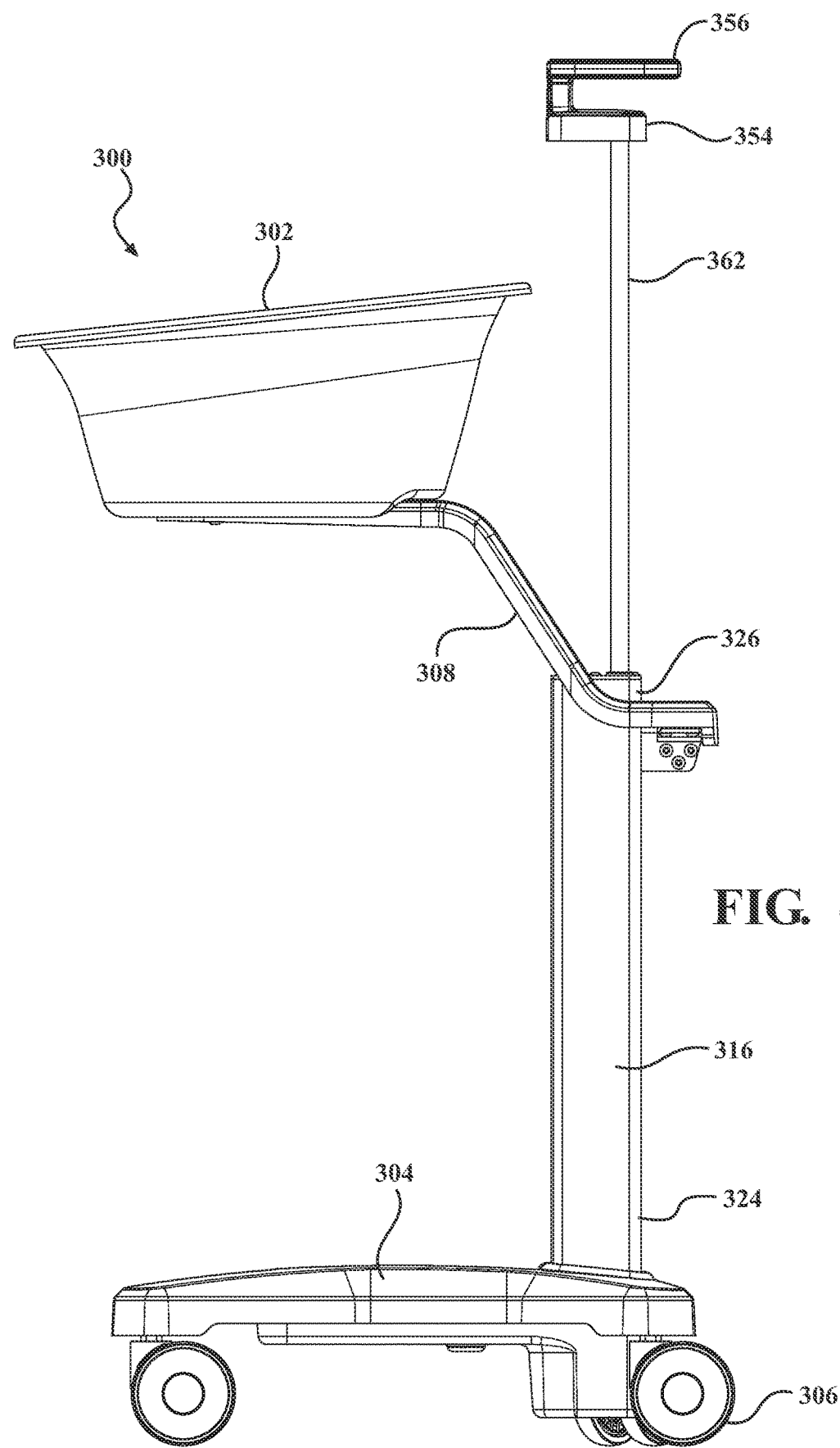
FIG. 44 is a side view of the bucket having the receptacle in the maximum height and having the lifting member in a raised position.

As best shown in FIG. 41, the dampening assembly 334 also includes a winder 344, similar to the winder 144 as described above, which is coupled to the tension member 342 and configured to wind extra slack of the tension member 342 during movement of the carrier 308 between the relatively high position and the relatively low position.

In operation, the dampening assembly 334 defines a first dampening force when the carrier is in the relatively high position and the user has decoupled the carrier 308 and the retainer 352, i.e. the carrier 308 and the retainer 352 are in a decoupled configuration. When the carrier 308 is decoupled, the tension member 342 coupled to the carrier 308 and the dampener 340 rotates the spool portion to provide an opposite dampening force to dampen the force of the carrier 308. The tension member 342 extends from the carrier to the pulley 338, where the tension member 342 changes direction before extending to the dampener 340. In one example, the dampener 340 is coupled to the tension member 342 by a plurality of circumferences of the tension member 342 being spooled around the dampener 340. The tension member 342 then extends to the winder 344 where extra slack is wound up by the winder 344 during movement of the carrier 308 from the relatively high position to the relatively low position. A second dampening force is defined at a second height, which is higher than the relatively low position and lower than the relatively high position. The second dampening force is within 15% of the second dampening force such that the dampening assembly 334 is configured to provide continuous damping to movement of the carrier 308 along the length of the axis A from the relatively high position to the relatively low position.

Having the lifting member 150 configured to be the lowered position when the carrier 108 is in the relatively high position (FIGS. 8-18) and when the carrier 108 is in the relatively low position (FIGS. 1-7), as described above and as illustrated in FIGS. 3-5, provides an easily adjustable bucket 100, 200, 300 with manual actuation which allows the bucket 100, 200, 300 to be unpowered which prevents failure due to battery life and keeps the surgical floor free from unnecessary wires. Moreover, the bucket 100, 200, 300 as described herein provides the bucket 100, 200, 300 with smooth and easy to clean surfaces which allows for quick and easy decontamination between uses. The height-adjustable stand 100, 200, 300 is configured such that the base 104, 204, 304 can be positioned closed to a support of an operating room table or bed and position the carrier 108, 208, 308 at an optimal height when the carrier 108, 208, 308 is in the relatively high position. When the carrier is in the relatively high position, the upper most portion of the receptacle 102, 202, 302, which is coupled to the carrier 108, 208, 308, should be located outside the sterile zone (below the waist of operating room personnel). In other words, when the carrier 108, 208, 308 is in the relatively high position, the upper most portion of the receptacle has a height of no more than 36", and yet the receptacle should have a depth of at least 4-8" to allow suitable retention of surgical objects to be collected.

The height-adjustable stand 100, 200, 300 may also be configured to provide for an advantageous relatively low position of the carrier 108, 208, 308 which also places the upper most portion of the receptacle 102, 202, 302 outside the sterile zone. It should be appreciated that the maximum height of the receptacle should be at least 12" greater than the minimum height of the receptacle. The minimum height of upper most portion of the receptacle should not exceed 24", 18", or 12" when the carrier 108, 208, 308 and/or the receptacle 102, 202, 302 are at their minimum heights and when the receptacle has a depth of at least 4-8".

When the carrier 108, 208, 308 is in the relatively high position, which therefore positions the receptacle 102, 202, 302 at its maximum height, it is desirable that the lifting member 150, 250, 350 is also out of the way of the healthcare professionals in the operating room. In other words, it is desirable that the lifting member 150, 250, 350 can be at its minimum height or lowered position while the receptacle 102, 202, 302 and carrier 108, 208, 308 at their maximum heights. This allows the carrier 108, 208, 308 and if used, the receptacle 102, 202, 302, to be placed adjacent to the area of interest (at a raised position) without having the lifting member 150, 250, 350 interfering. More particularly, in certain configurations, the upper most surface of the lifting member 150, 250, 350 is capable of being positioned below the upper most portion of the carrier 108, 208, 308 and/or the bottommost surface of receptacle 102, 202, 302 when the receptacle 102, 202, 302 and/or carrier 108, 208, 308 are at a maximum height (see FIG. 48). The minimum height of the lifting member 150, 250, 350 when the lifting member 150, 250, 350 is in the lower position is configured not to exceed 30" height.

The dampening assembly 134, 234, 334 advantageously provides for dampening and let allows a relatively low minimum height of the upper most portion of the receptacle 102, 202, 302. This is due to the use of a rotary dampener and due to the arrangement of the dampener 140, 240, 340 on the underside of the base 104, 204, 304. This ensures that dampening assembly 134, 234, 334 does not compromise the range of motion of the receptacle 102, 202, 302 and/or the carrier 108, 208, 308. In other words, this ensures that the carrier 108, 208, 308 and/or the receptacle 102, 202, 302 can be positioned at a desirable minimum height and yet the stand 100, 200, 300 still provides for dampening as the carrier 108, 208, 308 and/or receptacle 102, 202, 302 descends from a position above the minimum height (such as the maximum height) to the minimum height.

It is also desirable that the height-adjustable stand 100, 200, 300 is free of any pneumatic or fluid cylinders in some configurations. Further still, it is contemplated that the height-adjustable stand 100, 200, 300 may be free of any electronic components.

It will be further appreciated that the terms "include," "includes," and "including" have the same meaning as the terms "comprise," "comprises," and "comprising."

Several examples have been discussed in the foregoing description. However, the examples discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

CLAUSES FOR ADDITIONAL DISCLOSURE

The present disclosure also comprises the following clauses, with specific features laid out in dependent clauses that may specifically be implemented as described in greater detail with reference to the configurations and drawings above.

I. A height-adjustable bucket adapted to carry a medical object, said bucket comprising: a receptacle for carrying the medical object; a base; a support member coupled to said base; a carrier movably coupled to said support member and for supporting said receptacle, wherein said carrier is configured to move between a relatively high position and a relatively low position along an axis defined by said support member; a lifting member slidably coupled to said carrier and configured to move between a raised position and a lowered position, said lifting member comprising: a first end portion comprising a handle; and a second end portion, opposite said first end portion, comprising a stop member configured to operatively engage said carrier; and a retainer selectively coupling said carrier to said support member and configured to selectively retain said carrier in said relatively high position; and wherein said lifting member is configured to be in said lowered position when said carrier is in said relatively high position and when said carrier is in said relatively low position; and wherein said stop member is spaced from said carrier when said lifting member is in said lowered position and when said carrier is in said relatively high position.

II. The height-adjustable bucket of clause I, wherein said support member defines a rail, and said carrier includes a carriage assembly movably coupled to said rail.

III. The height-adjustable bucket of any one of clauses I or II, further comprising a dampening assembly configured to provide controlled movement of said carrier.

IV. The height-adjustable bucket of clause III, wherein said dampening assembly comprises a pulley, a tension member, and a dampener, said tension member extending between said dampener and said carrier to assist in moving said carrier between said relatively high position and said relatively low position, said pulley facilitating a change in direction of said tension member between said dampener and said carrier.

V. The height-adjustable bucket of clause IV, wherein said dampening assembly is a single direction system such that said dampening assembly is configured to provide controlled movement of said carrier only from said relatively high position to said relatively low position.

VI. The height-adjustable bucket of any of clauses IV or V, wherein said dampener is a rotary dampener.

VII. The height-adjustable bucket of any of clauses IV-VI, wherein said dampener is coupled to an underside of said base.

VIII. The height-adjustable bucket of any of clauses I-VII, wherein said lifting member defines an exterior engagement surface and an engagement member, wherein said exterior engagement surface is configured to be activated by a user and said engagement member is configured to be moved from a first position to a second position upon activation of said exterior engagement surface to cause the carrier to be decoupled from said support member.

IX. The height-adjustable bucket of clause VIII, wherein said support member comprises an interior engagement surface configured to be actuated by said engagement member and a piston configured to selectively uncouple said retainer and said carrier to allow said carrier to move to said relatively low position upon actuation of said interior engagement surface by said engagement member.

X. The height-adjustable bucket of any of clauses I-IX, wherein said carrier and said retainer are magnetically coupled to each other when said carrier is in said relatively high position.

XI. The height-adjustable bucket of any one of clauses I-X, wherein said carrier and said retainer are mechanically coupled to each other when said carrier is in said relatively high position.

XII. A height-adjustable stand comprising: a medical device to be supported; a base; a support member coupled to said base, a carrier movably coupled to said support member and for supporting said medical device, wherein said carrier is configured to move between a relatively high position and a relatively low position along an axis defined by said support member; a lifting member slidably coupled to said carrier and configured to move between a raised position and a lowered position, said lifting member comprising: a first end portion comprising a handle; and a second end portion, opposite said first end portion, comprising a stop member configured to operatively engage said carrier; and a retainer selectively coupling said carrier to said support member and configured to selectively retain said carrier in said relatively high position; and wherein said lifting member is configured to be in said lowered position when said carrier is in said relatively high position and when said carrier is in said relativity low position; and wherein said stop member is spaced from said carrier when said lifting member is in said lowered position and when said carrier is in said relatively high position.

XIII The height-adjustable bucket of clause XII, wherein said support member defines a rail, and said carrier includes a carriage assembly movably coupled to said rail.

XIV. The height-adjustable stand of any of clauses XII or XIII, further comprising a dampening assembly configured to provide controlled movement of said carrier.

XV. The height-adjustable stand of clause XIV, wherein said dampening assembly comprises a pulley, a tension member, and a dampener, said tension member extending between said dampener and said carrier to assist in moving said carrier between said relatively high position and said relativity low position, said pulley facilitating a change in direction of said tension member between said dampener and said carrier.

XVI. The height-adjustable stand of any of clauses XIV or XV, wherein said dampening assembly is a single direction system such that said dampening assembly is configured to provide controlled movement of said carrier only from said relatively high position to said relatively low position.

XVII. The height-adjustable stand of any of clauses XV or XVI, wherein said tension member includes a constant force spring.

XVIII. The height-adjustable stand of any of clauses XV-XVII, wherein said dampener is disposed on an underside of said base.

XIX. The height-adjustable stand of any of clauses XII-XVIII, wherein said lifting member comprises an exterior engagement surface and an engagement member, wherein said exterior engagement surface is configured to be activated by the user and said engagement member is configured to be moved from a first position to a second position upon activation of said exterior engagement surface.

XX. The height-adjustable stand of clause XIX, wherein said support member comprises an interior engagement surface configured to be actuated by said engagement member and a piston configured to selectively uncouple said retainer and said carrier to allow said carrier to move to said relativity low position upon actuation of said interior engagement surface by said engagement member.

XXI. The height-adjustable stand of any of clauses XII-XX, wherein said carrier and said retainer are magnetically coupled when said carrier is in said relatively high position.

XXII. The height-adjustable stand of any of clauses XII-XXI, wherein said carrier and said retainer are mechanically coupled when said carrier is in said relatively high position.

XXIII. A height-adjustable bucket adapted to carry a medical object, said bucket comprising: a receptacle for carrying the medical object; a base; a support member coupled to said base; a carrier movably coupled to said support member and said carrier for supporting said receptacle, wherein said carrier is configured to move between a relatively high position and a relatively low position along an axis defined by said support member; and a retainer selectively coupling said carrier to said support member and configured to selectively retain said carrier in said relatively high position, wherein when said carrier is in said relatively high position and said retainer is coupling said carrier to said support member, said carrier and said retainer are configured to automatically decouple from one another when contents of said receptacle has a mass greater than a predetermined mass.

XXIV. The height-adjustable bucket of clause XXIII, wherein said retainer includes a first coupling member and said carrier includes a second coupling member and wherein at least one of said first coupling member and said second coupling member comprise magnetic material.

XXV. The height-adjustable bucket of clause XXIV, further comprising a lifting member slidably coupled to said carrier, said lifting member including a first end portion comprising a handle and a second end portion, opposite said first end portion.

XXVI. The height-adjustable bucket of clause XXV, wherein said lifting member comprises an exterior engagement surface and an engagement member, wherein said exterior engagement surface is configured to be activated by the user and said engagement member is configured to be moved from a first position to a second position upon activation of said exterior engagement surface.

XXVII. The height-adjustable bucket of clause XXVI, wherein said support member comprises an interior engagement surface configured to be actuated by said engagement member and a piston configured to selectively uncouple said retainer and said carrier to allow said carrier to move to said relativity low position upon actuation of said interior engagement surface by said engagement member.

XXVIII. The height-adjustable bucket of any one of clauses XXIII-XXVII, wherein said carrier and said retainer are magnetically coupled when said carrier is in said relatively high position.

XXIX. The height-adjustable bucket of any one of clauses XXIII-XXVIII, wherein said carrier and said retainer are mechanically coupled when said carrier is in said relatively high position.

XXX. The height-adjustable bucket of any one of clauses XXIII-XXIX, further comprising a dampening assembly configured to provide controlled movement of said carrier.

XXXI. The height-adjustable bucket of clause XXX, wherein said dampening assembly comprises a pulley, a tension member, and a dampener, said tension member extending between said dampener and said carrier to assist in moving said carrier between said relatively high position and said relativity low position, said pulley facilitating a change in direction of said tension member between said dampener and said carrier.

XXXII. The height-adjustable bucket of clause XXXI, wherein said retainer includes a first coupling member and said carrier includes a second coupling member and wherein at least one of said first coupling member and said second coupling member comprise magnetic material such that a magnetic force retains said carrier in said relatively high position, and wherein a force of said dampener is within 20% of said magnetic force between said retainer and said carrier.

XXXIII. The height-adjustable bucket of any one of clauses XXIII-XXXII, further comprising a base coupled to said support member, said base comprising wheels.

XXXIV. A height-adjustable medical stand comprising: a medical device to be supported; a base; a support member coupled to said base; a carrier movably coupled to said support member and said carrier for supporting said medical device, wherein said carrier is configured to move between a relatively high position and a relatively low position along an axis defined by said support member; and a retainer selectively coupling said carrier to said support member and configured to selectively retain said carrier in said relatively high position, wherein when said carrier is in said relatively high position and said retainer is coupling said carrier to said support member, said carrier and said retainer are configured to automatically decouple from one another when contents of said receptacle has a mass greater than a predetermined mass.

XXXV. The height-adjustable stand of clause XXXIV, wherein said retainer includes a first coupling member and said carrier includes a second coupling member and wherein at least one of said first coupling member and said second coupling member comprise magnetic material.

XXXVI. The height-adjustable stand of clause XXXV, further comprising a lifting member slidably coupled to said carrier, said lifting member including a first end portion comprising a handle and a second end portion, opposite said first end portion.

XXXVII. The height-adjustable stand of clause XXXVI, wherein said lifting member defines an exterior engagement surface and an engagement member, wherein said exterior engagement surface is configured to be activated by the user and said engagement member is configured to be moved from a first position to a second position upon activation of said exterior engagement surface.

XXXVIII. The height-adjustable stand of clause XXXVII, wherein said support member comprises an interior engagement surface configured to be actuated by said engagement member and a piston configured to selectively uncouple said retainer and said carrier to allow said carrier to move to said relativity low position upon actuation of said interior engagement surface by said engagement member.

XXXIX. The height-adjustable stand of any one of clauses XXXIV-XXXVIII, wherein said carrier and said retainer are magnetically coupled when said carrier is in said relatively high position.

XL. The height-adjustable stand of any one of clauses XXXIV-XXXIX, wherein said carrier and said retainer are mechanically coupled when said carrier is in said relatively high position.

XLI. The height-adjustable stand of clause XXXVII, wherein said lifting member further comprises a biasing member configured to return said engagement member back to said first position from said second position.

XLII. The height-adjustable stand of any one of clauses XXXIV-XLI, further comprising a dampening assembly configured to provide controlled movement of said carrier, said dampening assembly comprises a pulley, a tension member, and a dampener, said tension member extending between said dampener and said carrier to assist in moving said carrier between said relatively high position and said relativity low position, said pulley facilitating a change in direction of said tension member between said dampener and said carrier.

XLIII. The height-adjustable stand of clause XLII, wherein said retainer includes a first coupling member and said carrier includes a second coupling member and wherein at least one of said first coupling member and said second coupling member comprise magnetic material such that a magnetic force retains said carrier in said relatively high position, and wherein a force of said dampener is tuned to exert a dampening force of a substantially equal magnitude to said magnetic force between said retainer and said carrier.

XLIV. The height-adjustable stand of any one of clauses XXXIV-XLIII, further comprising a base coupled to said support member, said base comprising wheels.

XLV. A height-adjustable bucket adapted to carry a medical object, said bucket comprising: a receptacle for carrying the medical object; a base; a support member coupled to said base; a carrier movably coupled to said support member and for supporting said receptacle, wherein said carrier is configured to move between a relatively high position and a relatively low position along an axis relative to said relatively high position; a retainer selectively coupling said carrier and said support member and configured to retain said carrier in said relatively high position; and a lifting member coupled to said carrier and comprising a first end portion defining an exterior engagement surface, and an engagement member, wherein said exterior engagement surface is configured to be activated by the user, and said engagement member is configured to be moved from a first position to a second position upon activation of the exterior engagement surface; and wherein said support member defines an interior engagement surface configured to be actuated by movement of said engagement member into said second position, and said support member comprises a piston configured to selectively uncouple said carrier and said support member to allow said carrier to move to said relatively low position upon actuation of the interior engagement surface by said engagement member.

XLVI. The height-adjustable bucket of clause XLV, wherein said interior engagement surface is not visible when said lifting member is in said lowered position.

XLVII. The height-adjustable bucket of any one of clauses XLV or XLVI, wherein a user engagement of said interior engagement surface does not actuate movement of said carrier from said relatively high position to said relatively low position.

XLVIII. The height-adjustable bucket of any one of clauses XLV-XLVII, wherein said retainer includes a first coupling member and said carrier includes a second coupling member and wherein at least one of said first coupling member and said second coupling member comprise magnetic material.

XLIX. The height-adjustable bucket of any one of clauses XLV-XLVIII, wherein said carrier and said retainer are mechanically coupled when said carrier is in said relatively high position.

L. The height-adjustable bucket of any one of clauses XLV-XLIX, wherein said carrier and said retainer are magnetically coupled when said carrier is in said relatively high position.

LI. The height-adjustable bucket of any one of clauses XLV-L, wherein said lifting member further comprises a biasing member configured to return said engagement member back to said first position from said second position.

LII. The height-adjustable bucket of any one of clauses XLV-LI, further comprising a dampening assembly configured to provide controlled movement of said carrier.

LIII. The height-adjustable bucket of clause LII, wherein said dampening assembly comprises a pulley, a tension member, and a dampener, said tension member extending between said dampener and said carrier to assist in moving said carrier between said relatively high position and said relatively low position, said pulley facilitating a change in direction of said tension member between said dampener and said carrier.

LIV. The height-adjustable bucket of any one of clauses LII or LIII, wherein said dampening assembly is a single direction system such that said dampening assembly is configured to provide controlled movement of said carrier only from said relatively high position to said relatively low position.

LV. The height-adjustable bucket of any one of clauses LIII or LIV wherein said dampener is a rotary dampener.

LVI. The height-adjustable bucket of any one of clauses LIII-LV, wherein said tension member includes a constant force spring.

LVII. The height-adjustable bucket of any one of clauses LIII-LVI, wherein said dampener is disposed on an underside of said base.

LVIII. A height-adjustable stand comprising: a medical device to be supported; a base; a support member coupled to said base; a carrier movably coupled to said support member and for supporting said medical device, wherein said carrier is configured to move between a relatively high position and a relatively low position along an axis relative to said relatively high position; a retainer selectively coupling said carrier and said support member and configured to retain said carrier in said relatively high position; and a lifting member coupled to said carrier and comprising a first end portion comprising an exterior engagement surface, and an engagement member, wherein said exterior engagement surface is configured to be activated by the user, and said engagement member is configured to be moved from a first position to a second position upon activation of the exterior engagement surface; and wherein said support member defines an interior engagement surface configured to be actuated by movement of said engagement member into said second position, and said support member comprises a piston configured to selectively uncouple said carrier and said support member to allow said carrier to move to said relatively low position upon actuation of the interior engagement surface by said engagement member.

LIX. The height-adjustable stand of clause LVIII, wherein said interior engagement surface is not visible when said lifting member is in said lowered position.

LX. The height-adjustable stand of any one of clauses LVIII or LIX, wherein a user engagement of said interior engagement surface does not actuate movement of said carrier from said relatively high position to said relatively low position.

LXI. The height-adjustable stand of any one of clauses LVIII-LX, wherein said retainer includes a first coupling member and said carrier includes a second coupling member and wherein at least one of said first coupling member and said second coupling member comprise magnetic material.

LXII. The height-adjustable stand of any one of clauses LVIII-LXI, wherein said carrier and said retainer are mechanically coupled when said carrier is in said relatively high position.

LXIII. The height-adjustable stand of any one of clauses LVIII-LXII, wherein said carrier and said retainer are magnetically coupled when said carrier is in said relatively high position.

LXIV. The height-adjustable stand of any one of clauses LVIII-LXIII, wherein said lifting member further comprises a biasing member configured to return said engagement member back to said first position from said second position.

LXV. The height-adjustable stand of any one of clauses LVIII-LXIV, further comprising a dampening assembly configured to provide controlled movement of said carrier.

LXVI. The height-adjustable stand of clause LXV, wherein said dampening assembly comprises a pulley, a tension member, and a dampener, said tension member extending between said dampener and said carrier to assist in moving said carrier between said relatively high position and said relatively low position, said pulley facilitating a change in direction of said tension member between said dampener and said carrier.

LXVII. The height-adjustable stand of any one of clauses LXV or LXVI, wherein said dampening assembly is a single direction system such that said dampening assembly is configured to provide controlled movement of said carrier only from said relatively high position to said relatively low position.

LXVIII. The height-adjustable stand of any one of clauses LXVI or LXVII, wherein said dampener is a rotary dampener.

LXIX. The height-adjustable stand of any one of clauses LXVI-LXVIII, wherein said tension member includes a constant force spring.

LXX. The height-adjustable stand of any one of clauses LXVI-LXIX, wherein said dampener is disposed on an underside of said base.

LXXI. The height-adjustable bucket of clause XXIII, wherein said retainer includes a first coupling member and said carrier includes a second coupling member and wherein at least one of said first coupling member and said second coupling member engage one another to retain said carrier in said relatively high position and define a force therebetween.

LXXII. The height-adjustable bucket of clauses XXIII or LXXI, wherein one of said first and second coupling members comprise a rod including a shoulder configured to be engaged with the other of said first and second coupling member.

LXXIII. The height-adjustable bucket of any of clauses XXIII or LXXI-LXXII, wherein said second coupling member comprises at least one ball-nose plunger configured to be engaged with said shoulder of said rod to retain said carrier in said relatively high position.

LXXIV. The height-adjustable bucket of ay of clauses XXIII or LXXI-LXXIII, wherein said rod includes at least one ramped surface disposed below said shoulder along said axis, and wherein said ramped surface is configured to allow said at least one ball-nose plunger to slide along said ramped surface during movement of said carrier from said relatively low position to said relatively high position.

LXXV. The height-adjustable bucket of any of clauses XXIII or LXXI-LXXIV, wherein said at least one ball-nose plunger is spring-loaded to assist said sliding motion of said at least one ball-nose plunger along said ramped surface of said rod.

LXXVI. The height-adjustable bucket of any of clauses XXIII or LXXI-LXXV, wherein when a force exerted on said carrier is greater than a force between said first coupling member and said second coupling member said at least one ball-nose plunger and said shoulder of said rod are configured to be repeatably decoupled.

LXXVII. The height-adjustable bucket of any of clauses XXIII or LXXI-LXXVI, further comprising a lifting member slidably coupled to said carrier, said lifting member including a first end portion comprising a handle and a second end portion, opposite said first end portion.

LXXVIII. The height-adjustable bucket of any of clauses XXIII or LXXI-LXXVII, further comprising a dampening assembly configured to provide controlled movement of said carrier.

LXXIX. The height-adjustable bucket of any of clauses XXIII or LXXI-LXXVIII, wherein said dampening assembly comprises a pulley, a tension member, and a dampener, said tension member extending between said dampener and said carrier to assist in moving said carrier between said relatively high position and said relativity low position, said pulley facilitating a change in direction of said tension member between said dampener and said carrier.

LXXX. The height-adjustable bucket of any of clauses XXIII or LXXI-LXXIX, wherein a force of said dampener is within 20% of said force between said retainer and said carrier.

LXXXI. A height-adjustable stand adapted to carry a medical object, said stand comprising: a medical device to be supported; a base having an upper most surface; a support member coupled to said base; a carrier movably coupled to said support member and for supporting said medical device, wherein said carrier is configured to move between a relatively high position and a relatively low position along an axis defined by said support member; and a retainer selectively coupling said carrier to said support member and configured to selectively retain said carrier in said relatively high position; and a dampening assembly configured to provide controlled movement of said carrier along a length of said axis defined between said relatively high position and said relatively low position, said dampening assembly comprising: a tension member coupled to said carrier; a dampener coupled to said base and positioned below said upper most surface of said base said dampener coupled to said tension member; and a pulley configured to change direction of said tension member between said carrier and said dampener.

LXXXII. The height-adjustable stand of clause LXXXI, wherein said dampener is a radial dampener.

LXXXIII. The height-adjustable stand of any of clause LXXXI or LXXXII, wherein said dampening assembly further includes a winder coupled to said tension member and configured to wind extra slack of said tension member during movement of said carrier between said relatively high position and said relatively low position.

LXXXIV. The height-adjustable stand of any one of clauses LXXXI-LXXXIII, wherein said dampener comprises a rotatable spool portion having a circumference and configured to receive said tension member, wherein when said carrier is in said relatively high position less than one circumference of length of said tension member is received by said spool portion and when said carrier is in said relatively low position more than one circumference of length of said tension member is received by said spool portion.

LXXXV. The height-adjustable stand of any one of clauses LXXXI-LXXXIV, wherein said dampening assembly defines a first dampening force when said carrier is in said relatively high position and said carrier and said retainer are in a decoupled configuration and said dampening assembly defines a second dampening force when said carrier is at a second height which is higher than said relatively low position and lower than said relatively high position, and said first dampening force is within 15% of said second dampening force.

LXXXVI. The height-adjustable stand of any one of clauses LXXXI-LXXXV, wherein said dampening assembly provides continuous dampening to movement of said carrier along said length of said axis from said relatively high position to said relatively low position.

LXXXVII. The height-adjustable stand of any one of clauses LXXXI-LXXXVI, wherein said dampening assembly is a one-way dampening assembly.

LXXXVIII. The height-adjustable stand of any one of clauses LXXXI-LXXXVII, wherein said medical device to be supported is a receptacle configured to carry the medical object.

LXXXIX. The height-adjustable stand of any one of clauses LXXXI-LXXXVIII, further comprising a lifting member slidably coupled to said carrier and configured to move between a lowered position and a raised position, said lifting member including a first end portion comprising a handle and a second end portion, opposite said first end portion comprising a stop member.

XC. The height-adjustable stand of clause LXXXIX, wherein said lifting member is configured to be in said lowered position when said carrier is in said relatively high position and when said carrier is in said relatively low position; and wherein said stop member is spaced from said carrier when said lifting member is in said lowered position and when said carrier is in said relatively high position.

XCI. A height-adjustable stand adapted to carry a medical object, said stand comprising: a medical device to be supported; a base; a support member coupled to said base; a carrier movably coupled to said support member and for supporting said medical device, wherein said carrier is configured to move between a relatively high position and a relatively low position along an axis defined by said support member; a retainer selectively coupling said carrier to said support member and configured to selectively retain said carrier in said relatively high position; and a dampening assembly configured to provide controlled movement of said carrier along said axis, said dampening assembly comprising: a tension member coupled to said carrier; and a radial dampener operably coupled to said tension member and configured to provide controlled movement of said carrier along said axis.

XCII. The height-adjustable stand of clause XCI, wherein said base comprises an upper most surface and said dampener is positioned below said upper most surface of said base.

XCIII. The height-adjustable stand of any one of clause XCI or XCII, wherein said dampening assembly further includes a pulley configured to change direction of said tension member between said carrier and said dampener.

XCIV. The height-adjustable stand of any one of clauses XCI-XCIII, wherein said dampening assembly further includes a winder coupled to said tension member and configured to wind extra slack of said tension member during movement of said carrier between said relatively high position and said relatively low position.

XCV. The height-adjustable stand of any one of clauses XCI-XCIV, wherein said dampener is coupled to said tension member by a plurality of circumferences of said tension member being spooled around said dampener.

XCVI. The height-adjustable stand of any one of clauses XCI-XCV, wherein said dampening assembly defines a first dampening force when said carrier is in said relatively high position and said carrier and said retainer are in a decoupled configuration and said dampening assembly defines a second dampening force when said carrier is at a second height which is higher than said relatively low position and lower than said relatively high position, and said first dampening force is within 15% of said second dampening force.

XCVII. The height-adjustable stand of any one of clauses XCI-XCVI, wherein said dampening assembly provides continuous dampening to movement of said carrier along said axis from said relatively high position to said relatively low position.

XCVIII. The height-adjustable stand of any one of clauses XCI-XCVII, wherein said dampening assembly is a one-way dampening assembly.

XCIX. The height-adjustable stand of any one of clauses XCI-XCVIII, wherein said medical device to be supported is a receptacle configured to carry the medical object.

C. The height-adjustable stand of any one of clauses XCI-XCIX, further comprising a lifting member slidably coupled to said carrier, said lifting member including a first end portion comprising a handle and a second end portion, opposite said first end portion.

CI. A height-adjustable medical stand adapted to carry a medical object comprising: a receptacle for carrying the medical object having a bottommost surface; a base; a support member coupled to said base; a carrier movably coupled to said support member for supporting a medical device, wherein said carrier is configured to move said receptacle between a minimum height of said bottommost surface and a maximum height of said bottommost surface along an axis defined by said support member, wherein said maximum height of said bottommost surface of said receptacle is at least two times greater than the minimum height of said bottommost surface of the receptacle.

CII. The height-adjustable stand of clause CI, further comprising a dampening assembly configured to provide controlled movement of said carrier when said carrier moves said receptacle from said maximum height of said bottommost surface to said minimum height of said bottommost surface.

CIII. The height-adjustable stand of clause CII wherein said dampening assembly defines a first dampening force when said receptacle is at said maximum height and said carrier and a retainer are in a decoupled configuration and said dampening assembly defines a second dampening force when said bottommost surface of said receptacle is at a second height which is higher than said minimum height and lower than said maximum height, and said first dampening force is within 15% of said second dampening force.

CIV. The height-adjustable stand of clauses CII or CIII, wherein said dampening assembly provides continuous dampening to movement of said carrier during movement of said receptacle along said axis from said maximum height to said minimum height.

CV. The height-adjustable stand of any of clauses CII-CIV, wherein said dampening assembly is a one-way dampening assembly that only exerts a dampening force when said carrier transitions from said receptacle moving from said maximum height towards said minimum height.

CVI. The height-adjustable stand of any of clauses CII-CV, wherein said dampening assembly includes a tension member coupled to said carrier and a radial dampener operably coupled to said tension member and configured to provide controlled movement of said carrier along said axis.

CVII. The height-adjustable stand of any of clauses CII-CVI, wherein said dampening assembly includes a tension member coupled to said carrier, a dampener coupled to said base and positioned below said upper most surface of said base said dampener coupled to said tension member, and a pulley configured to change direction of said tension member between said carrier and said dampener.

CVIII. The height-adjustable stand of any of clauses CII-CVII, further comprising a lifting member slidably coupled to said carrier, said lifting member including a first end portion comprising a handle and a second end portion, opposite said first end portion comprising a stop member configured to operatively engage said carrier.

CIX. The height-adjustable stand of clause CII-CVIII, wherein said lifting member is configured to move between a raised position and a lowered position and an upper most surface of said lifting member having a maximum height being less than the maximum height of the receptacle when said lifting member is in said lowered position.

What is claimed is:

1. A height-adjustable bucket adapted to carry a medical object, said height-adjustable bucket comprising:
a receptacle for receiving the medical object;
a base;
a support member coupled to said base;
a carrier movably coupled to said support member and for supporting said receptacle, wherein said carrier is configured to move between a relatively high position and a relatively low position along an axis defined by said support member;
a lifting member slidably coupled to said carrier and configured to move between a raised position and a lowered position, said lifting member comprising:
a first end portion comprising a handle;
a second end portion, opposite said first end portion, comprising a stop member configured to operatively engage said carrier; and
a retainer assembly selectively coupling said carrier to said support member and configured to selectively retain said carrier in said relatively high position,
wherein said lifting member is configured to be in said lowered position when said carrier is in said relatively high position and when said carrier is in said relatively low position; and wherein said stop member is spaced from said carrier when said lifting member is in said lowered position and when said carrier is in said relatively high position.

2. The height-adjustable bucket of claim 1, wherein said support member defines a rail, and said carrier includes a carriage assembly movably coupled to said rail.

3. The height-adjustable bucket of claim 1, further comprising a dampening assembly configured to provide controlled movement of said carrier.

4. The height-adjustable bucket of claim 3, wherein said dampening assembly comprises a pulley, a tension member, and a dampener, said tension member extending between said dampener and said carrier to assist in moving said carrier between said relatively high position and said relatively low position, said pulley facilitating a change in direction of said tension member between said dampener and said carrier.

5. The height-adjustable bucket of claim 4, wherein said dampening assembly is a single direction system such that said dampening assembly is configured to provide controlled movement of said carrier only from said relatively high position to said relatively low position.

6. The height-adjustable bucket of claim 4, wherein said dampener is a rotary dampener.

7. The height-adjustable bucket of claim 4, wherein said dampener is coupled to an underside of said base.

8. The height-adjustable bucket of claim 1, wherein said lifting member defines an exterior engagement surface and an engagement member, wherein said exterior engagement surface is configured to be activated by a user and said engagement member is configured to be moved from a first position to a second position upon activation of said exterior engagement surface to cause said carrier to be decoupled from said support member.

9. The height-adjustable bucket of claim 8, wherein said support member comprises an interior engagement surface configured to be actuated by said engagement member and a piston configured to selectively uncouple said retainer assembly and said carrier to allow said carrier to move to said relatively low position upon actuation of said interior engagement surface by said engagement member.

10. The height-adjustable bucket of claim 1, wherein said carrier and said retainer assembly are mechanically coupled to each other when said carrier is in said relatively high position.

11. A height-adjustable bucket adapted to carry a medical object, said bucket comprising:
 a receptacle for carrying the medical object;
 a base;
 a support member coupled to said base;
 a carrier movably coupled to said support member and said carrier for supporting said receptacle, wherein said carrier is configured to move between a relatively high position and a relatively low position along an axis defined by said support member, wherein said carrier comprises a coupling member; and
 a retainer on said support member selectively coupling said carrier to said support member and configured to selectively retain said carrier in said relatively high position,
 wherein when said carrier is in said relatively high position and said retainer is coupling said carrier to said support member, and wherein said coupling member of said carrier and said retainer are configured to automatically decouple from one another when contents of said receptacle has a mass greater than a predetermined mass that exceeds a retention force of said coupling member and said retainer.

12. The height-adjustable bucket of claim 11, wherein said retainer includes a first coupling member and said carrier includes a second coupling member and wherein at least one of said first coupling member and said second coupling member engage one another to retain said carrier in said relatively high position and define a force therebetween.

13. The height-adjustable bucket of claim 12, wherein one of said first and second coupling members comprise a rod including a shoulder configured to be engaged with the other of said first and second coupling member.

14. The height-adjustable bucket of claim 13, wherein said second coupling member comprises a ball-nose plunger configured to be engaged with said shoulder of said rod to retain said carrier in said relatively high position.

15. The height-adjustable bucket of claim 14, wherein said rod includes a ramped surface spaced apart from said shoulder along said axis, and wherein said ramped surface is configured to allow said ball-nose plunger to slide along said ramped surface during movement of said carrier from said relatively low position to said relatively high position.

16. The height-adjustable bucket of claim 15, wherein said ball-nose plunger is spring-loaded to assist sliding motion of said ball-nose plunger along said ramped surface of said rod.

17. The height-adjustable bucket of claim 11, further comprising a lifting member slidably coupled to said carrier, said lifting member including a first end portion comprising a handle and a second end portion, opposite said first end portion.

18. The height-adjustable bucket of claim 11, further comprising a dampening assembly configured to provide controlled movement of said carrier when said retainer is decoupled from said carrier.

19. The height-adjustable bucket of claim 18, wherein said dampening assembly comprises a pulley, a tension member, and a dampener, said tension member extending between said dampener and said carrier to dampen movement of said carrier from said relatively high position to said relativity low position, said pulley facilitating a change in direction of said tension member between said dampener and said carrier, wherein said dampener is configured to provide a dampening force that is within 20% of said force between said retainer and said carrier.

20. A height-adjustable stand adapted to carry a medical object, said stand comprising:
 a base having an upper most surface;
 a support member coupled to said base;
 a carrier movably coupled to said support member and for supporting a medical device, wherein said carrier is configured to move between a relatively high position and a relatively low position along an axis defined by said support member;
 a retainer selectively coupling said carrier to said support member and configured to selectively retain said carrier in said relatively high position;
 a dampening assembly configured to provide controlled movement of said carrier along a length of said axis defined between said relatively high position and said relatively low position, said dampening assembly comprising:
  a tension member coupled to said carrier;
  a dampener connected to said base and positioned below said upper most surface of said base with said dampener coupled to said tension member; and
  a pulley configured to change direction of said tension member between said carrier and said dampener.

* * * * *